(12) United States Patent
Batman et al.

(10) Patent No.: US 6,635,167 B1
(45) Date of Patent: Oct. 21, 2003

(54) APPARATUS AND METHOD FOR DETERMINING THE CONCENTRATION OF A COMPONENT OF A SAMPLE

(75) Inventors: Carol Jane Batman, Indianapolis, IN (US); Greg Paul Carpenter, Indianapolis, IN (US); Robert Glenn Davies, Carmel, IN (US); Richard J. Kasle, Indianapolis, IN (US); Kurt Gerard Klem, Indianapolis, IN (US); Robert Anthony Parks, Springport, IN (US); Timothy L. Ranney, Lebanon, IN (US); William Brothers, Lafayette, IN (US); Christopher Louis Belisle, Somerset, WI (US); Michael Steven Ray, Somerset, WI (US); Leonard Allen Vetsch, Elk Mound, WI (US); Marvin W. Glass, Fayetteville, TN (US); Richard W. Wilson, Noblesville, IN (US); James R. Parker, Carmel, IN (US); Vladimir Svetnik, Carmel, IN (US); Lynne Denise Sly, Fishers, IN (US); Sandy Mark Richards, Pershing, IN (US); Nancy Kennedy Byrd, Fishers, IN (US); Patricia A. Hopkinson, Lake Placid, NY (US)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/555,659
(22) PCT Filed: Dec. 4, 1998
(86) PCT No.: PCT/US98/25863
§ 371 (c)(1),
(2), (4) Date: Nov. 21, 2000
(87) PCT Pub. No.: WO99/28736
PCT Pub. Date: Jun. 10, 1999

Related U.S. Application Data
(60) Provisional application No. 60/067,512, filed on Dec. 4, 1997.

(51) Int. Cl.$^7$ ............... G01N 27/28; G01N 27/416; H01R 4/48
(52) U.S. Cl. ............ 205/775; 205/777.5; 204/400; 204/403.02; 204/406; 422/82.01; 324/431; 324/450; 439/786; 439/729; 439/759; 235/145 R
(58) Field of Search .................. 204/400, 403.02, 204/408, 406; 422/82.01, 50, 62, 82.05; 324/426, 431, 450; 439/786, 729, 759, 816; 205/775; 235/145 R

(56) References Cited

U.S. PATENT DOCUMENTS 3,577,137 A * 5/1971 Brennan, Jr. ............... 347/194

(List continued on next page.)

FOREIGN PATENT DOCUMENTS

JP 58-174860 11/1983

(List continued on next page.)

Primary Examiner—T. Tung
Assistant Examiner—Alex Noguerola
(74) Attorney, Agent, or Firm—Barnes & Thornburg

(57) ABSTRACT

An instrument (20) has a well (28a–b) for receiving a dry cell (75), an opening (78) through which a first connector (74) is exposed to the well (28a–b), and a boss (76) adjacent the opening (78). The boss (76) precludes the wrong terminal of the dry cell (75) from engaging the first connector (74) when the dry cell (75) is inserted into the well (28a–b) in incorrect orientation. A second connector (80) includes a base (81), a first leg (82) resiliently connected to and extending away from the base portion, a second leg (84) resiliently connected to and extending away from the first leg (82), and a third leg (86) resiliently connected to and extending away from the second leg (84) and toward the first leg (82). A display (42) for the instrument (20) has a lens (90) having a substantially transparent substrate with a polyurethane coating. The instrument housing has first and second portions. At least one locator pin (30) extends from one (24) of the housing portions and at least one complementary socket (32) extends from the other (22) of the housing portions for receiving the pin (30) to maintain the first (22) and second (24) portions in assembled orientation.

57 Claims, 65 Drawing Sheets

U.S. PATENT DOCUMENTS

| | | | | |
|---|---|---|---|---|
| 3,829,203 A | | 8/1974 | Novak | 352/78 R |
| 4,007,479 A | | 2/1977 | Kowalski | 29/760 |
| 4,032,729 A | * | 6/1977 | Koistinen | 200/5 A |
| 4,683,171 A | * | 7/1987 | Kuga et al. | 428/354 |
| 4,685,059 A | * | 8/1987 | Yamamoto | 422/82.05 |
| 4,726,929 A | * | 2/1988 | Gropper et al. | 422/82.04 |
| 4,963,814 A | | 10/1990 | Parks et al. | |
| 4,999,582 A | | 3/1991 | Parks et al. | |
| 4,999,632 A | | 3/1991 | Parks | |
| 5,001,417 A | * | 3/1991 | Pumphrey et al. | 324/71.5 |
| 5,074,977 A | * | 12/1991 | Cheung et al. | 205/775 |
| 5,127,849 A | * | 7/1992 | Karl et al. | 439/500 |
| 5,250,262 A | * | 10/1993 | Heidt et al. | 422/64 |
| 5,282,950 A | * | 2/1994 | Dietze et al. | 204/406 |
| 5,288,636 A | | 2/1994 | Pollmann et al. | |
| 5,366,609 A | | 11/1994 | White et al. | |
| 5,395,504 A | * | 3/1995 | Saurer et al. | 204/403.03 |
| 5,508,171 A | | 4/1996 | Walling et al. | |
| 5,526,280 A | * | 6/1996 | Consadori et al. | 702/24 |
| 5,565,865 A | * | 10/1996 | So | 341/20 |
| 5,658,801 A | | 8/1997 | Poissant et al. | 436/518 |
| 5,660,791 A | * | 8/1997 | Brenneman et al. | 422/58 |
| 5,718,816 A | * | 2/1998 | Savage et al. | 204/403.03 |
| 5,746,626 A | * | 5/1998 | Kwiat et al. | 439/630 |
| 5,931,791 A | * | 8/1999 | Saltzstein et al. | 600/513 |
| 6,066,243 A | * | 5/2000 | Anderson et al. | 422/82.01 |

FOREIGN PATENT DOCUMENTS

| | | | |
|---|---|---|---|
| JP | | 61-120174 | 7/1986 |
| JP | | 62-202774 | 12/1987 |
| JP | | 63-43355 | 3/1988 |
| JP | | 4-23054 | 2/1992 |
| JP | | 4-254748 | 9/1992 |
| WO | | 97/42882 A1 * | 11/1997 |

* cited by examiner

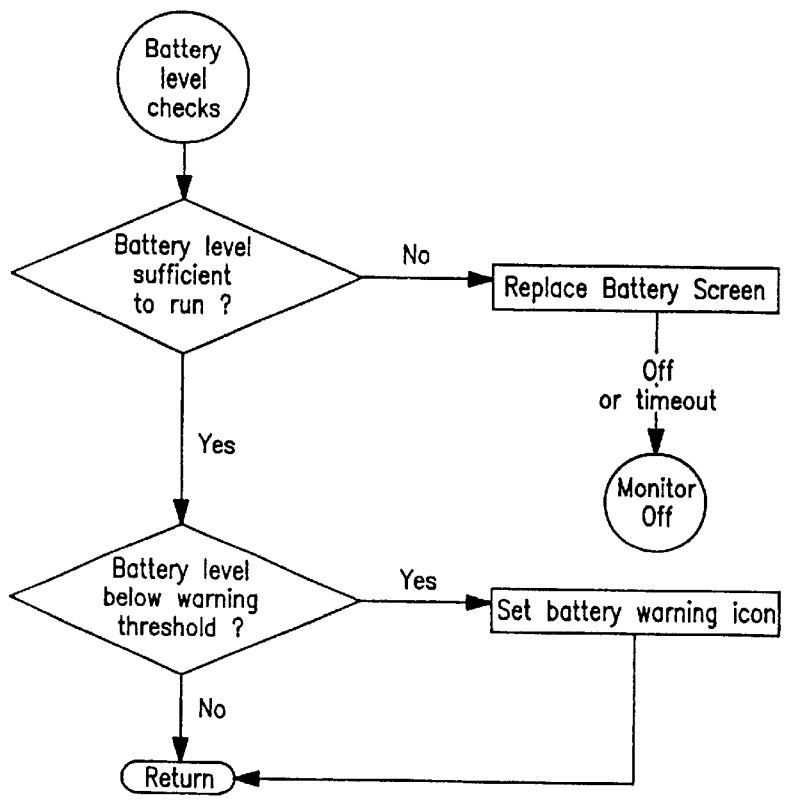
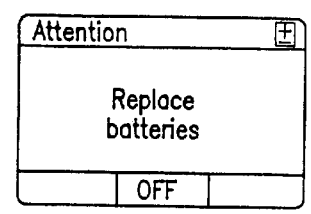
FIG. 27A  FIG. 27B
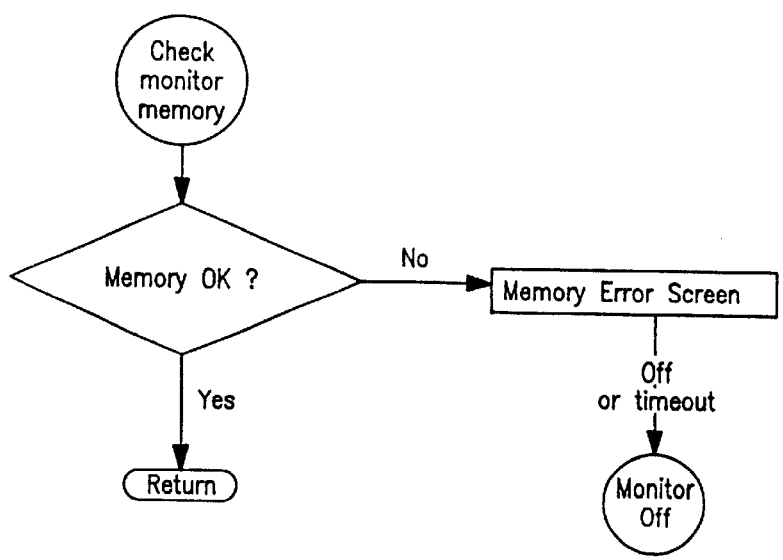
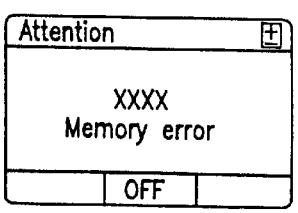
FIG. 28A  FIG. 28B

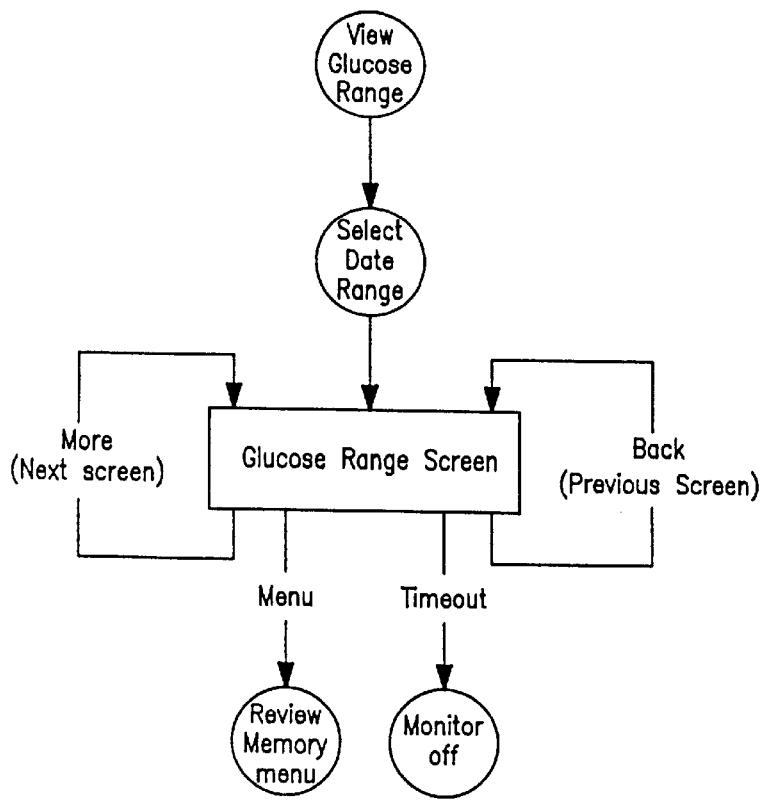
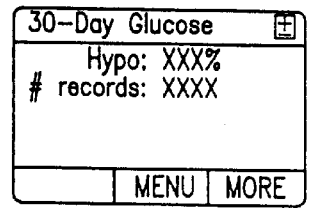
FIG. 41B
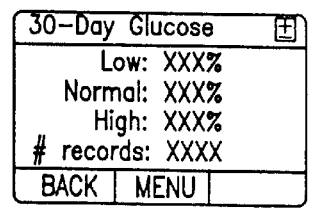
FIG. 41C
FIG. 41A
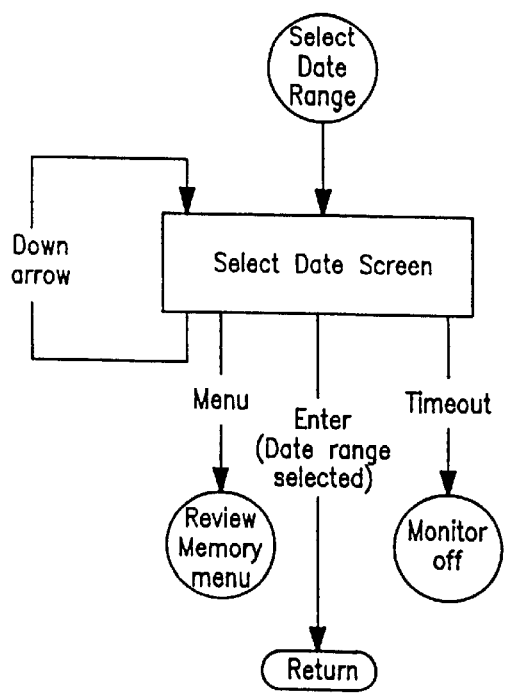
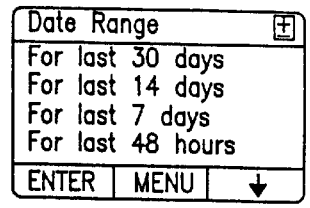
FIG. 42B
FIG. 42A

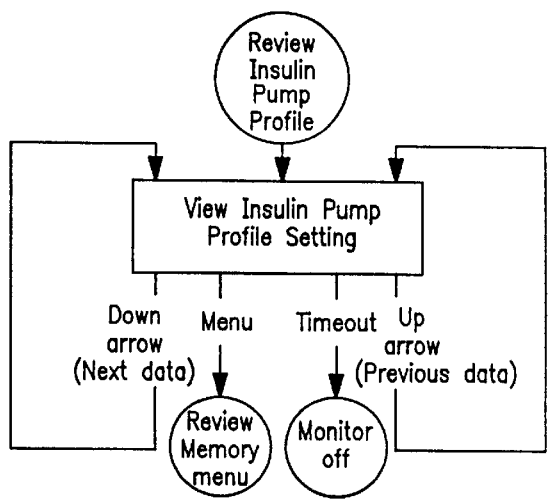
FIG. 45B
FIG. 45A
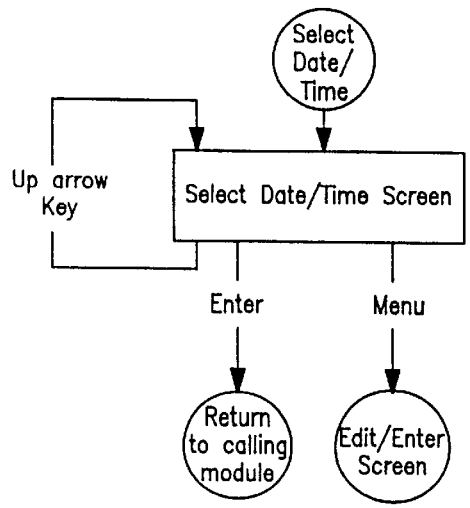
FIG. 48A
FIG. 48B
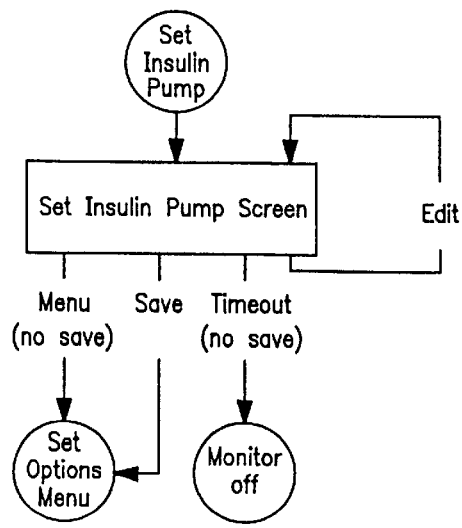
FIG. 64A
FIG. 64B

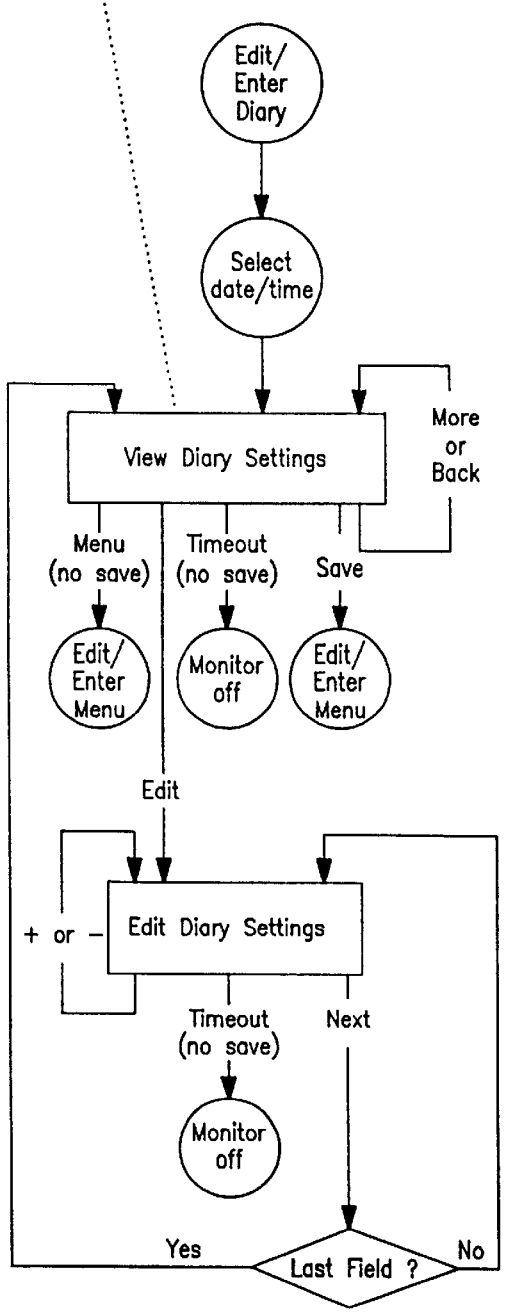

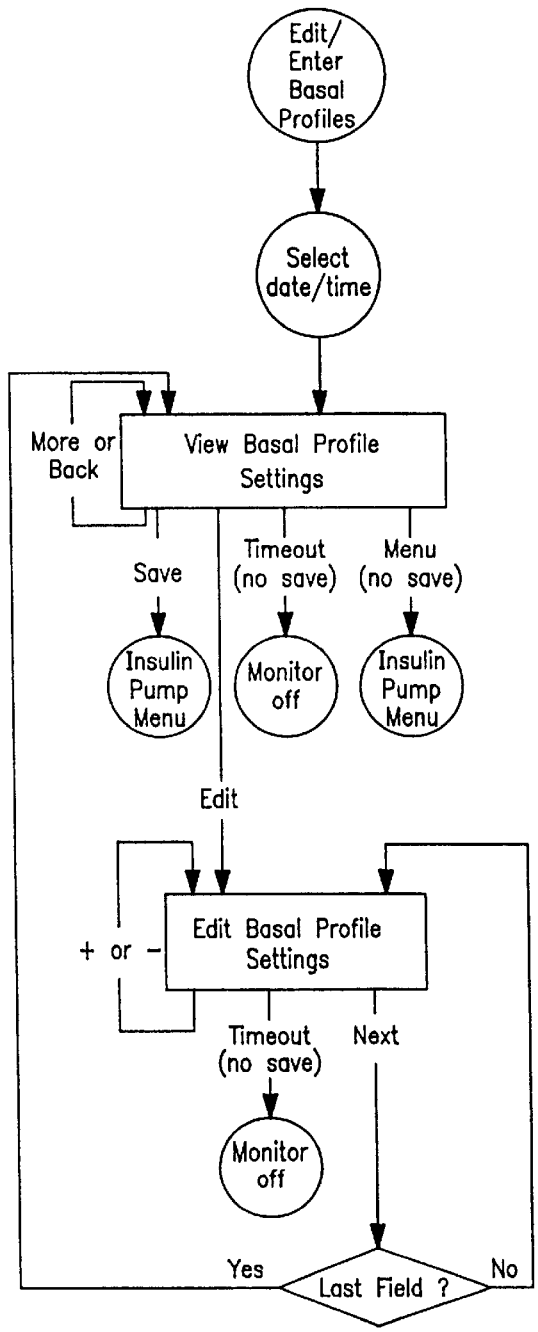
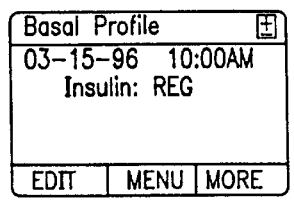 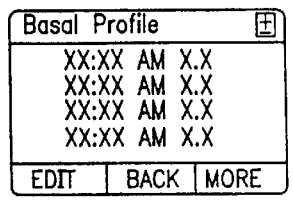
FIG. 54B          FIG. 54C
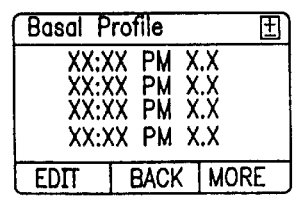 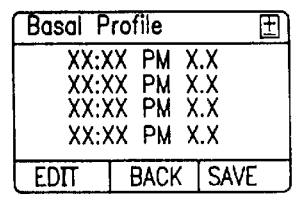
FIG. 54D          FIG. 54E
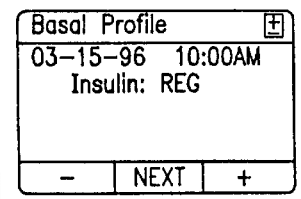 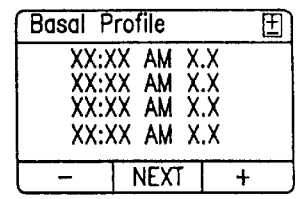
FIG. 54F          FIG. 54G
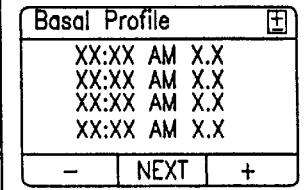 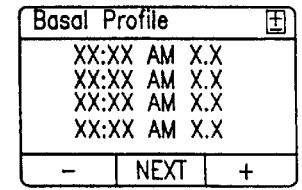
FIG. 54H          FIG. 54I
FIG. 54A

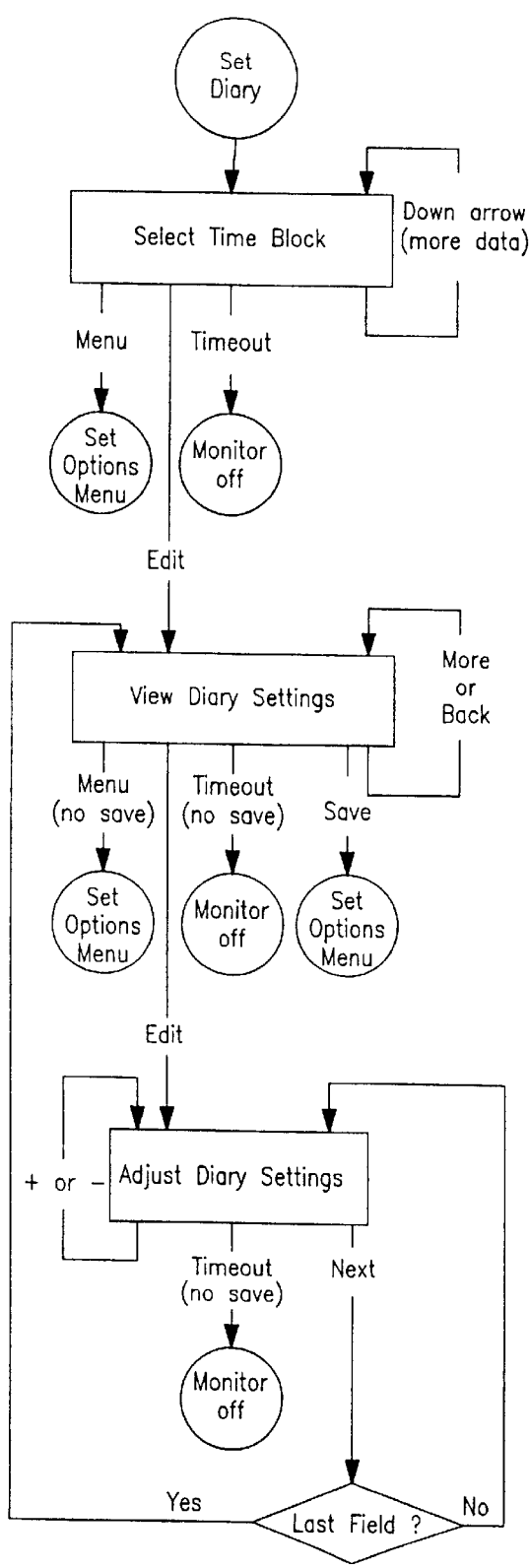

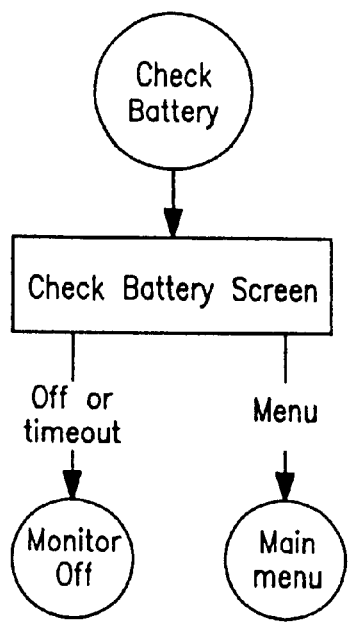
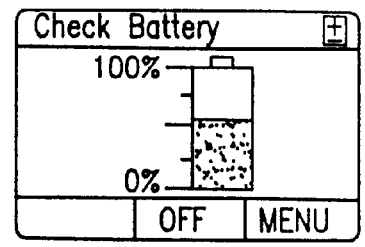
FIG. 69B
FIG. 69A
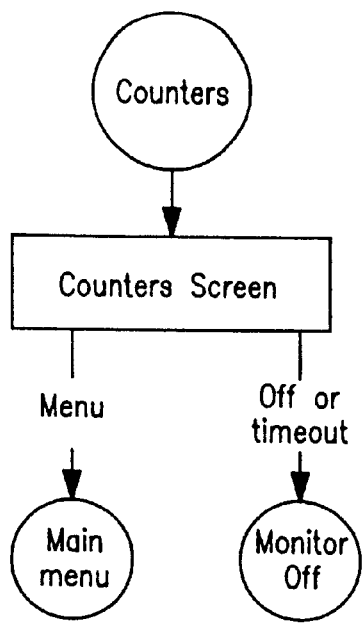
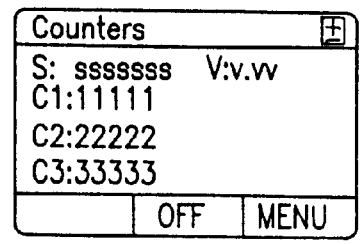
FIG. 70B
FIG. 70A

APPARATUS AND METHOD FOR DETERMINING THE CONCENTRATION OF A COMPONENT OF A SAMPLE

This is a related application to U.S. Ser. No. 60/067,512, titled INSTRUMENT, filed Dec. 4, 1997, U.S. Ser. No. 60/067,499, filed Dec. 4, 1997, titled INSTRUMENT SETUP UTILITY PROGRAM, and U.S. Ser. No. 09/ 555, 718 pending, titled INSTRUMENT SETUP UTILITY PROGRAM, filed on Jun. 2, 2000. These related applications are assigned to the same assignee as this application. The disclosures of those applications are incorporated herein by reference.

BACKGROUND OF THE INVENTION

This invention relates to improvements in instruments of the general type described in U.S. Pat. Nos. 4,963,814; 4,999,582; 4,999,632; 5,288,636; 5,366,609; and, 5,508, 171. It is disclosed in the context of such instruments. However, it is believed to be useful in other applications as well.

Hand held instruments for the determination of physical and biological parameters such as, for example, the concentrations of medically significant components, such as glucose, of biological fluids, such as blood, are in widespread use. Such instruments permit people to monitor such characteristics and treat themselves or take other appropriate action to halt or reverse undesirable trends in the concentrations of such components. In diabetics, for example, such corrective action might be something as simple as intake of a particular type of food, for example, fruit juice, or an injection of insulin. In persons who are monitoring a clotting characteristic of their blood, such corrective action might be, for example, taking of a blood thinner or clotting factor.

DISCLOSURE OF THE INVENTION

An electrical apparatus for use with an electrical cell for providing power includes a first connector for contacting one of the terminals of the cell and a second connector for contacting the other of the terminals of the cell when the cell is installed in the apparatus. The second connector includes a base portion fixed in the apparatus, a first leg portion resiliently connected to and extending away from the base portion, a second leg portion resiliently connected to and extending away from the first leg portion, and a third leg portion resiliently connected to and extending away from the second leg portion and toward the first leg portion. Installation of the cell in the apparatus causes the other terminal to resiliently engage the second leg portion.

Illustratively according to this aspect of the invention, the second leg portion also extends away from the base portion.

Further illustratively according to this aspect of the invention, the third leg portion has an extension that extends away from the base portion.

Additionally illustratively according to this aspect of the invention, the electrical apparatus comprises an instrument for determining the concentration of a medically significant component of a biological sample.

Illustratively according to this aspect of the invention, the electrical cell comprises a dry cell. The installation of the dry cell into the apparatus causes the one terminal to engage the first connector.

Further illustratively according to this aspect of the invention, the electrical apparatus includes a well for receiving the cell. The well includes an opening through which the first connector is exposed to the well, and a boss adjacent the opening. The boss precludes the other terminal from engaging the first connector when the cell is inserted into the well in incorrect orientation.

Additionally illustratively according to this aspect of the invention, the electrical apparatus includes a circuit board to which the base portion of the second connector is fixed.

Illustratively according to this aspect of the invention, the first leg portion of the second connector extends away from the base portion at an angle between about five degrees and about ten degrees with respect to a line perpendicular to the base portion and generally in a first direction. The second leg portion extends away from the first leg portion at an angle between about fifteen degrees and about twenty five degrees with respect to the perpendicular line and generally in a second direction opposite to the first direction. The third leg portion extends toward the base portion at an angle of between about forty degrees and about fifty degrees with respect to the perpendicular line and generally in the first direction.

Further illustratively according to this aspect of the invention, the second connector comprises BeCu 190 alloy.

Additionally according to this aspect of the invention, the second connector comprises a 60/40 tin/lead plating.

Illustratively according to this aspect of the invention, the radii of curvature of the portions of the second connector between the base portion and the first leg portion, the first leg portion and the second leg portion, and the second leg portion and the third leg portion are substantially constant.

Further illustratively according to this aspect of the invention, the third leg portion has an extension that extends away from the base portion, and the radius of curvature of the portion of the second connector between the extension and the third leg portion is also substantially constant.

According to another aspect of the invention, an apparatus for determining the concentration of a medically significant component of a biological sample includes a display for displaying an operational status thereof, the display having a lens consisting essentially of a substantially transparent substrate with a polyurethane coating.

Illustratively according to this aspect of the invention, the substantially transparent substrate is constructed from polycarbonate resin.

According to another aspect of the invention, an apparatus for determining the concentration of a medically significant component of a biological sample comprises a housing having first and second portions, at least one locator pin extending from one of the housing portions and at least one complementary socket extending from the other of the housing portions for receiving the pin to maintain the first and second portions in assembled orientation.

Illustratively according to this aspect of the invention, the locator pin and the complementary socket have substantially circular cross sections perpendicular to their longitudinal extents.

Further illustratively according to this aspect of the invention, the engaging surfaces of the locator pin and the complementary socket are provided with complementary drafts to provide sufficient frictional engagement to hold the first and second portions together when they are assembled.

Additionally illustratively according to this aspect of the invention, the apparatus includes at least two locator pins and two complementary sockets.

Illustratively according to this aspect of the invention, both of the locator pins are disposed on the first housing portion and both of the complementary sockets are disposed on the second housing portion such that the locator pins are received in the respective ones of the complementary sockets when the first and second housing portions are assembled together.

According to another aspect of the invention, an apparatus for determining the concentration of a medically significant component of a biological sample includes first and second keys for use in operating the apparatus. The keys extend from a common support mounted in the apparatus. Each of the keys has a reduced cross sectional portion adjacent to the common support to promote substantially independent activation of the first and second keys.

Illustratively according to this aspect of the invention, the apparatus comprises a third key disposed between the first and second keys for use in operating the apparatus. The third key also has a reduced cross sectional portion adjacent to a second support mounted in the apparatus.

Further illustratively according to this aspect of the invention, the common support has a relief portion for receiving the second support such that the three keys generally define a surface when the apparatus is assembled.

Additionally illustratively according to this aspect of the invention, the apparatus includes a housing having first and second portions. The apparatus includes a circuit mounted to one of the housing portions and having a set of three terminals. The apparatus further includes means for securing the keys when the first and second housing portions are assembled together such that the keys, when activated, operate respective ones of the terminals.

Illustratively according to this aspect of the invention, the apparatus includes a compressible member disposed between the keys and the terminals of the circuit.

Further illustratively according to this aspect of the invention, the compressible member comprises a resilient pad dimensioned to isolate the terminals physically to reduce the possibility of contaminants interfering with the operation of the instrument.

Additionally illustratively according to this aspect of the invention, the means for securing the keys comprises pins extending from the other housing portion for reception in a corresponding plurality of openings disposed in the key supports to capture the supports between the other housing portion and the circuit.

According to another aspect of the invention, an apparatus for determining the concentration of a medically significant component of a biological sample comprises a strip and an instrument. The instrument comprises a slot through which the strip is intended to be inserted. The strip has at least one electrical contact thereon in communication with the sample. The instrument includes an electrical connector for engagement with the electrical contact of the strip when the strip is inserted into the instrument for determining the concentration. The instrument includes first and second housing portions. The slot is provided in one of the housing portions and the connector is mounted in the other of the housing portions. The other housing portion includes a member fixed thereto to engage the connector resiliently when the housing portions are assembled together to promote alignment of the connector with the slot.

Illustratively according to this aspect of the invention, the apparatus includes a circuit board mounted in the other housing portion. The electrical connector is disposed on the circuit board.

Further illustratively according to this aspect of the invention, the slot has a rib portion for guiding the strip when the strip is inserted into the instrument to promote engagement of the electrical contact of the strip with the electrical connector of the instrument.

Additionally illustratively according to this aspect of the invention, the resilient engagement of the member with the connector promotes alignment of the connector with the slot generally in a first direction. The rib portions guides the strip in a second direction generally perpendicular to the first direction.

Illustratively according to this aspect of the invention, the apparatus includes a second member fixed to the other housing portion for resiliently engaging the connector when the housing portions are assembled together to promote alignment of the connector with the slot in cooperation with the first-mentioned member.

According to another aspect of the invention, a method is provided for operating an instrument. The instrument includes a housing for at least some of the instrument components. The instrument components housed within the housing have at least first and second operating states. The instrument components evolve heat at a first time rate when the instrument is in the first operating state and at a second time rate when the instrument is in the second operating state. The instrument components include a controller. The controller keeps a record of how long the instrument is operated in each of said first and second states and calculates from the record the heating of the interior of the housing resulting from the operation of the instrument in each of said first and second states.

Illustratively according to this aspect of the invention, the instrument components housed within the instrument include a device for producing an output indicative of temperature. The method further comprises the step of adjusting the indicated temperature based upon the calculated heating of the interior of the housing.

Further illustratively according to this aspect of the invention, the step of adjusting the indicated temperature based upon the calculated heating of the interior of the housing comprises the step of subtracting the calculated heating of the interior of the housing from the indicated temperature.

Additionally illustratively according to this aspect of the invention, the instrument comprises an instrument for determining the concentration of a medically significant component of a sample. The method further comprises providing a strip, dosing the strip with the sample, providing on the instrument a port for receiving the strip, inserting the dosed strip into the port, determining an ambient temperature within the housing, adjusting the determined ambient temperature to an adjusted ambient temperature based upon the heating of the interior of the housing resulting from the operation of the instrument in each of said first and second states, and determining the concentration of the medically significant component of the sample based upon the adjusted ambient temperature.

Illustratively according to this aspect of the invention, the strip contains a chemistry for reacting with the medically significant component of the sample and producing across two terminals of the strip a signal indicative of the reaction. Dosing of the strip followed by receiving the strip in the port enables the determination of the first concentration.

Further illustratively according to this aspect of the invention, the medically significant component is glucose and the chemistry reacts with glucose to produce at least one of a voltage and a current indicative of the glucose concentration of the sample across the terminals of the strip.

According to another aspect of the invention, an instrument includes a housing for at least some of the instrument components. The instrument components housed within the housing have at least first and second operating states. The instrument components evolve heat at a first time rate when the instrument is in the first operating state and at a second time rate when the instrument is in the second operating state. The instrument components include a controller for keeping a record of how long the instrument is operated in each of said first and second states and calculating from the record the heating of the interior of the housing resulting from the operation of the instrument in each of said first and second states.

Illustratively according to this aspect of the invention, the instrument components housed within the instrument include a device for producing an output indicative of temperature. The controller is coupled to the device for producing an output indicative of temperature for adjusting the indicated temperature based upon the calculated heating of the interior of the housing.

Further illustratively according to this aspect of the invention, the controller is coupled to the device for producing an output indicative of temperature for subtracting the calculated heating of the interior of the housing from the indicated temperature.

Additionally illustratively according to this aspect of the invention, the instrument comprises an instrument for determining the concentration of a medically significant component of a sample. The apparatus further comprises a strip for dosing with the sample. The instrument includes a port for receiving the strip. The controller adjusts the determined ambient temperature to an adjusted ambient temperature based upon the heating of the interior of the housing resulting from the operation of the instrument in each of said first and second states. The instrument determines the concentration of the medically significant component of the sample based upon the adjusted ambient temperature.

Illustratively according to this aspect of the invention, the strip contains a chemistry for reacting with the medically significant component of the sample and at least two strip terminals. The port includes at least two complementary instrument terminals. The strip terminals make contact with respective instrument terminals when the strip is inserted into the port. The chemistry reacts with the medically significant component of the sample to produce across at least two of the strip terminals a signal indicative of the reaction. Receiving the strip in the port and dosing of the strip enables the determination of the first concentration.

Further illustratively according to this aspect of the invention, the medically significant component is glucose and the chemistry reacts with glucose to produce at least one of a voltage and a current indicative of the glucose concentration of the sample across the strip terminals.

According to another aspect of the invention, an instrument for determining the concentration of a medically significant component of a sample includes a controller and a power supply for providing power to the controller. The power supply includes an inductance, a first solid state switch in circuit with the inductance, a first rectifier and a first capacitance in a second circuit for rectifying and storing the voltage variations appearing across one of the first switch and inductance. The controller provides a first switching signal for the first switch.

Illustratively according to this aspect of the invention, the apparatus further comprises a second rectifier and a second capacitance in a third circuit for rectifying and storing the voltage variations appearing across one of the first switch and inductance. The second circuit stores voltage variations of a first polarity appearing across one of the first switch and inductance and the third circuit stores voltage variations of a second and opposite polarity appearing across one of the first switch and inductance.

Further illustratively according to this aspect of the invention, the apparatus further comprises a transistor-transistor logic-to-RS-232 (TTL-to-RS-232) interface. The TTL-to-RS-232 interface is coupled across the second circuit and the third circuit.

Additionally illustratively according to this aspect of the invention, the apparatus further comprises a third rectifier and a third capacitance. The second and third rectifiers and the second and third capacitances are in a fourth circuit configured as a voltage multiplier.

Illustratively according to this aspect of the invention, the apparatus further comprises a second switch in circuit with the first capacitance. The controller further provides a second switching signal for the second switch.

Further illustratively according to this aspect of the invention, the second switch comprises a second solid state device for regulating the voltage across the first capacitance when the second switch is in a first state. The second solid state device halts regulation of the voltage across the first capacitance when the second switch is in a second state.

Additionally illustratively according to this aspect of the invention, the first switching signal is pulsewidth modulated.

According to another aspect of the invention, an instrument for determining the concentration of a medically significant component of a sample includes a controller and a display for displaying at least one of test status and results of tests to determine the concentration of the medically significant component of a sample. The controller is coupled to the display to display a first group of multiple results having a common characteristic simultaneously.

Illustratively according to this aspect of the invention, the common characteristic is that the multiple results of the first group were taken within twenty-four hours of each other.

Further illustratively according to this aspect of the invention, the results of the first group are displayed chronologically.

Additionally according to this aspect of the invention, the controller further controls the display to display a second group of multiple results taken within the same twenty-four hours as are the results of the first group.

Illustratively according to this aspect of the invention, the results of the first group are displayed chronologically whenever they are displayed and the results of the second group are displayed chronologically whenever they are displayed.

Further illustratively according to this aspect of the invention, the results of the first group and, where present, the second group, are assignable to respective time intervals within the same twenty-four hour period, which time intervals are user-selectable.

Additionally illustratively according to this aspect of the invention, the instrument further comprises a key for permitting the user to select to have the results of the first group or the results of the second group displayed at a given time.

According to another aspect of the invention, an instrument for determining the concentration of a medically significant component of a sample includes at least one key for the entry of information by a user, a controller for assigning to the at least one key a function selected from a group of at least two functions, and a display for displaying for the user an assignment by the controller of the function to the at least one key.

Illustratively according to this aspect of the invention, the apparatus further comprises a strip for dosing with the sample. The instrument includes a port for receiving the strip to enable the instrument to determine the concentration of the medically significant component of the sample.

Further illustratively according to this aspect of the invention, the strip contains a chemistry for reacting with the medically significant component of the sample and a pair of strip terminals. The port includes a complementary pair of instrument terminals. The strip terminals make contact with respective instrument terminals when the strip is inserted into the port. The chemistry reacts with the medically significant component of the sample to produce across the pair of strip terminals a signal indicative of the reaction. Receiving the strip in the port and dosing of the strip enables the determination of the first concentration.

Additionally illustratively according to this aspect of the invention, the medically significant component is glucose and the chemistry reacts with glucose to produce at least one of a voltage and a current indicative of the glucose concentration of the sample across the pair of strip terminals.

Illustratively according to this aspect of the invention, the instrument comprises a hand held instrument for determining the glucose concentration of the sample.

Further illustratively according to this aspect of the invention, the strip contains a chemistry for reacting with the medically significant component of the sample. The port includes a device for assessing the reaction of the chemistry with the medically significant component of the sample and for producing a signal indicative of the assessment. Dosing of the strip and receiving the strip in the port enables the determination of the concentration.

According to another aspect of the invention, an instrument for determining the concentration of a medically significant component of a sample includes a controller, at least one key for the entry of information by a user, and a display for displaying results of tests to determine the concentration of the medically significant component of a sample. The controller is coupled to the at least one key and to the display to permit the user to enter into the controller a first range of values for the concentration of the medically significant component of the sample. The display displays the first range. The controller produces an indication during a subsequent determination of the concentration whether the subsequently determined concentration falls within the first range.

Illustratively according to this aspect of the invention, the instrument comprises a hand held instrument for determining the glucose concentration of the sample.

Further illustratively according to this aspect of the invention, the apparatus further comprises a strip for dosing with the sample. The instrument includes a port for receiving the strip to enable the instrument to determine the concentration of the medically significant component of the sample.

Additionally illustratively according to this aspect of the invention, the medically significant component is glucose and the chemistry reacts with glucose to produce an indication of the glucose concentration of the sample.

Illustratively according to this aspect of the invention, the controller further permits the user to enter into the controller a second range of values for the concentration of the medically significant component of the sample. The display displays the second range. The controller produces an indication during a subsequent determination of the concentration whether the subsequently determined concentration falls within the second range.

BRIEF DESCRIPTION OF THE DRAWINGS

The invention may best be understood with reference to the following detailed description and accompanying drawings which illustrate the invention. In the drawings:

FIGS. 19–70b illustrate the user interface of the instrument illustrated in FIG. 1.

Figure 1:
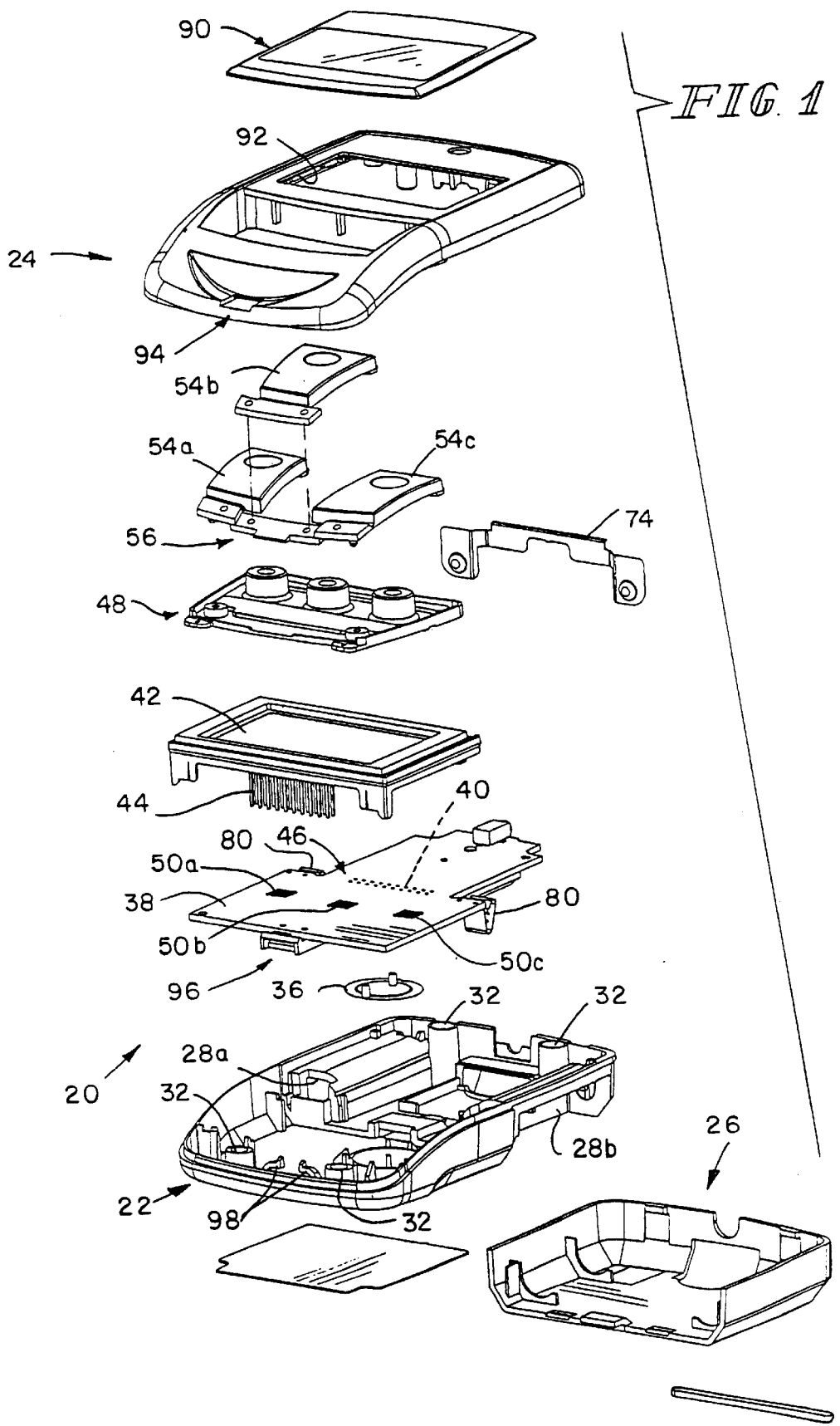
FIG. 1 illustrates an exploded perspective view of an instrument incorporating the invention.
Figure 2:
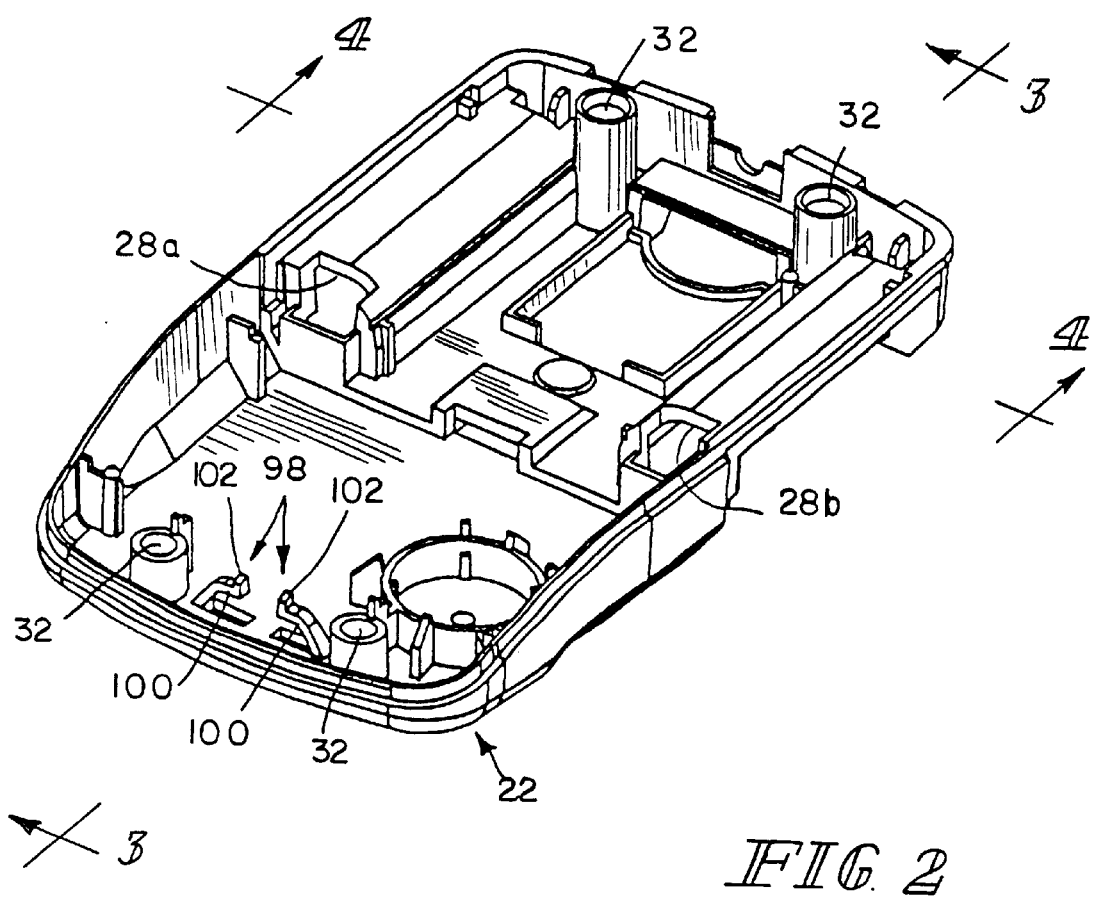
FIG. 2 illustrates an enlarged perspective view of a detail of the instrument illustrated in FIG. 1.
Figure 8:
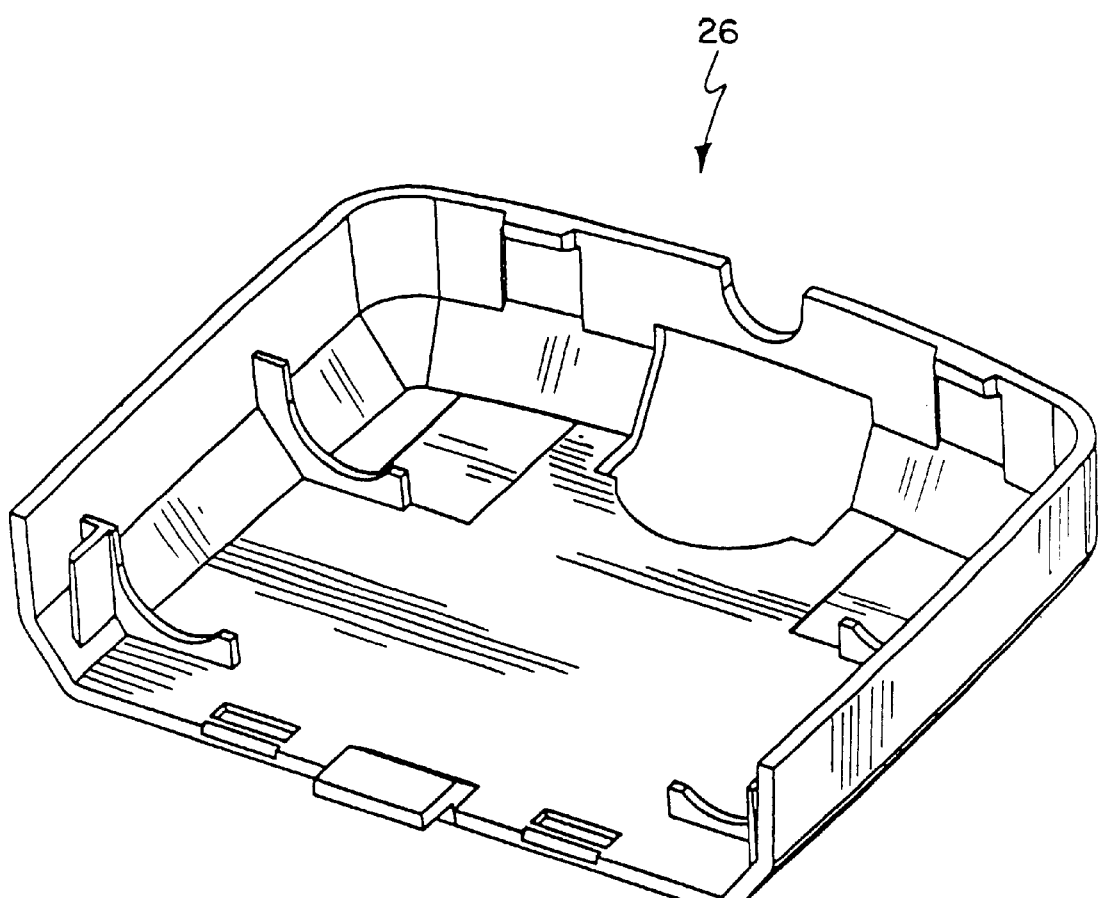
FIG. 8 illustrates an enlarged perspective view of a detail of the instrument illustrated in FIG. 1.
Figure 13:
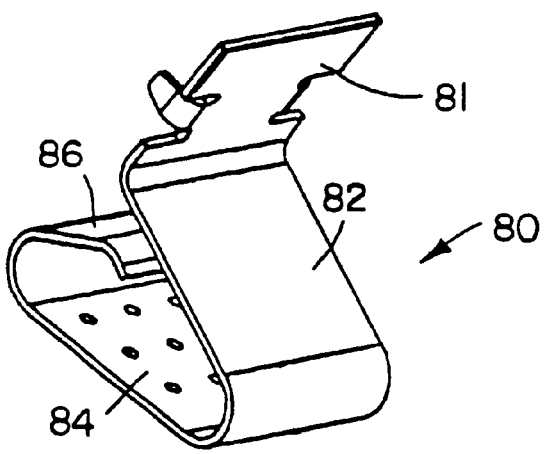

Turning now particularly to FIG. 1, an instrument 20 for the determination of the glucose concentration of blood cooperates with a so-called biosensor strip 21 (FIG. 13) of the general type described in the above identified patents. The instrument 20 includes a case bottom portion 22 (FIGS. 1–4) and a case top portion 24 (FIGS. 1 and 5–7) for housing the remaining components of the instrument 20. A battery door 26 (FIGS. 1 and 8) engages bottom portion 22 and encloses two battery wells 28a and b provided in bottom portion 22. Bottom portion 22 and top portion 24 are held together substantially exclusively by the frictional engagement of pins 30 molded into the underside of top portion 24 in complementary sockets 32 molded into bottom portion 22. Slight drafts, for example, about 0.06 mm along the approximately 0.6 mm to 0.7 mm effective heights of sockets 32 and pins 30, are sufficient to facilitate removal of these molded components from their molds, while still providing sufficient frictional engagement to hold top and bottom portions 22, 24 together with the remaining instrument 20 components assembled in them.

Figure 9:
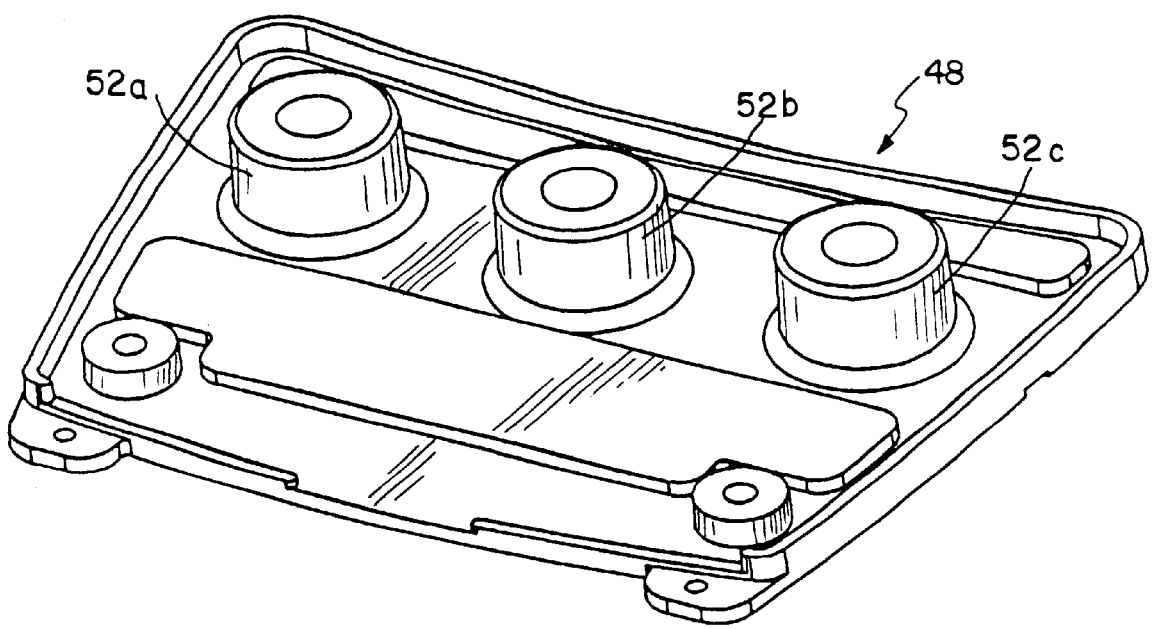
FIG. 9 illustrates an enlarged perspective view of a detail of the instrument illustrated in FIG. 1.
Figure 10:
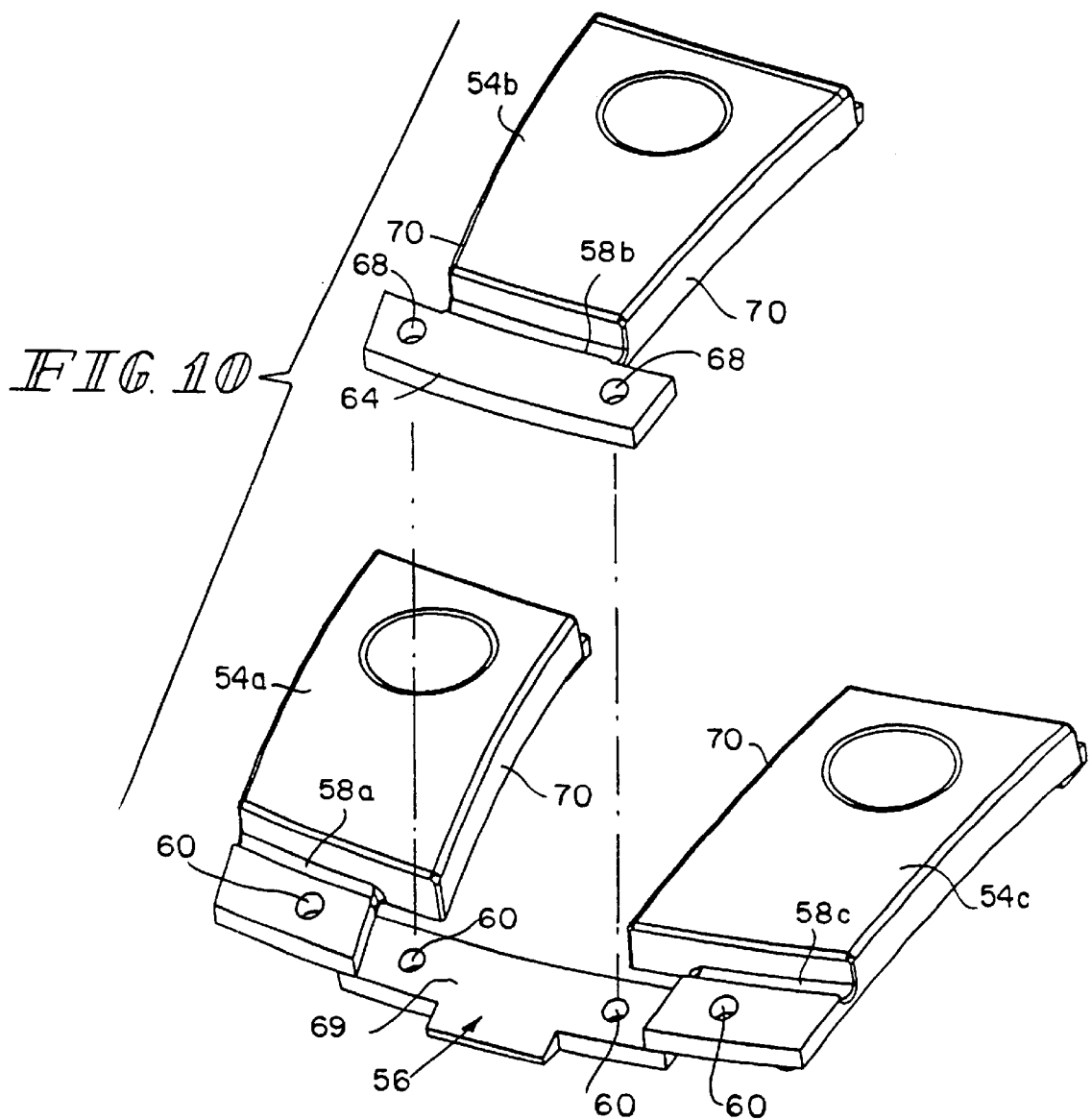
FIG. 10 illustrates enlarged perspective views of details of the instrument illustrated in FIG. 1.

A well is provided in bottom portion 22 for a brass contact plate 36 for a piezoelectric speaker or buzzer 37 (FIG. 14) which is mounted on the underside of a printed circuit board 38 in instrument 20. A socket 40 is provided on the underside of PCB 38 to make connections to a liquid crystal display 42, the pins 44 of which are inserted into socket 40 through holes 46 provided therefor in PCB 38. This arrangement aids in the manufacture of the circuit board 38 and reduces manufacturing cost. Display 42 illustratively is a 102-by-65 dot matrix LCD. A flexible silicone button pad 48 (FIGS. 1 and 9) has terminals or contacts provided on the underside thereof for contact with complementary terminals or contacts 50a–c on PCB 38. The tactile cushion portions 52a–c of button pad 48 cooperate with three keys 54a–c (FIGS. 1 and 10) mounted on top portion 24 to provide inputs to instrument 20.

The two outer keys 54a and c are molded together, but each is joined to their common support bar 56 by a living hinge 58a, 58c, respectively. Living hinges 58a and c are regions of the molded plastic key 54a, c assembly that are somewhat thinner and of reduced width to make the keys 54a, c themselves somewhat more touch sensitive than would be the case without the living hinge structure, and to aid in isolating key presses of key 54a from those of key 54c. Openings 60 are provided in the support bar 56 to receive pins 62 which protrude from the underside of top portion 24 to receive the key 54a, c assembly. The remaining key 54b is mounted from a similar support bar 64 by a similar living hinge 58b to permit bar 64 to engage the two middle pins 62. The assembly including the compressible silicone pad 48, key 54a, c assembly, and key 54b is captured between the underside of top portion 24 and PCB 38. Again, pins 62 protrude from the underside of top portion 24 to be received in openings 68 provided in bar 64 of key 54b. A depression 69 in bar 56 accommodates bar 64. Key 54b is constructed separately from the keys 54a, c to minimize the spacing between the adjacent surfaces 70 of key 54b and keys 54a and c. The use of the silicone pad 48 and keys 54a–c, and the minimal spacing between adjacent keys 54a–b and b–c help to reduce the possibility of contaminants interferring with the operation of instrument 20.

Figure 11:
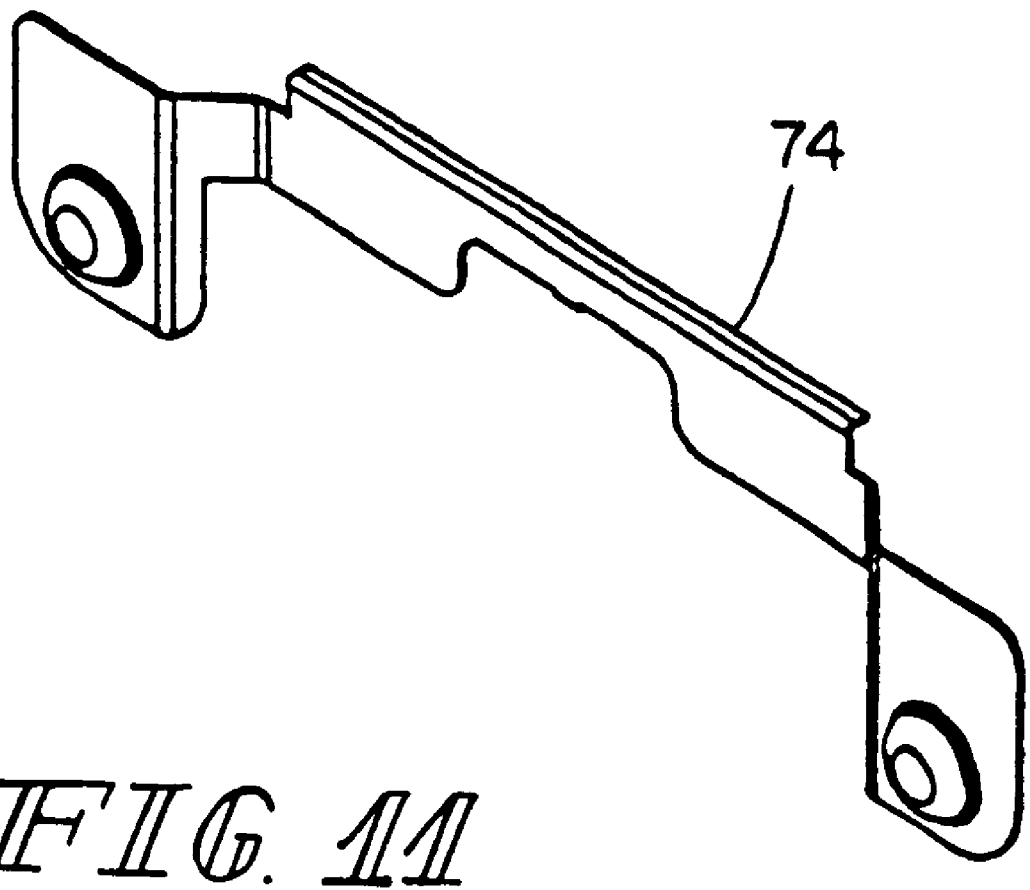
FIG. 11 illustrates an enlarged perspective view of a detail of the instrument illustrated in FIG. 1.
Figure 12:
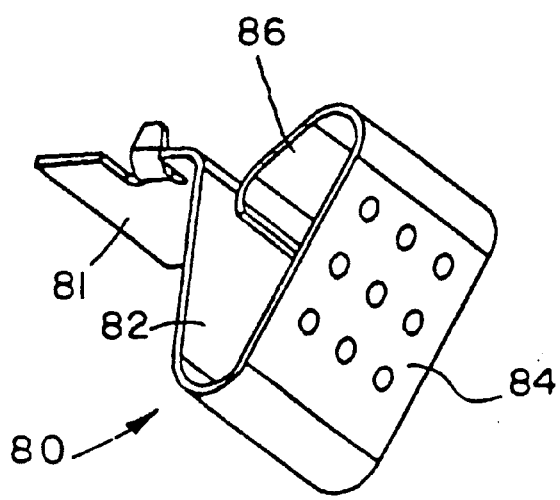
FIGS. 12–13 illustrate enlarged perspective views of a detail of the instrument illustrated in FIG. 1.

A brass battery contact 74 (FIGS. 1 and 11) is press-fitted into a space provided at the back end of bottom portion 22. Contact 74 provides contacts to the opposite terminals of two, for example, 1.5 V, AAA size, dry cells 75 (FIG. 14) which provide power to instrument 20. To prevent the dry cells 75 from being connected backward in the circuit of instrument 20, a boss 76 is molded into bottom portion 22 around the opening 78 through which contact 74 makes contact with the + terminal of the dry cell in well 28a. The dry cell 75 in well 28a will not make contact to the circuit through opening 78 unless the dry cell is inserted in the correct orientation into well 28a. Spring battery contact clips 80 (FIGS. 1, 12 and 13) are provided at the opposite front ends of both battery wells 28a and b. Each spring battery contact clip 80 includes a base 81 mounted on the PCB 38.

Clip 80 turns downward from PCB 38 through a constant radius of illustratively 0.75 mm to a first leg 82 which extends downward from PCB 38 at an angle of between about five degrees and about ten degrees with respect to a line perpendicular to the base portion 81, illustratively about 8°. Clips 80 then turn through a constant radius of illustratively about 1.12 mm and a battery-contacting leg 84 extends upward, defining between itself and a perpendicular to base 81 an angle of between about fifteen degrees and about twenty five degrees with respect to the perpendicular, illustratively about 20°. Clips 80 then turn through a constant radius of illustratively about 1 mm and a leg 86 extends downward at an angle of between about forty degrees and about fifty degrees with respect to the perpendicular, illustratively about 45°. Clips 80 then turn at a constant radius of illustratively about 0.75 mm and continue downward to terminate. The total height of clips 80 is about 8.8 mm. This construction reduces the possibility that the clips 80 themselves will be damaged in the event a user drops the instrument 20. Clips 80 illustratively are constructed from half hardened BeCu 190 alloy with a 60/40 tin/lead plating to resist corrosion and ease solder connections.

A lens 90 (FIG. 1) covers the opening 92 in top portion 24 over LCD 42. Lens 90 is constructed from polycarbonate resin with a self-healing polyurethane coating to reduce the degradation of the lens 90's transparency owing to marring of the lens 90 which would otherwise inevitably result from use. A lens constructed from polycarbonate resin with a conventional hard coating to reduce marring may also be used.

Top portion 24 includes a slot 94 in its front through which biosensor strips 21 are inserted to initiate tests to determine, inter alia, glucose concentration of blood samples. The strips 21 include, for example, two conductor metallizations extending longitudinally of the strips 21 through which electrical contact is made between the strips' chemistries and the circuitry of the instrument 20. A socket 96 through which this contact is made is mounted directly behind slot 94 on PCB 38. Because the slot 94 and socket 96 are provided on separate components of the instrument, 20, namely, the top portion 24 and PCB 38, respectively, some manufacturing tolerance-induced variation in the relative positions of slot 94 and socket 96 is inevitable. Some side-to-side variation is accounted for by ribs 97 (FIG. 7) which extend inward toward the location of socket 96 in the assembled instrument 20. The lower inside regions 99 of ribs 97 are angled slightly away from each other to help guide the components of instrument 20 into their designed locations during assembly. Additional accommodation of tolerance-induced variation is provided by the width of the slot 94, the width of the socket 96 and the widths of the electrical conductor metallizations on the strips 21. Up-and-down tolerance variations are accounted for in part by a pair of spring arms 98 molded into bottom portion 22. Spring arms 98 include upwardly converging somewhat arcuate resilient portions 100 and uppermost contact pads 102 which contact the underside of socket 96 in the assembled instrument 20. Arms 98 help absorb tolerance variations in the up-and-down position of socket 96 with respect to slot 94, urging socket 96 gently upward in those instances in which it is at the low point of its assembly tolerance so that strips 21 will slide easily through slot 94 into and from socket 96. Arms 98 also stabilize the front portion of PCB 38 against shock caused by incidental jarring of the instrument 20 during use.

Turning now to FIGS. 14 and 15a–h, the electric circuit of the instrument 20 includes a microcontroller (μC) 110 (FIG. 14 and FIG. 15c) and an application-specific integrated circuit (ASIC) 112 (FIG. 14 and FIG. 15*a*), as well as other discrete and integrated circuit components. In the description that follows, specific discrete and integrated circuit components, and in many instances, specific sources of these components, will be identified. The circuit will be described with reference to those specifically identified components, sometimes referring to terminals by terminal names and numbers and/or pin numbers. This should not be interpreted to mean that these are the only components available from the identified sources or any sources which will perform the necessary functions in the circuit. Indeed, typically there will be a number of suitable discrete and integrated circuit components available from the identified sources and other sources which will perform the necessary functions. Some of such substitute components will use the same terminal/pin identifiers as those noted in this description. Others, however, will use different designations.

Figure 14:
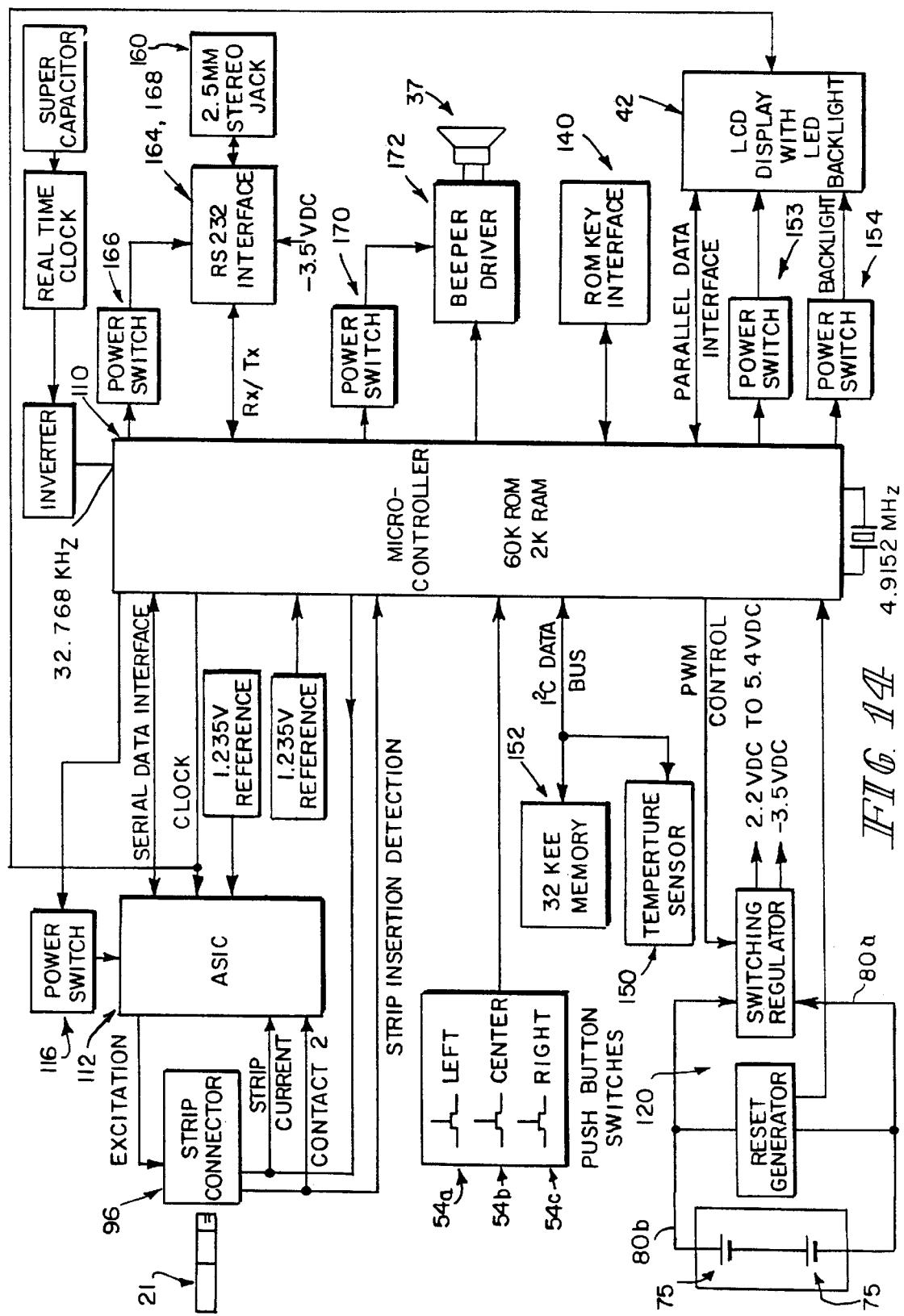
FIG. 14 illustrates a block diagram of an electric circuit useful in an instrument constructed according to the invention.
Figure 15A:
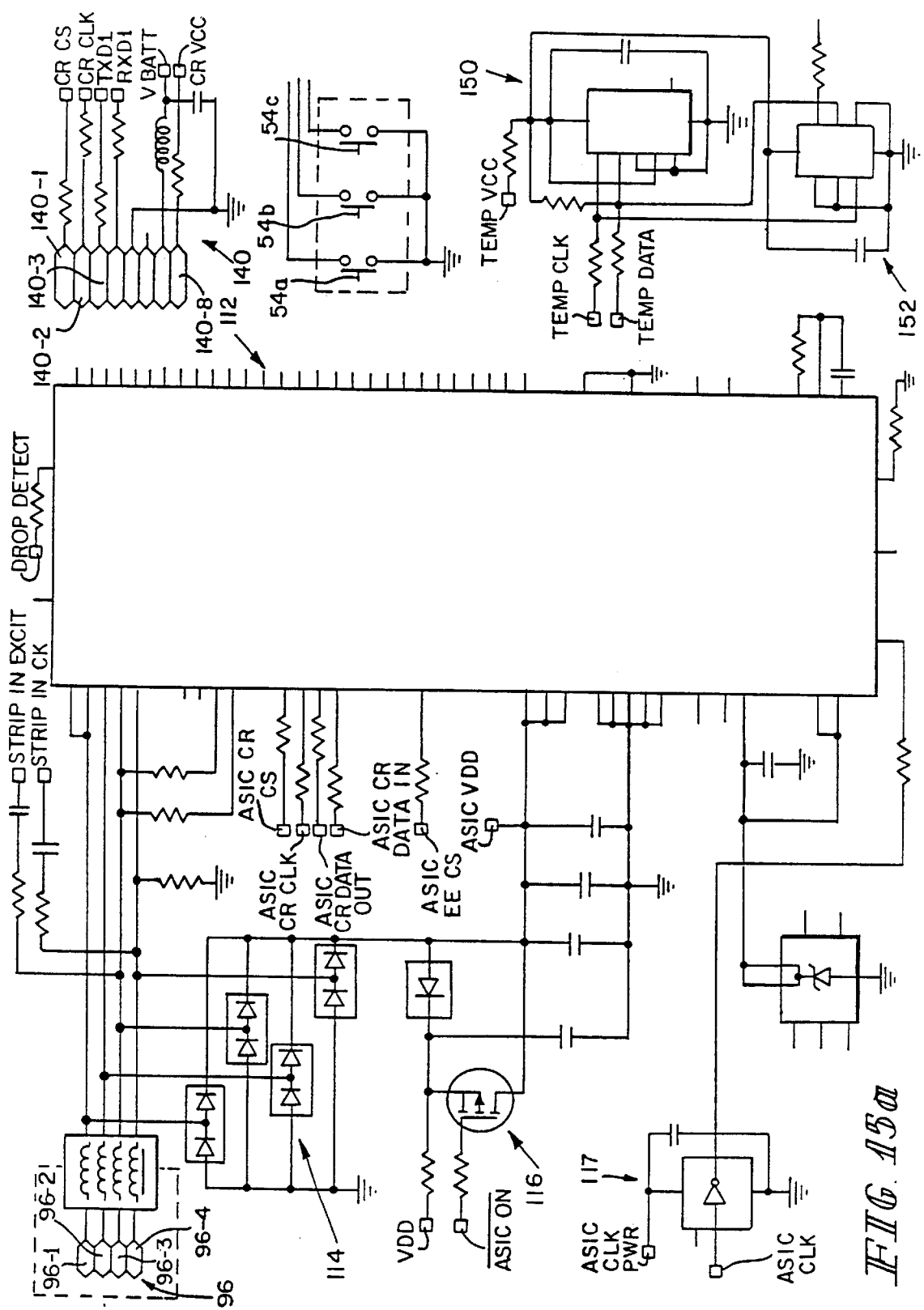
FIGS. 15a–h illustrate partly block and partly schematic diagrams of the electric circuit illustrated in block diagram form in FIG. 14.

Referring now particularly to FIG. 14 and FIG. 15*a*, socket 96 is illustrated as including four terminals 96-1–96-4 which are coupled through an EMI filter to the SENSOR EXCITing, SENSOR FeedBack, SENSOR INput, and CONTACT 2 INput terminals, respectively, of ASIC 112. These terminals are all constrained to be ≧−0.6 V and ≦ASIC VDD+0.6 V by respective diodes 114. ASIC VDD is provided from the system VDD supply through a 39 Ω resistor and the source and drain of an FET 116. FET 116 illustratively is a type BSS84 FET. Terminals 96-3 and -4 are also coupled through respective series 10 KΩ resistors and 1 μF capacitors to form the STRIP IN EXCITe and STRIP IN ChecK terminals of the instrument 20. These terminals are used by the instrument 20's operating system to turn the instrument 20 on in response to the insertion into slot 94 of a biosensor strip. Terminal 96-3 is also coupled through a 4.99 KΩ resistor to the CALibrate Resistance EXCITe terminal of ASIC 112, and through a 7.5 KΩ resistor to the IV AMPlifier FeedBack terminal of ASIC 112. Terminal 96-4 is also coupled through a 49.9 KΩ resistor to ground. Instrument 20'sASIC CLocK PoWeR is coupled to the power supply terminal of an inverter 117. The input terminal of inverter 117 is coupled to instrument 20's ASIC CLocK terminal. The output terminal of inverter 117 is coupled through a 100 Ω resistor to ASIC 112's XIN terminal. The ASIC clock frequency of 153.6 KHz is a submultiple (1/32) of the system clock frequency (4.9152 MHz) and is derived from the system clock. Inverter 117 illustratively is a type TC7SHU04 inverter. The TEMPerature SIGnal INput terminal of ASIC 112 is held at a 1.235 V voltage reference level by, for example, an LT 1004-1.235 voltage reference IC. ASIC 112 illustratively is the same type ASIC as is used in the Accu-Chek® Advantage® (instrument available from Boehringer Mannheim Corporation, 9115 Hague Road, Indianapolis, Ind. 46250-0457.

Figure 15B:
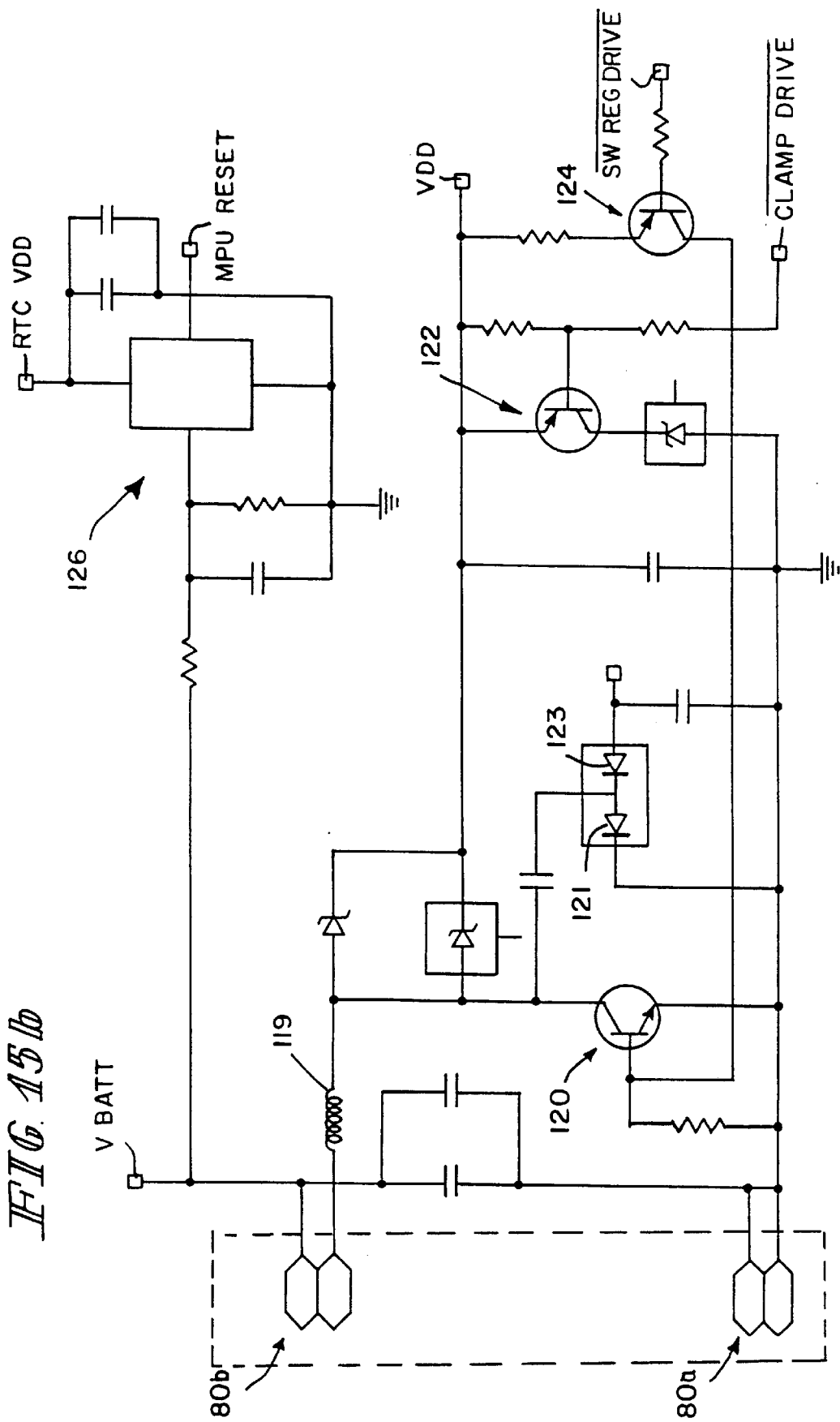
Figure 15C:
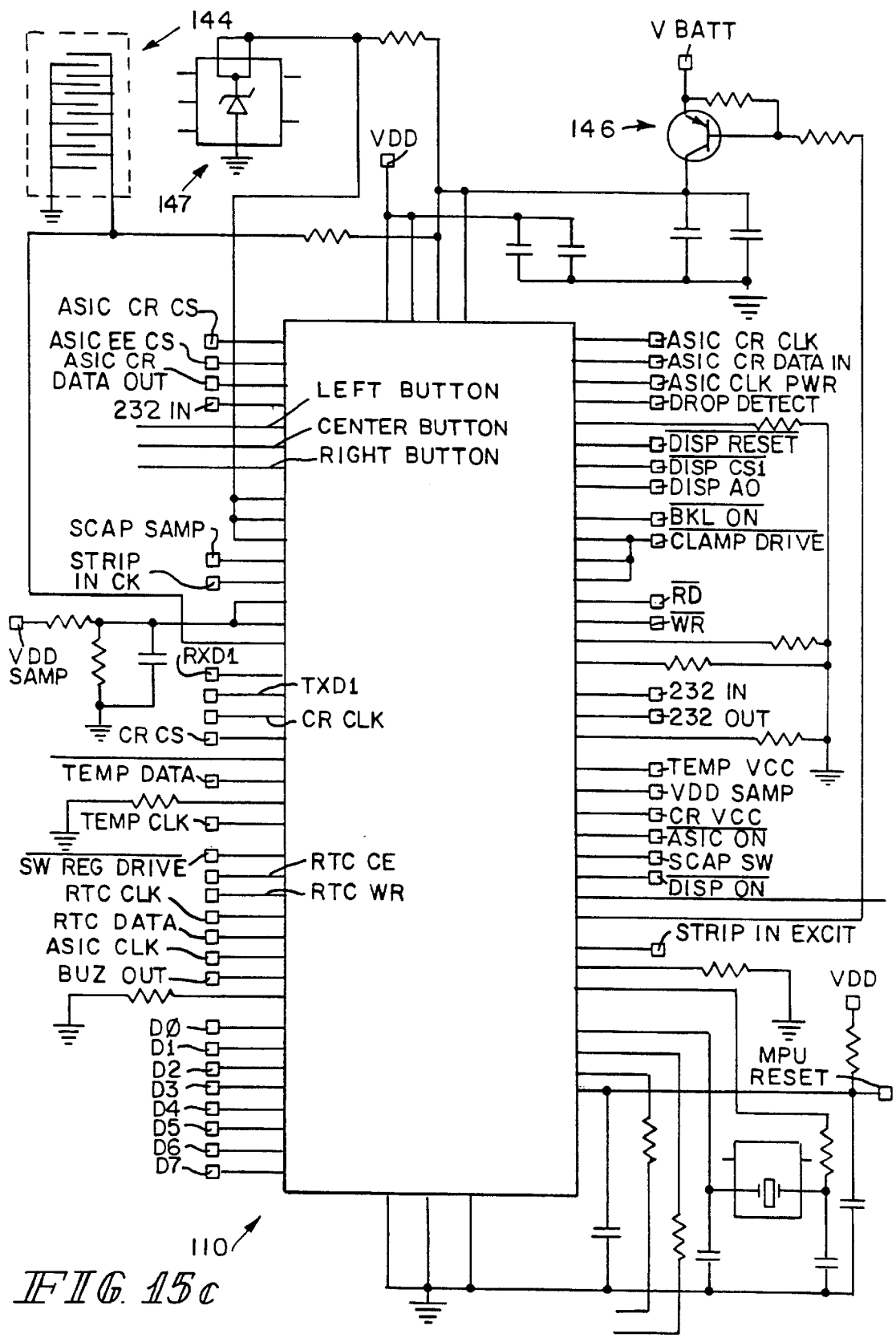

Referring now to FIG. 14 and FIG. 15*b*, the battery+ connector 80*b*, which forms instrument 20's V BATT terminal, is coupled through a 470 μH inductor 119 to the collector of a switching regulator transistor 120. The emitter of transistor 120 is coupled to battery—connector 80*a*, the instrument 20 ground. The base of transistor 120 is coupled through a 20 KΩ resistor to ground. As a second function, the collector of transistor 120 is coupled to an inverter and multiplier comprising a diode 121, the anode of which is coupled through a 0.33 μF capacitor to the collector of transistor 120 and the cathode of which is coupled to ground, and a diode 123, the cathode of which is coupled to the anode of diode 121 and the anode of which is coupled through a 0.33 μF capacitor to ground and forms the instrument 20'snotVEE terminal. This terminal nominally runs at about −3.5 VDC. Terminal 80*b* is also coupled through inductor 119 and the parallel combination of a 5.1 V Zener diode and a Schottky diode to form the VDD terminal of instrument 20. A 10 μF capacitor is coupled across VDD and ground. Transistor 120 switching of VBATT through inductor 119 permits VDD to run nominally at about 5.1 VDC. The emitter of a transistor 122 is coupled to VDD. Its collector is coupled through a 5.1 V Zener diode to ground. Its base is coupled through a 20 KΩ resistor to VDD and through a 2 KΩ resistor to the instrument 20's notCLAMP DRIVE terminal. The emitter of a transistor 124 is coupled through a 2 KΩ resistor to VDD. Its collector is coupled to the base of transistor 120. The base of transistor 124 is coupled through a 20 KΩ resistor to instrument 20's notSWitching REGulator DRIVE terminal to drive transistor 120 with a pulsewidth modulated waveform to regulate the power supply voltages. The PWM pulse repetition frequency is a submultiple (1/128) of the system clock frequency (4.9152 MHz) and is derived from the system clock to minimize the possibility of beat frequencies which could deleteriously affect the performance of instrument 20. The voltage is monitored by monitoring VDD and VBATT voltages through the μC 110 A/D port. The pulse width is modulated by μC 110 in a closed loop control strategy to maintain the desired voltage. Transistor 120 illustratively is a type 2N3904 transistor. Transistors 122 and 124 illustratively are type MMBT 3906 transistors.

Terminal 80*b* is also coupled through a 2 MΩ resistor to the INput terminal of a voltage monitor IC 126. The OUTput terminal of IC 126 forms the instrument 20's μC 110 notRESET terminal. The VCC and GrouND terminals of IC 126 are coupled across the instrument 20's Real Time Clock VDD and ground terminals. A parallel RC circuit including a 0.1 μF capacitor and a 2.74 MΩ resistor is coupled across the IN and GND terminals of IC 126. IC 126 illustratively is a type MAX836 voltage monitor IC.

Figure 15D:
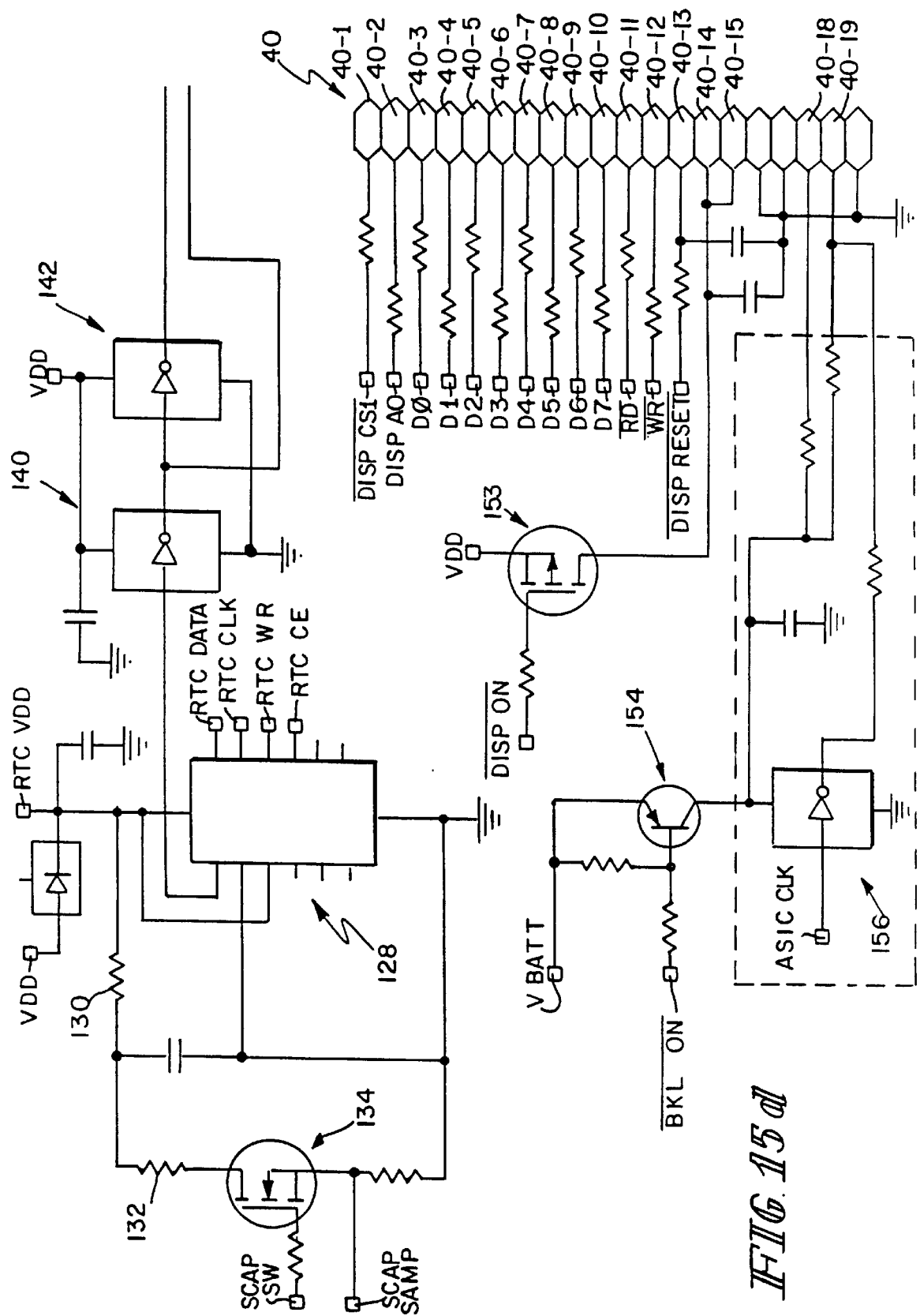

Referring now to FIG. 14 and FIG. 15*d*, the instrument 20's real time clock includes a real time clock IC 128 whose VDD and GrouND terminals are coupled across RTC VDD and ground. RTC VDD is coupled to IC 128's Frequency Output Enable terminal. The Frequency SELect terminal of IC 128 is coupled to ground. The series string of a 1 KΩ resistor 130, a 100 KΩ resistor 132, the drain of an FET 134, the source of FET 134 and a 20 KΩ resistor is coupled between RTC VDD and ground. The instrument 120's SuperCAPacitor SAMPle terminal is coupled to the source of FET 134. The instrument 20's SuperCAPacitor SWitch terminal is coupled through a 100 KΩ resistor to the gate of FET 134. This configuration permits the charge state of a 0.047 μF capacitor 137 coupled between the junction of resistors 130, 132 and ground to be managed. The voltage across capacitor 137 is measured whenever the instrument 20 is awakened to check for a strip insertion to verify that a minimum voltage level is present by turning on the resistor 130, 132 voltage divider network. If this voltage level drops below the required level, the switching regulator of FIG. 15*b* is maintained on until the next strip insertion check. This strategy is implemented because the reset generator 126 and the real time clock 128 require a minimum supply voltage of 2.5 VDC, while the battery voltage may go as low as 2.2 VDC in a working instrument 20. The DATA, ClocK, WRite, and Chip Enable terminals of IC 128 form instrument 20's RTC DATA, RTC CLK, RTC WR, and RTC CE terminals, respectively. The Frequency OUT terminal of IC 128 is coupled through series inverting amplifiers 140, 142 and a 100 Ω resistor to the XT2 terminal of μC 110. The output terminal of inverter 140 is coupled through a 100 Ω resistor to the XT1 terminal of μC 110. IC 128 illustratively is an Epson type RTC4543SA 32 KHz real time clock IC.

Referring back to FIG. 15a, instrument 20 includes a port 140 for receiving a key which carries a ROM containing, ititer alia, lot-specific parameters for the biosensor strips 21 currently in use in the instrument 20. Port 140 includes terminals 140-1–140-8. Terminals 140-1–140-4 and 140-8 are coupled through respective 100 Ω resistors to the instrument 20's Code ROM CS terminal, CR ClocK terminal, TXD1 terminal, RXD1 terminal and CR VCC terminal, respectively. Terminal 140-7 is coupled through a ferrite bead to V BATT. Terminal 140-5 is coupled to instrument 20 ground. The purposes and functions of such code ROM keys are explained further in U.S. Pat. No. 5,053,199. The code ROM on the key which port 140 is adapted to receive illustratively is a National Semiconductor type NMC93C56 or C66 ROM.

Keys 54-a–c are coupled to μC 110's ports 04–06, respectively (FIG. 14c). Ports 00–03 form instrument 20's ASIC Code ROM Chip Select, ASIC EEPROM Chip Select, ASIC CR DATA OUT and 232 IN terminals, respectively. Interleaved conductor patterns 144 form instrument 20's humidity sensor. One set of these interleaved patterns 144 is coupled to ground. The other set is coupled to the μC 110's port 17 and through a 100 KΩ resistor to μC 110's analog reference input at the collector of a transistor 146. The emitter of transistor 146 is coupled to V BATT. The base of transistor 146 is coupled through a 20 KΩ resistor to V BATT and through a 20 KΩ resistor to μC 110's port 127. V BATT operating potential, stepped down by a 100 KΩ resistor to a 1.2 V voltage reference 147, is coupled to ports 10–12 of μC 110. Ports 13 and 14 of μC 110 form the SCAP SAMP and STRIP IN CK terminals, respectively of instrument 20. Ports 15 and 16 are coupled through a 100 KΩ resistor to instrument 20's VDD SAMPle terminal. Ports 20–23 form the instrument 20's RXD1, TXD1, CR CLK and CR CS terminals, respectively. μC 110 illustratively is an NEC μPD78P058 eight-bit microcontroller. Transistor 146 illustratively is a type MMBT3906 transistor.

The interior of instrument 20 is fairly crowded. As a result, some heating effects result when instrument 20 is operated in certain of its modes over extended times. The chemistries which reside on typical biosensor strips 21 are somewhat temperature dependent. Prior art instrument designs have taken this into consideration by providing temperature sensors and algorithms which adjust their biosensor strip outputs for ambient temperature. However, further temperature correction has been found advantageous in instrument 20. Specifically, it has been found that, as instrument 20 operates in certain modes, heat builds up in the instrument. This results in a difference between ambient temperature, that is, the temperature of strip 21 and the temperature against which the reaction of the chemistry on strip 21 must be compensated to provide an accurate glucose concentration reading, and the temperature measured by the thermometer mounted on PCB 38 inside the instrument 20. μC 110 uses an algorithm which takes into account how long instrument 20 has been operating in each of its several different heat-evolving modes since it was last turned on to calculate how much adjustment to an indicated ambient temperature is appropriate in order to provide a more accurate calculated glucose concentration. Amounts of adjustment for heat buildup in instrument 20 range from 0 to about 2.5% or so. The algorithm will be explained in detail later. The temperature sensor itself includes a digital thermometer IC 150 (FIG. 14 and FIG. 15a). An illustrative digital thermometer is the Dallas Semiconductor DS1621C IC. Instrument 20's TEMPerature ClocK and TEMPerature DATA terminals are coupled through respective 100 Ω resistors to the SCL and SDA terminals, respectively, of the digital thermometer 150. The SCL and SDA terminals of digital thermometer 150 are also coupled to the SCL and SDA terminals, respectively, of a serial EEPROM IC 152. Serial EEPROM 152 illustratively is an Atmel type AT24C256 serial EEPROM IC. The WP terminal of serial EEPROM 152 is coupled through a 100 Ω resistor to port 24 of μC 110. Power is supplied to ICs 150, 152 from instrument 20's TEMPerature VCC terminal through a 100 Ω resistor. A 10 KΩ resistor is coupled between the VDD and SDA terminals of IC 150. In this configuration, the digital thermometer 150 and EEPROM 152 are time-division multiplexed onto the same bus into μC 110.

Referring back to FIG. 14 and FIG. 15c, ports 25 and 27 of μC 110 form instrument 20's TEMP DATA and TEMP CLK terminals, respectively. Ports 30–36 form instrument 20's notSW REG DRIVE, RTC CE, RTC WR, RTC CLK, RTC DATA, ASIC CLK and piezoelectric BUZzer OUTput terminals, respectively. Ports 40–47 form instrument 20's Display 0–Display 7 terminals, respectively. Referring to FIG. 14 and FIG. 15d, terminals D0–D7 are coupled through respective 100 Ω resistors to terminals 40-3–40-10, respectively, of socket 40. The notDISPlay Chip Select1, DISPlay A0, notReaD, notWRite and notDISPlay RESET terminals of instrument 20 are coupled through respective 100 Ω resistors to terminals 40-1, 40-2, 40-11, 40-12 and 40-13, respectively, of socket 40. Display 42 is powered through an FET 153, the source of which is coupled to VDD and the drain of which is coupled to the power supply terminals 40-14 and -15 of socket 40. The gate of FET 153 is coupled through a 100 KΩ resistor to the instrument 20's notDISPlay ON terminal. Display 42 may be backlit to ease reading of it. The notBacKLight ON terminal of instrument 20 is coupled through a 2 KΩ resistor to the base of a transistor 154. The emitter of transistor 154 is coupled to V BATT. V BATT is coupled through a 2 KΩ resistor to the base of transistor 154. The collector of transistor 154 is coupled to the power supply terminal of an inverter 156. The input terminal of inverter 156 is coupled to instrument 20's ASIC CLK terminal. The collector of transistor 154 is coupled through respective 100 Ω resistors to terminals 40-18 and 40-19 of socket 40. The output terminal of inverter 156 is coupled through a 100 Ω resistor to terminal 40-19 of socket 40. FET 153 illustratively is a type BSS84 FET, transistor 154 illustratively is a type MMBT3906 transistor, and inverter 156 illustratively is a type TC7SHU04 IC inverter.

Figure 15E:
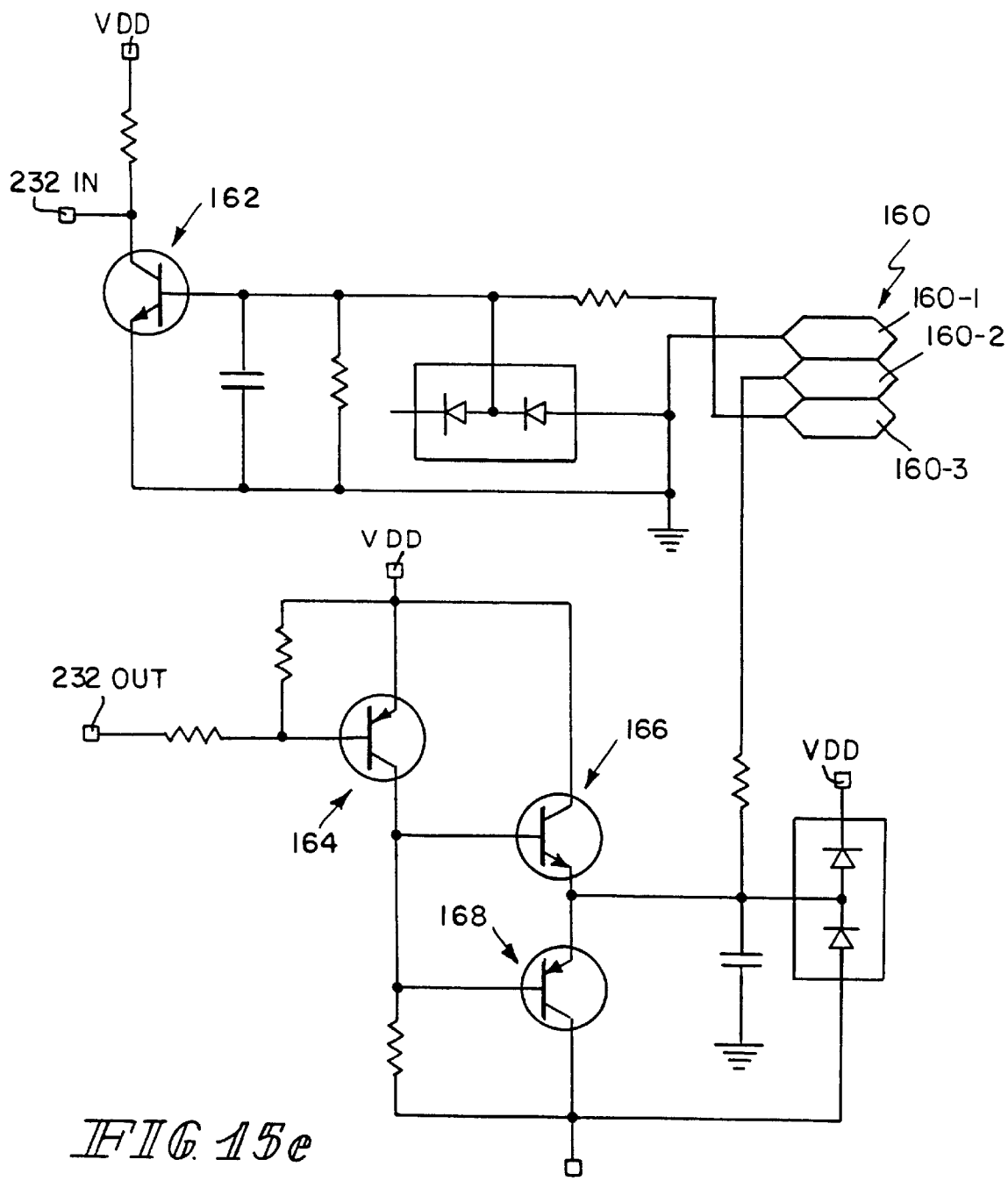
Figure 15F:
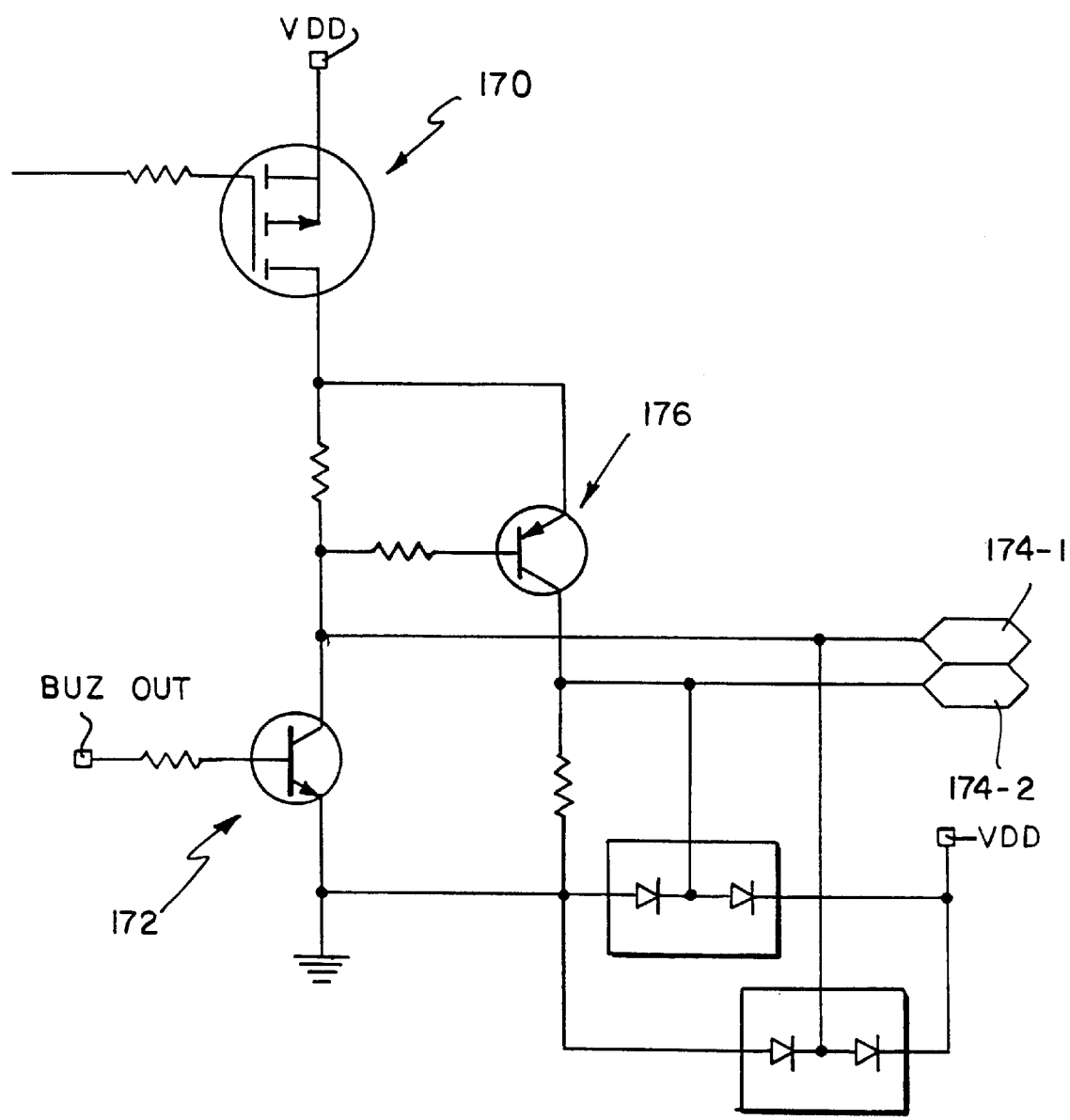
Figure 15G:
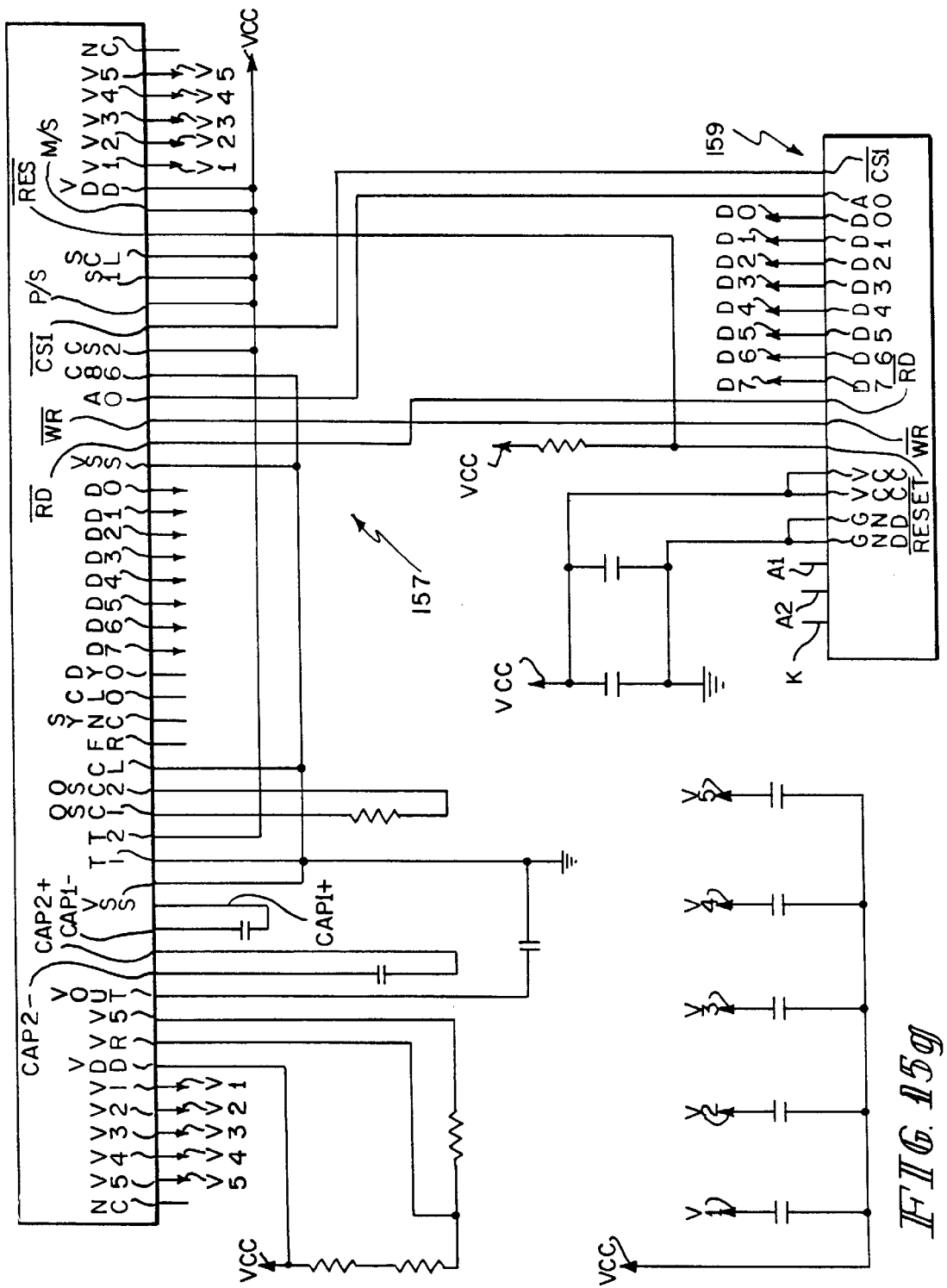
Figure 15H:
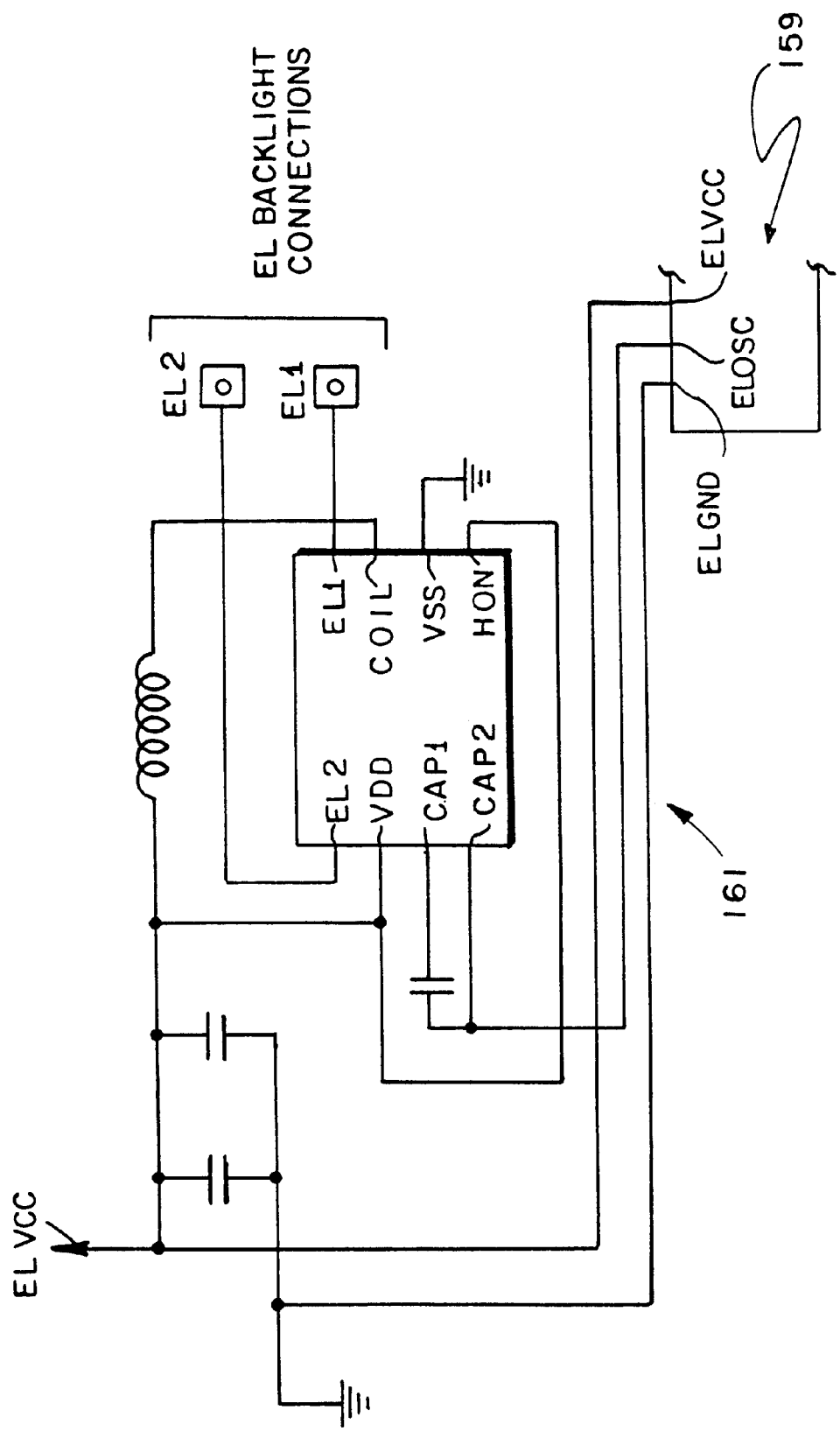

FIGS. 15g–h illustrate the LCD display module schematics. The display controller 157, which illustratively is a SMOS SED1560, includes two sets of terminals V1–V5, pins 6 and 46, 5 and 47, 4 and 48, 3 and 49, and 2 and 50, respectively, coupled through respective 1 μF, 16 V capacitors to $V_{CC}$. The $V_{DD}$, M/S, SCL, SI, P/S, CS2 and T2 terminals, pins 7, 8, 10, 11, 12, 14 and 35, respectively, of display controller 157 are coupled to $V_{CC}$. The C86, $V_{SS}$, CLear, and T1 terminals, pins 15, 19 and 37, 32, and 36, respectively of display controller 157 are coupled to ground. The D0–D7 terminals, pins 20–27, respectively, of display controller 157 are coupled to the system D0–D7 lines. The OSC1 and OSC2 terminals, pins 34 and 33, are coupled together through a 1MΩ, 1% resistor. The CAP1+ and CAP1− terminals, pins 38 and 39, are coupled together through a 1 μF, 16 V capacitor. The CAP2+ and CAP2− terminals, pins 40 and 41, are coupled together through a 1 μF, 16 V capacitor. The VOUT terminal, pin 42, is coupled to ground through a 2.2 µF, 16 V capacitor. The V5 terminal, pin 43, is coupled through series 340 KΩ, 1% and 47 KΩ resistors to the VR terminal, pin 44, of display controller 157. The VR terminal is also coupled through a 102 KΩ, 1% resistor to $V_{CC}$. The $V_{DD}$ terminal, pin 45, is coupled to $V_{CC}$. Pins 1–13 of a connector 159 provide access to the not CS1, A0, D0–D7, notReaD, notWRite, and notRESet terminals, pins 13, 16, 20–27,11, 12, and 13, respectively, of display controller 157. $V_{CC}$ is coupled to pins 14 and 15 of connector 159. Ground is coupled to pins 16 and 17 of connector 159. Pins 18–20 of connector 159 are reserved for LED backlight connections for display 42. This permits two LED backlight anode connections, A1 and A2, to a common LED cathode return, K. Pins 1–20 of connector 159 are coupled to terminals 40-1–40-20, respectively. Alternatively, pins 18–20 of connector 159 can be used to drive an electroluminescent (EL) backlight, as illustrated in FIG. 15*h*. In this alternative embodiment, pin 18 of connector 159 forms the EL $V_{CC}$ terminal and pin 20 forms the EL $V_{CC}$ ground terminal. Parallel 0.01 µF and 4.7 µF bypass capacitors are coupled across pins 18 and 20. Pin 19 is coupled to the CAPacitor2 terminal of an EL backlight driver IC 161, such as, for example, a SIPEX SP4422ACN IC. A 150 pF capacitor may optionally be coupled across the CAP2 and CAP1 terminals of driver 161 to cause it to operate at a frequency other than the ELOSC frequency appearing at pin 19. The HON and $V_{DD}$ terminals of driver 161 are coupled to EL $V_{CC}$. The COIL terminal of driver 161 is coupled through an inductor, for example, a 9 mH shielded inductor, to EL $V_{CC}$. The $V_{SS}$ terminal of driver 161 is coupled to EL $V_{CC}$ ground. The EL backlight can then be coupled across the EL1 and EL2 terminals of driver 161.

Referring now to FIG. 14 and FIG. 15*e*, instrument 20 includes an RS232 I/O port 160 including terminals 160-1–160-3. Terminal 160-1 is coupled to ground. Terminal 160-3, instrument 20's RS232 port receive terminal, is coupled through a 20 KΩ resistor to the base of a transistor 162. A parallel RC circuit including a 0.001 µF capacitor and a 100 KΩ resistor is coupled between the base of transistor 162 and ground. The emitter of transistor 162 is coupled to ground. Its collector forms instrument 20's 232 INput terminal. Its collector is coupled through a 20 KΩ load resistor to VDD. Instrument 20's 232 OUTput terminal is coupled through a 20 KΩ resistor to the base of a transistor 164. The emitter of transistor is coupled to VDD. The collector of transistor 164 is coupled to the bases of a transistor 166 and a transistor 168. The emitters of transistors 166, 168 are joined. The collector of transistor 166 is coupled to VDD and the collector of transistor 168 is coupled to instrument 20's notVEE terminal. The joined emitters of transistors 166, 168 are coupled through a 100 Ω resistor to terminal 160-2, instrument 20's RS232 port transmit terminal. A 20 KΩ pull-up resistor is coupled between VDD and the base of transistor 164. A 10 KΩ pull-down resistor is coupled between the base of transistor 168 and notVEE. Transistors 164, 168 illustratively are type MMBT3906 transistors. Transistors 162, 166 illustratively are type 2N3904 transistors.

Referring back to FIG. 15*c*, ports 50–53 of µC 110 form instrument 20's ASIC CR CLK, ASIC CR DATA IN, ASIC CLK PWR and DROP DETECT terminals, respectively. Ports 55–57 and 60 form instrument 20's notDISPlay RESET, notDISPlay Chip Select1, DISPlay A0, and notBacKLight ON terminals, respectively. Instrument 20's notCLAMP DRIVE terminal is formed by ports 61–63 of µC 110. Ports 64 and 65 of µC 110 form instrument 20's notReaD and notWRite terminals. Ports 70 and 71 of µC 110 are coupled to instrument 20's 232 IN and 232 OUT terminals, respectively. Ports 120–125 form instrument 20's TEMP VCC, VDD SAMP, CR VCC, notASIC ON, SCAP SW and notDISP ON terminals, respectively.

Referring now to FIG. 14 and FIG. 15*f*, port 126 of µC 110 is coupled through a 100 KΩ resistor to the gate of an FET 170. The source of FET 170 is coupled to VDD. The drain of FET 170 is coupled through a 1 KΩ resistor to the collector of a transistor 172. The emitter of transistor 172 is coupled to ground. The base of transistor 172 is coupled through a 20 KΩ resistor to instrument 20's piezoelectric BUZzer OUTput terminal. The collector of transistor 172 forms one, 174-1, of the buzzer 37 output terminals. The emitter of a transistor 176 is coupled to the drain of FET 170. The collector of transistor 176 is coupled through a 1 KΩ resistor to ground. The base of transistor 176 is coupled through a 20 KΩ resistor to the collector of transistor 172. The collector of transistor 176 forms the other buzzer 37 output terminal 174-2. Terminals 174-1 and -2 are clamped $\geq$ −6 V and $\leq$ VDD +0.6 V. FET 170 illustratively is a type BSS84 FET. Transistor 172 illustratively is a type 2N3904. Transistor 176 illustratively is a type MMBT3906.

Referring back to FIG. 15*c*, port 130 of µC 110 forms the STRIP IN EXCIT terminal of instrument 20. A 4.9152 MHz crystal clock is coupled across ports X1–X2 of µC 110. The notRESET port of µC 110 forms instrument 20's MPU RESET terminal and is coupled through a 10 KΩ resistor to VDD.

Returning to the instrument 20's internal heating algorithm, the internal heating can be described by a first-order differential equation, $$\tau(dv/dt)+v=T(\text{Temp., Pwr.}) \tag{1}$$

in which $\tau$ is a heating/cooling time constant which is determined empirically and varies depending upon the internal geometry of the instrument 20 and other factors, v is the correction value, dv/dt is the rate of change of the correction value with respect to time, and T(Temp., Pwr.) is the steady state difference between ambient temperature outside the meter (that is, the temperature of the strips 21 and the chemistries on those strips) and the temperature inside the instrument 20 as reported by digital thermometer 150. Equation 1 can be represented as a difference equation:

$$v(t+\Delta t)=v(t)-(\Delta t/\tau)*v(t)+(\Delta t/\tau)*T(\text{Temp., Pwr.}). \tag{2}$$

For the illustrated instrument 20, $\tau$(heating) is 20 minutes, $\tau$(cooling) is 15 minutes, $\Delta t$(cooling) is 2 seconds, $\Delta t$(heating) is 1 second, T(Temp., Pwr.) with the instrument 20 in its "sleep" state is 0 (since the temperature differential between the ambient temperature and the digital thermometer 150's indicated temperature approaches 0 with increasing time in the sleep state), and T(Temp., Pwr.) in each of the instrument 20's active, heat-evolving states is stored in a look-up table in EEPROM 152. Equation 2 is scaled as illustrated in equation 3. Equation 3 is implemented in instrument 20's firmware to calculate the correction factor:

$$v(t+\Delta t)*25600=v(t)*25600+\{-[(\Delta t/\tau)*131072]*[v(t)*25600]/32768+[(\Delta t/\tau)*T(\text{Temp., Pwr.})*102400]\}/4 \tag{3}$$

Values for T(Temp., Pwr.) are stored for each of three temperature ranges, namely: Temp. <20° C.; 20° C.$\leq$Temp. <30° C.; and Temp. $\geq$30° C.; and for each of four different power consumptions, namely: low power consumption (low clock speed with backlight off); low clock speed with backlight on; high clock speed with backlight off; and, high power consumption (high clock speed with backlight on). Useful meter internal temperature correction values can be determined from these values. For the illustrated instrument, useful T(Temp., Pwr.) values are listed in the following table. It should be understood, however, that these values will vary with the internal configuration and operating parameters of the instrument.

| Ambient Temperature | Power Level, P | | | |
|---|---|---|---|---|
| | low clock speed with backlight off | low clock speed with backlight on | high clock speed with backlight off | high clock speed with backlight on |
| <20° C. | 0 | 0.43 | 0.68 | 0.93 |
| 20° C. ≤ Temp. <30° C. | 0 | 0.60 | 0.68 | 0.93 |
| Temp. ≥ 30° C. | 0.28 | 0.73 | 0.68 | 0.93 |

Figure 16:
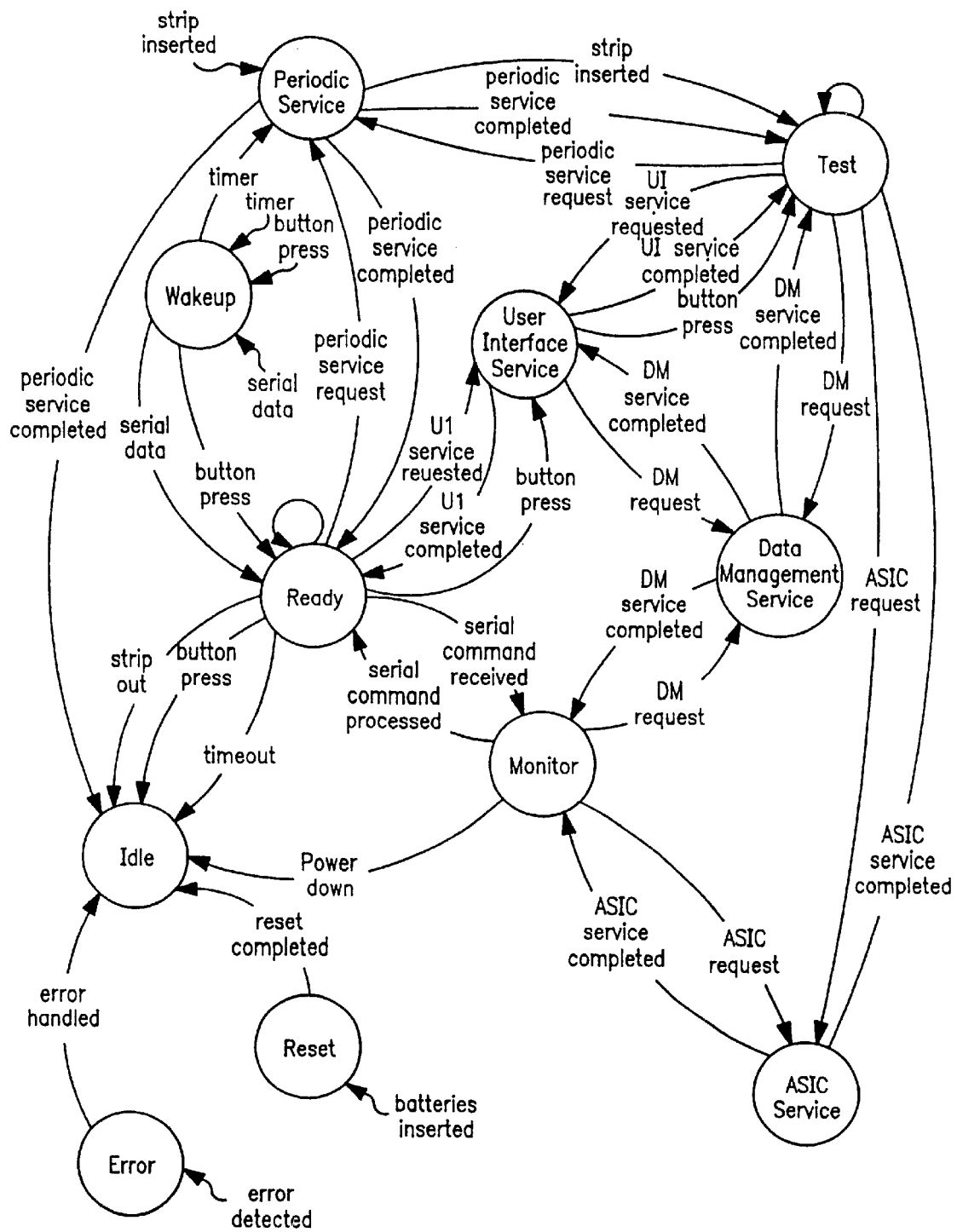
FIG. 16 illustrates a dynamic model of firmware useful in operating the instrument illustrated in FIG. 1.

FIG. 16 illustrates the dynamic model of the interaction of the firmware which is programmed into $\mu$C 110's internal ROM. The circles indicate the various states of $\mu$C 110. The firmware is primarily interrupt driven. To increase battery life when the $\mu$C 110 is not servicing an interrupt or processing pending events, $\mu$C 110 is maintained in an idle state. When the $\mu$C 110 is in idle state, the clock speed is lowered from 4.9152 MHz to 32 KHz. When the program monitor is in the wakeup state, it is determining what caused the wakeup interrupt. When it is in the monitor state, it is processing serial commands. When it is in the ready state, it is waiting for user input. When it is in the periodic service state, it is performing periodic tasks, such as checking for a strip insertion or updating the instrument 20's temperature history. When it is in ASIC service state, it is processing a request from the ASIC 112, such as a request for data from the EEPROM 152 or the ROM key interface 140, or receiving information from the ASIC 112. When in test state, it is performing a test, either a blood glucose determination, a control glucose determination, or a diagnostic using a check strip. In the reset state, it is performing a power on reset initialization. In the idle state, it is halted awaiting wakeup. In the error state, it is handling some type of system error. In the user interface service state, it is processing a reaction to a key 54 press. In the data management service state, it is retrieving or storing data.

Figure 17A:
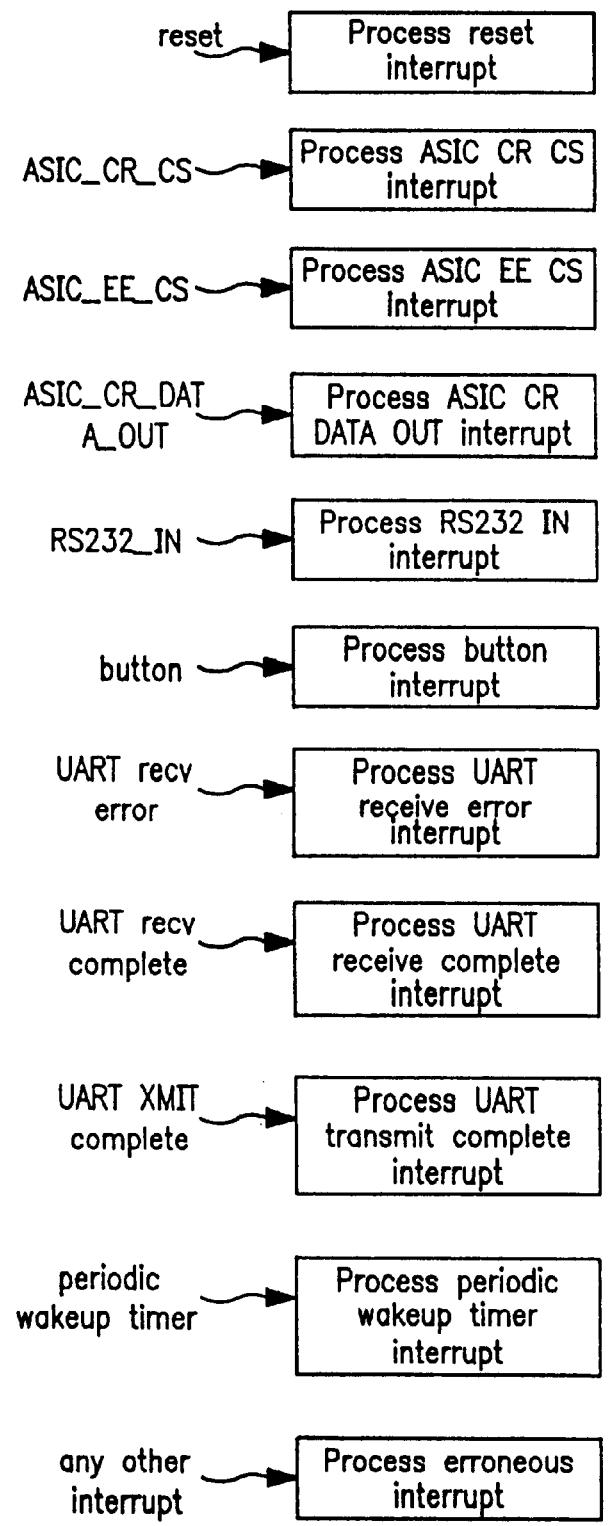
FIG. 17a illustrates the interrupt handling routines executed by firmware useful in operating the instrument illustrated in FIG. 1.

The various interrupts and the $\mu$C 110's responses to them are illustrated in FIG. 17a. The reset interrupt vectors to the reset state. The ASIC 112 Code ROM Chip Select interrupt handles ASIC code ROM 140 chip selects. The routine receives a code ROM 140 address from the ASIC, vectors to a routine to read the contents of the specified address, and sends the contents to the ASIC 112. This interrupt is only enabled when the ASIC 112 is on. This interrupt occurs when the instrument 20 is in the test state, or when the instrument 20 is in the monitor state and the pass through command has been issued.

The ASIC 112 EEPROM 152 Chip Select interrupt handles EEPROM 152 commands from ASIC 112. The routine receives a read command, an enable write command or a write command. The EEPROM read command reads an EEPROM address from the ASIC, retrieves the data from the $\mu$C 110 RAM (to which it has previously been transferred by the firmware), formats it, and sends it to the ASIC 112. The EEPROM enable write command reads the full command from the ASIC 112. The EEPROM write command gets an EEPROM 152 address and data from the ASIC 112 and stores this address and data in the $\mu$C 110's RAM. It should be noted that the EEPROM 152 contents are loaded into the $\mu$C 110's RAM before the ASIC 112 is powered up. The ASIC 112 EEPROM CS interrupt is only enabled when the ASIC is turned on. This interrupt occurs when the instrument 20 is in the test state, or when the meter is in the monitor state and the pass through command has been issued.

The process ASIC 112 code ROM 140 data output interrupt handles ASIC serial data that is received. This routine only processes data received from the ASIC 112 if the code ROM and EEPROM chip selects are not selected. This routine vectors to a routine to read the ASIC 112 data and store the received data in the $\mu$C 110's serial data buffer. This interrupt determines if the ASIC 112 has sent all expected data for the pending command, and if so, signals an appropriate event. This interrupt is only enabled when the ASIC 112 is turned on. This interrupt occurs when the insturment 20 is in the test state, or when the instrument is in the monitor state and the pass through command has been issued.

The process RS-232C data input interrupt wakes up the $\mu$C 110 when external data is input. This function sets the appropriate event to receive data via the $\mu$C 110's built-in Universal Asynchronous Receiver-Transmitter from the RS-232C port 160. This interrupt is only enabled when the instrument 20 is in the idle state.

The process button interrupt sets the appropriate event to handle a key 54a–c press. This interrupt is enabled when the instrument 20 is in the idle state, or when the instrument 20 is turned on and the display 42 prompts the user to make soft key 54 choices.

The process UART receive error interrupt handles UART errors. The error indicator is cleared and the UART is reset. The $\mu$C 110's serial I/O buffer is cleared. This interrupt is enabled except when the instrument 20 is in the idle state.

The process UART receive complete interrupt processes a byte received via the UART. Depending on the state of the $\mu$C 110, the firmware monitor state and the data received, the data may be stored in the $\mu$C 110's serial I/O buffer and/or may be echoed back to the sender. This interrupt is enabled except when the instrument 20 is in the idle state.

The process UART transmit complete interrupt sends data via the UART and manages the serial I/O buffer. This interrupt is enabled except when the instrument 20 is in the idle state.

The process periodic wake up timer interrupt causes the instrument 20 to wake from the idle state to check for a strip 21 insertion and/or to update the instrument 20's temperature history when appropriate. This interrupt is enabled when the instrument 20 is in the idle state.

The process erroneous interrupt should not be used. However, if it is, the user is notified if possible. The instrument 20 then sets an error state and is inoperable until the batteries 75 are removed from the instrument 20 and reinserted or replaced with new batteries to force a reset. This interrupt is always enabled.

Figure 17B:
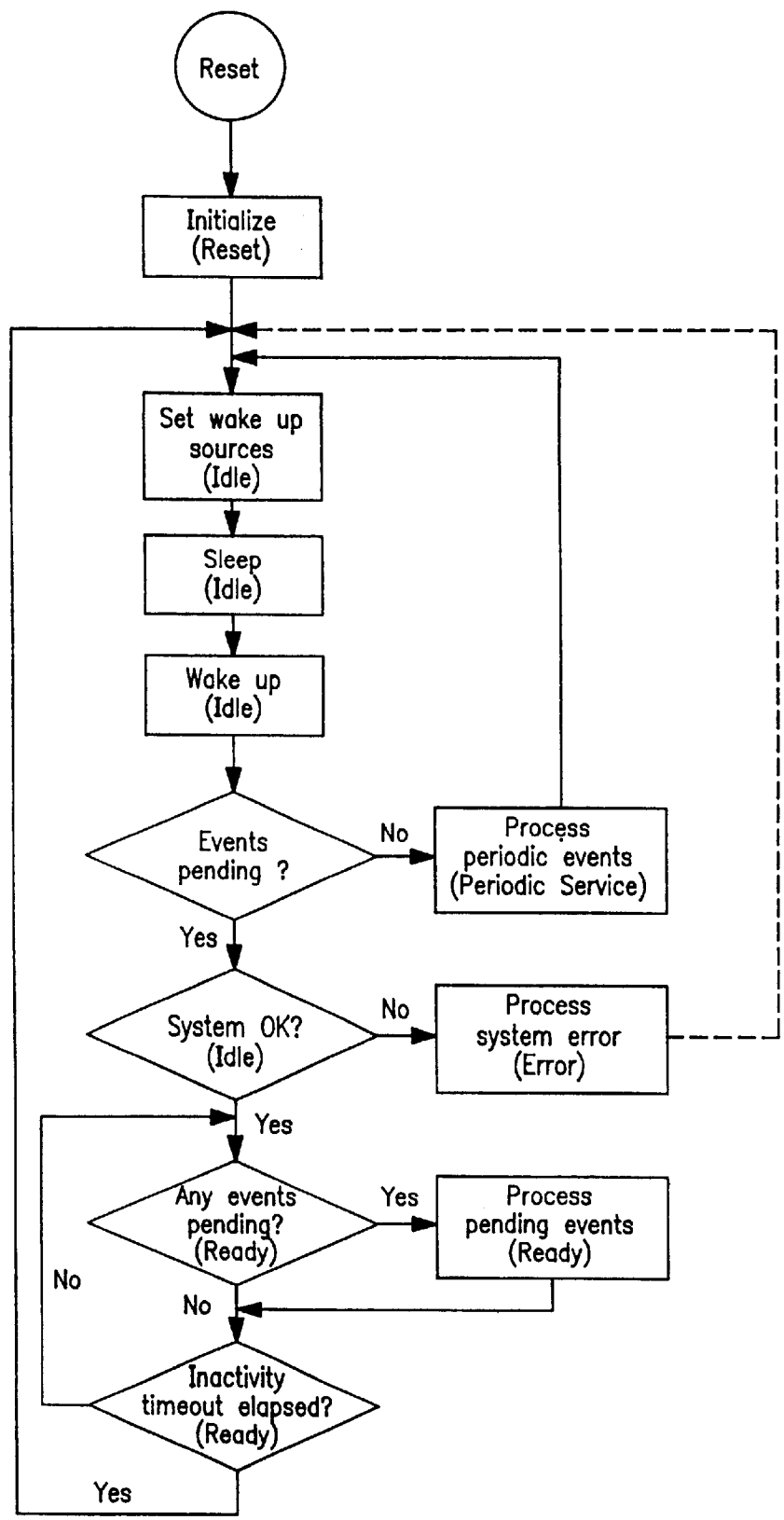
FIG. 17b illustrates a functional model of firmware useful in operating the instrument illustrated in FIG. 1.

The functional model of the firmware is illustrated in FIG. 17b. Power on reset is entered through the reset interrupt. States of the instrument 20 at the beginnings of the various functions are indicated in parentheses. The instrument 20 initializes itself by: initializing the stack pointer; resetting the $\mu$C 110 ports to the power up reset state; configuring the ports/resources for proper use; checking the battery level to be sure that it is sufficient for operation; setting the $\mu$C 110 terminals to the power up reset state; initializing the $\mu$C 110's RAM; initializing the instrument 20's components to power up steady state; initializing the instrument 20's power management system; loading the contents of EEPROM 152 into μC 110 RAM; incrementing a power up reset counter; initializing the instrument 20's temperature history; code ROM 140 cyclic redundancy checks, checking the manufacturing data flags to be sure that they are set, and checking the EEPROM 152 data (dynamic text, current language, etc.) to determine that it is correct; sending a power up reset complete acknowledgement; and, producing an audible beep on speaker 37 to indicate to the user that power up has been completed.

The set wake up sources function sets the port terminals and components to the power down terminal state and sets the interrupts for possible wake ups. The sleep function sets the clock to low clock speed and places the μC 110 in halt mode. The wake up function is initiated via interrupts to indicate what events require service. Appropriate event flags are set within the interrupt routines. The system OK ? function performs system level failsafes: the condensation sensor; SuperCAPacitor status; and, EEPROM 152 cyclic redundancy check (calibration, status, setup and insulin pump). This function also increments the power up counter, readies the instrument 20 for further processes by starting the main clock and resetting the stack pointer, and checks the battery level to be sure it is sufficient.

As previously noted, the process system error interrupt should never have to be used. However, if it is, the user is notified, if possible. Then the instrument 20 sets itself to an error state from which it is inoperable until the batteries are removed and reinserted or replaced with new batteries.

The any events pending? function determines if any events are pending and need to be handled. If no events are pending, the μC 110 monitors the PWM voltage and waits for a pending event or timeout. If the μC 110 is waiting for user input or serial input and the time to system timeout elapses, the μC 110 returns to idle state.

The process periodic events function checks whether there are any events that should be processed, such as: charging the SuperCAPacitor; performing a temperature sample; updating the temperature history; adjusting the internal self-heating variable; and, checking for a test strip 21 insertion.

The inactivity timeout elapsed? function operates while waiting for a button press or for serial data. This function determines if a timeout has occurred. If so, the μC 110 is put back into the idle state.

Figure 18:
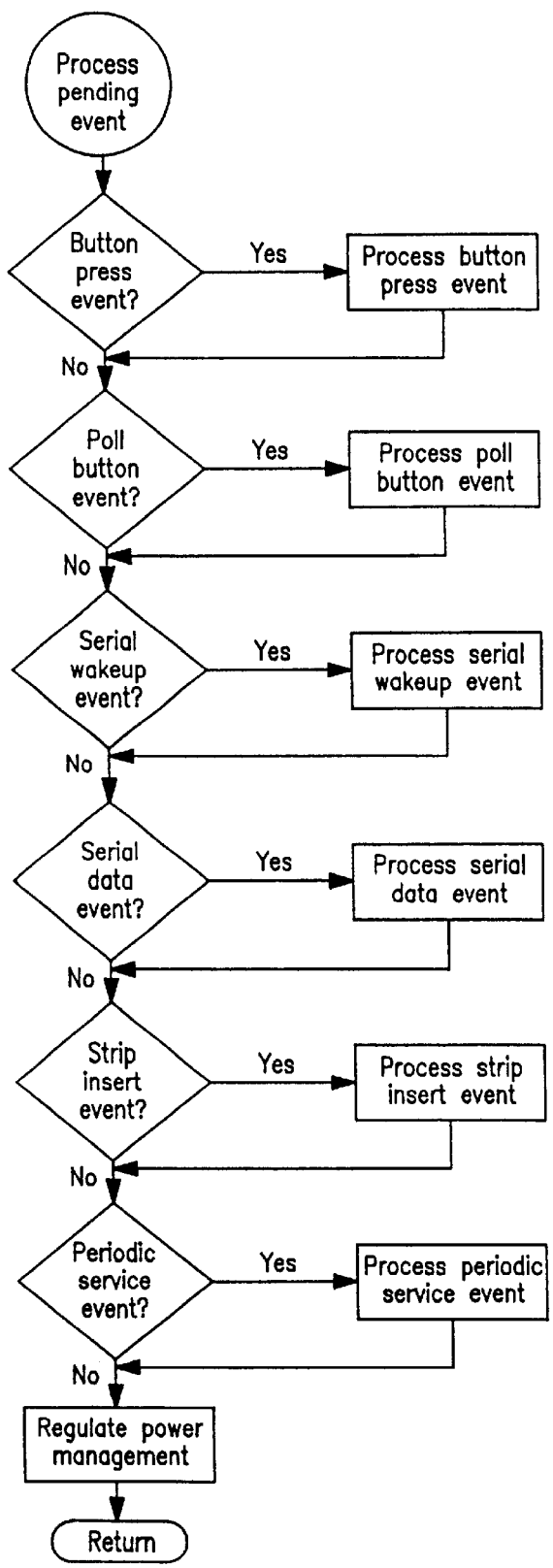
FIG. 18 illustrates a detail of the model illustrated in FIG. 17.

The process pending events function is illustrated in FIG. 18. The following actions take place when the μC 110 processes a pending event. The process button press event function is invoked when a button is pressed. This function has a delay that permits the user to press more than one button simultaneously. Then the function samples the buttons' states, saves the buttons' states and provides feedback to the user about which buttons are pressed. Based upon the current screen state, the appropriate screen handler routine is used for further processing. If a button is not pressed, the button press event is cleared.

The process poll button event function provides a fast key 54 press feature. A key 54*a*–*c* is pressed and held down. If the fast mode is active, the status of each key 54*a*–*c* is polled. If a pressed key 54*a*–*c* is in fast mode, feedback to the user is provided. Then the appropriate screen handler routine is employed. If a key 54*a*–*c* is pressed but not held down, the associated function, such as + or − is invoked.

The process serial wake up event occurs when the RS-232C wake up interrupt has been triggered. The current instrument 20 state is checked. If the instrument 20 is in idle state, the instrument 20's state is changed to monitor state and an acknowledgement is sent to the interrupt source. If the instrument 20 is not in idle state, the wake up is ignored and the pending event is cleared.

The process serial data event occurs when the UART receives a complete interrupt and determines whether the data in the serial I/O buffer should be processed further. If the data is a complete command, the UART detects the end of a data block, or the ASIC pass through mode is enabled, the routine to process data in the serial I/O buffer is invoked and the pending event is cleared.

The process strip insert event occurs when the periodic timer wake up determines that a strip 21 has been inserted. The power management system and LCD are initialized and permitted to stabilize. The routine to run a glucose test is invoked. The pending event is cleared.

The process periodic service event occurs when the periodic timer wake up determines that it is time to perform a temperature sample, update the termpearture history, adjust the internal self-heating variable, regulate power management (check the status of the power management and make adjustments when necessary), or check the timeout counters.

Figure 19:
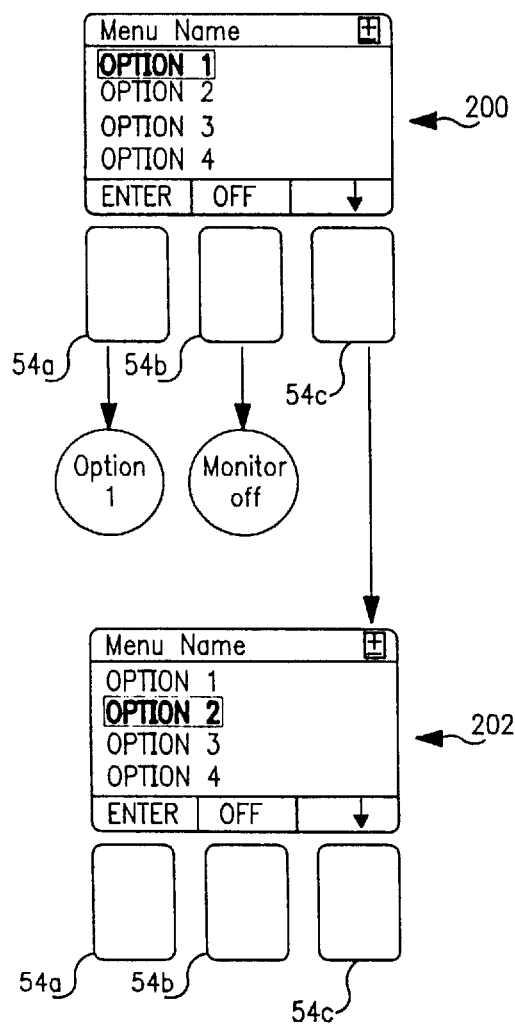

The user interface of instrument 20 will now be explained with reference to FIGS. 19–73. Referring particularly to FIG. 19, when screen 200 is displayed and the user presses key 54*a*, the function for option1, for example, "RUN GLUCOSE TEST," of instrument 20 is executed. When screen 200 is displayed and the user presses key 54*b*, instrument 20 is turned off. When screen 200 is displayed and the user presses key 54*c*, screen 202 offering option 2, for example, "REVIEW MEMORY," is displayed. The user advances in the same manner, scrolling up additional options 3, for example, "EDIT/ENTER DATA," 4, for example, "SET DATE AND TIME," 5, for example, "SET OPTIONS," 6, for example, "CHECK BATTERY," and so on, until the last option is displayed.

Figure 20:
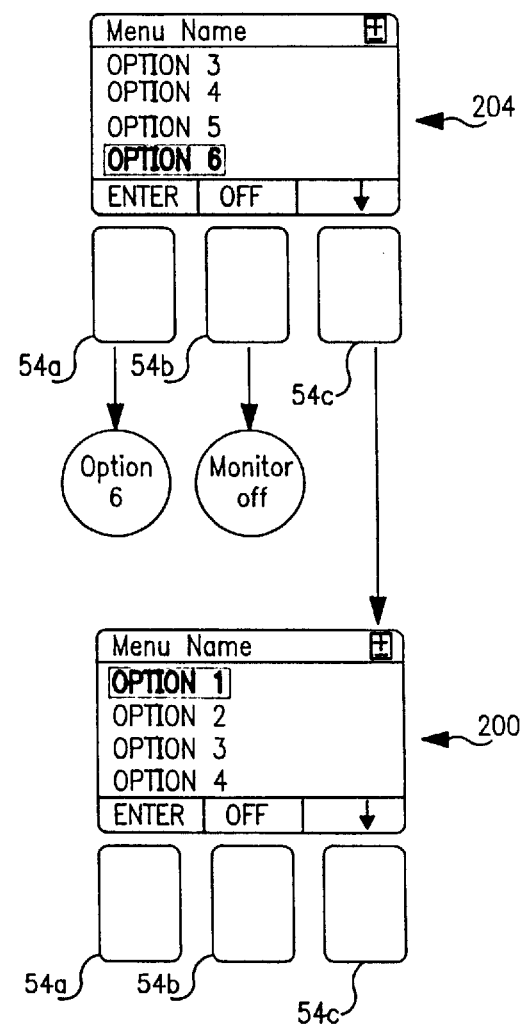

Turning now to FIG. 20, when screen 204 listing the last option is displayed and the user presses key 54*a*, the function for the last option, in the illustrated example, option 6, of instrument 20 is executed. When screen 204 is displayed and the user presses key 54*b*, instrument 20 is turned off. When screen 204 is displayed and the user presses key 54*c*, the option menu rolls over to option 1 and screen 200 is displayed.

Figure 21:
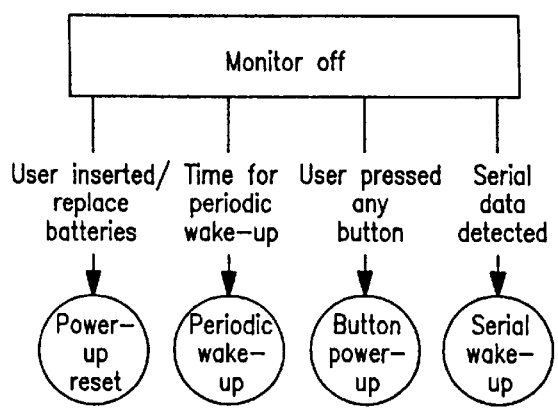
Figure 22:
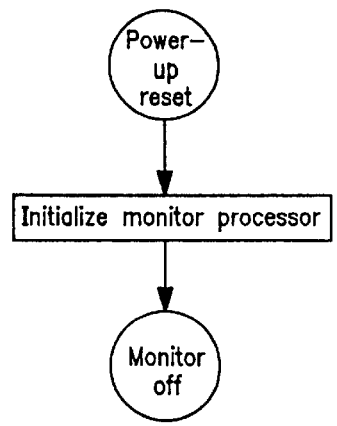
Figure 23:
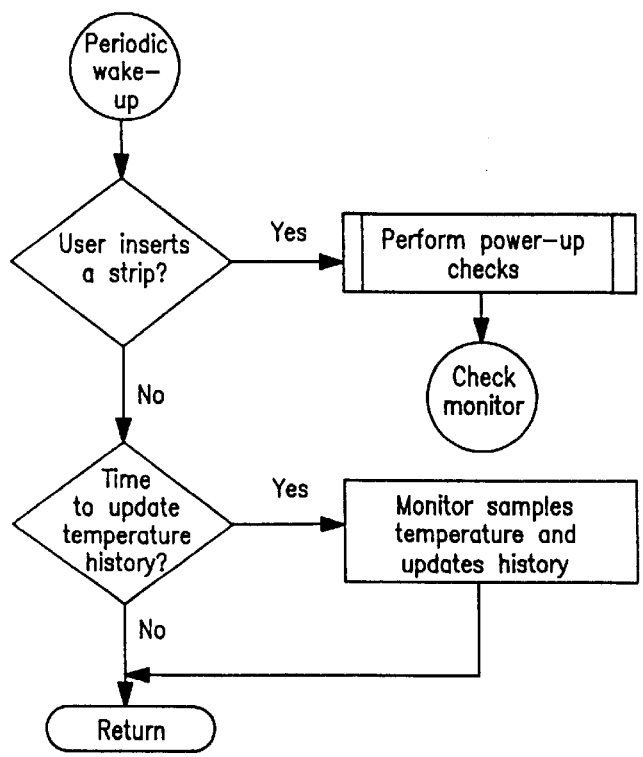
Figure 24:
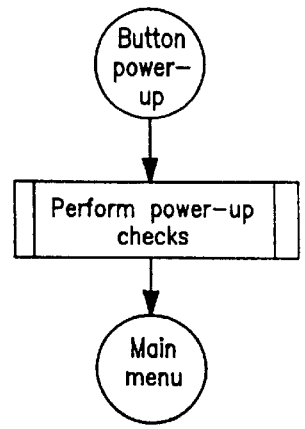
Figure 25:
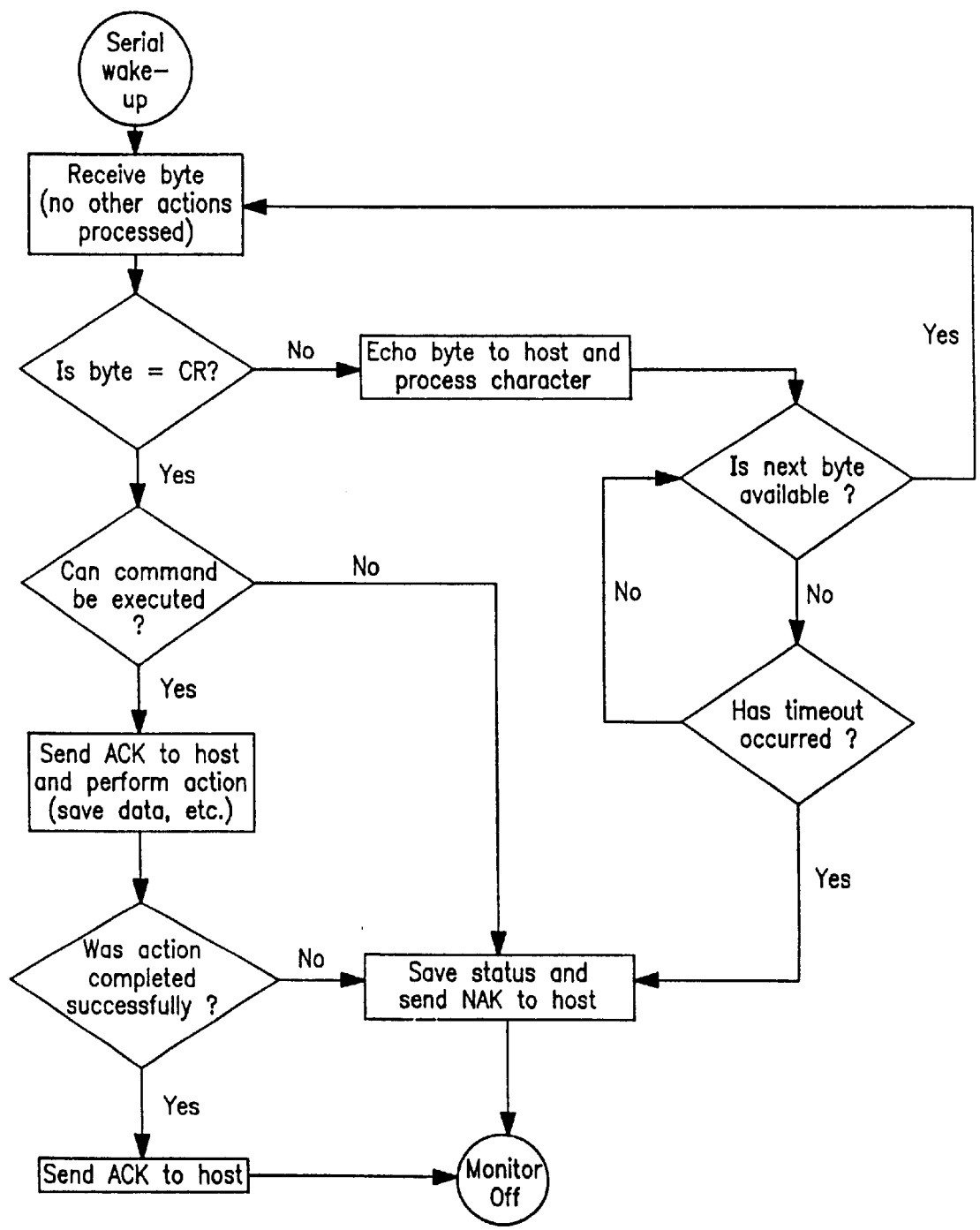

Turning now to FIG. 21, and assuming that the instrument 20 is in the off state, insertion of batteries 75 into the instrument 20 will place the instrument 20 in the power up reset state. See FIG. 22. If the time has elapsed prior to a periodic wake up, the instrument 20 will be placed in wake up state. See FIG. 23. If the user presses any button 54*a*–*c*, the instrument 20 will be placed in the wake up state. See FIG. 24. If instrument 20 detects serial data from, for example, port 160, the instrument 20 is placed in the wake up state. See FIG. 25.

Figure 26:
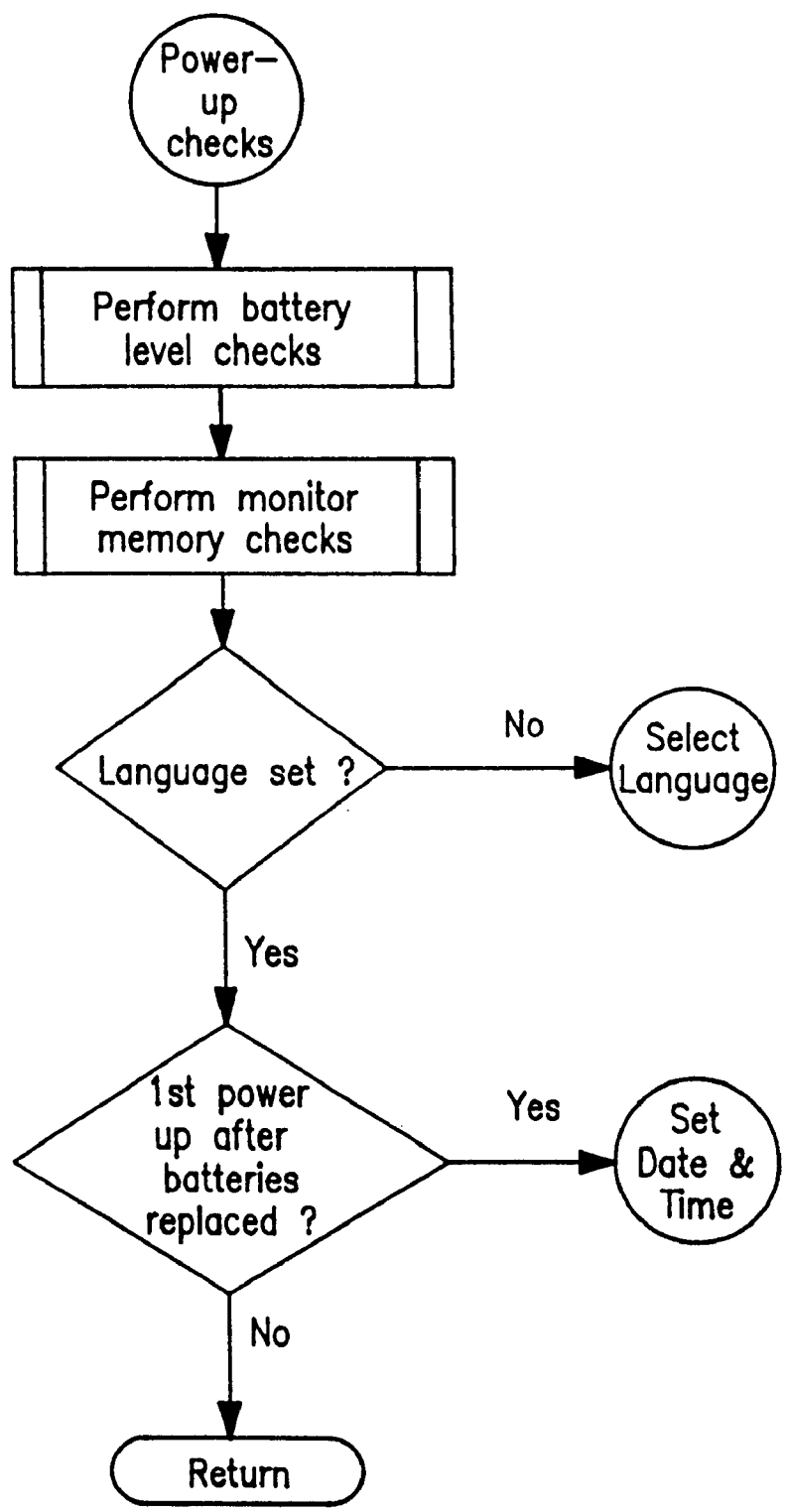

Immediately upon power up, instrument 20 performs its power up checks, illustrated in FIG. 26. These include the battery level check, illustrated in FIG. 27*a*. If the battery level is not sufficient to run instrument 20, the screen illustrated in FIG. 27*b* is displayed. From this screen, the user may turn the instrument 20 off until the batteries can be serviced by pressing key 54*b*. Alternatively, the instrument 20 will power itself off after passage of the timeout interval. If the battery 75 level is below a warning threshold, a battery warning icon is set in the display 42, advising the user that the batteries 75 need to be replaced. Ater performing the battery level check, the instrument 20 performs its memory checks illustrated in FIG. 28a. If instrument 20 fails its memory checks, the screen illustrated in FIG. 28b is displayed. From this screen, the user may turn the instrument 20 off until the instrument 20 can be serviced. Alternatively, the instrument 20 will power itself off after passage of the timeout interval.

Figure 29A:
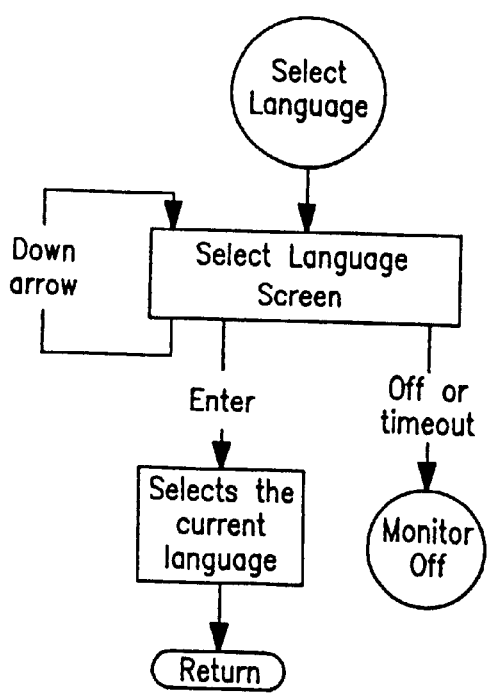
Figure 29B:
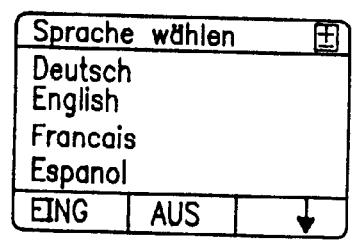

After performing the memory check, if a language has previously been selected, that selection is followed. If no language has previously been selected, the instrument executes its language selection routine for the language for its displays. See FIGS. 29a–b which illustrate the routine and the display prompt to the user. After the language for displays has been established, the instrument determines whether it needs to have its real time clock reset. If so, appropriate prompts are provided. If not, control is returned to the background program.

Figure 30A:
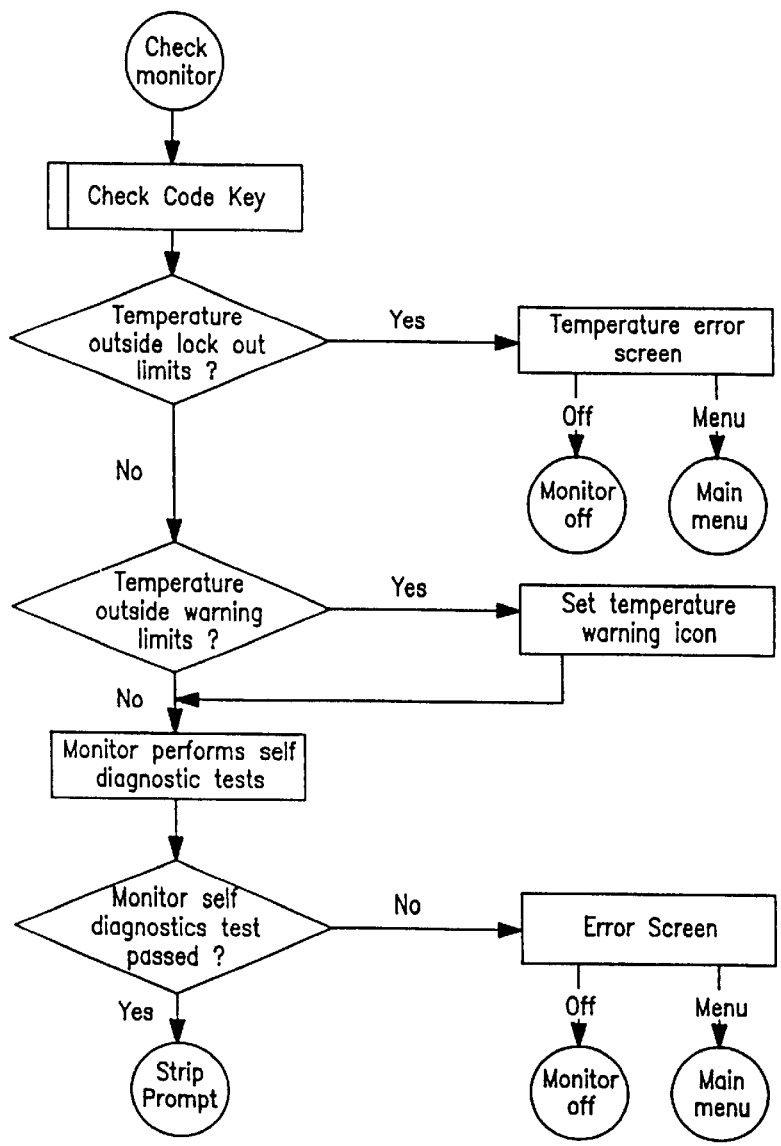
Figure 30B:
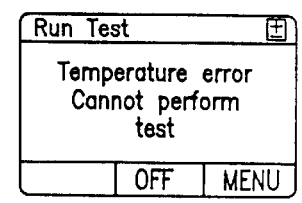
Figure 30C:
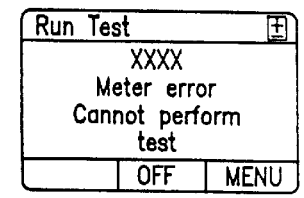

Before performing a measurement, the instrument 20 must check the code ROM key in port 140 (see FIGS. 31a–f), take a temperature reading, and perform certain self-diagnostic tests. See FIG. 30a. The instrument 20 proceeds to the temperature determination. If the ambient termperature is outside the lock out limits of instrument 20, the error message of FIG. 30b is displayed. From this error message, the user can either turn the instrument 20 off or return to the menu. The instrument 20 next proceeds to determine if the temperature is within the warning limits. If so, a temperature warning icon is displayed. The instrument 20 next proceeds to perform its self diagnostic tests. If it passes these tests, it prompts the user to insert a test strip 21 (see FIGS. 32a–c). If not, it displays the error screen illustrated in FIG. 30c. From this error message, the user can either turn the instrument 20 off or return to the menu.

Figure 3:
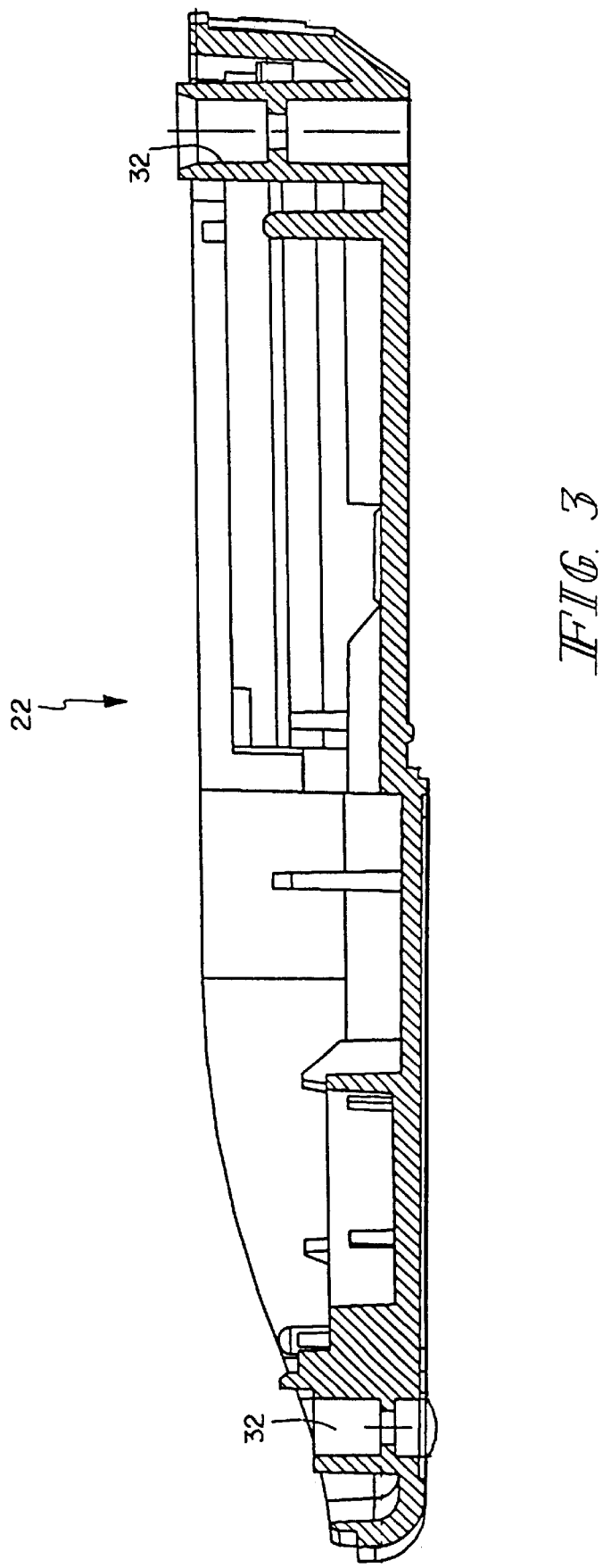
FIG. 3 illustrates a further enlarged sectional view, taken generally along section lines 3—3 of FIG. 2, of the detail illustrated in FIG. 2.
Figure 4:
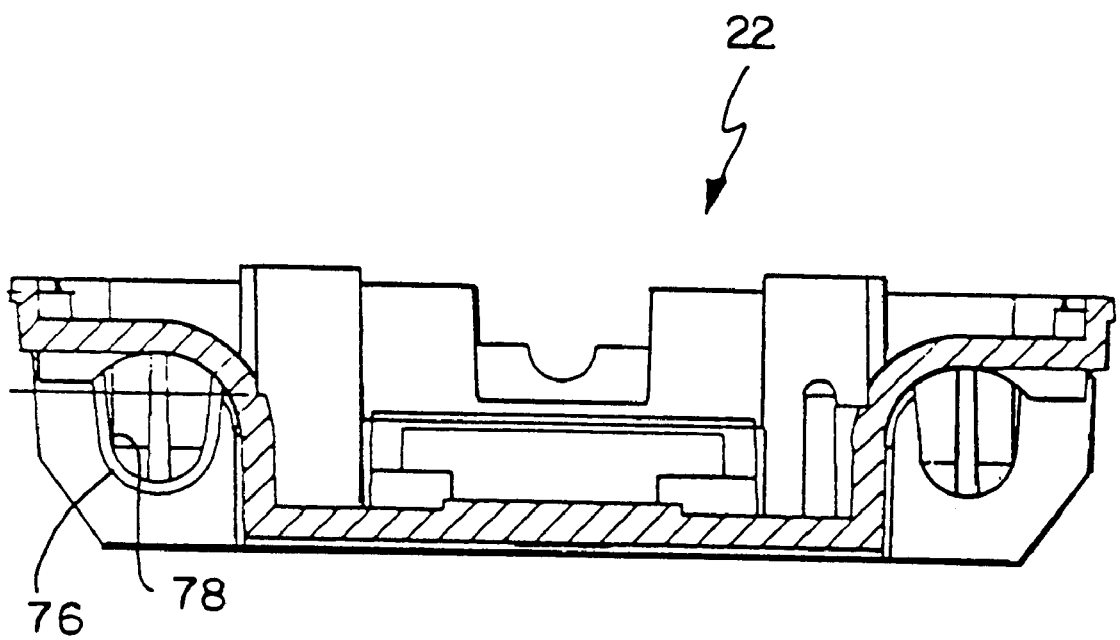
FIG. 4 illustrates a further enlarged sectional view, taken generally along section lines 4—4 of FIG. 2, of the detail illustrated in FIG. 2.
Figure 5:
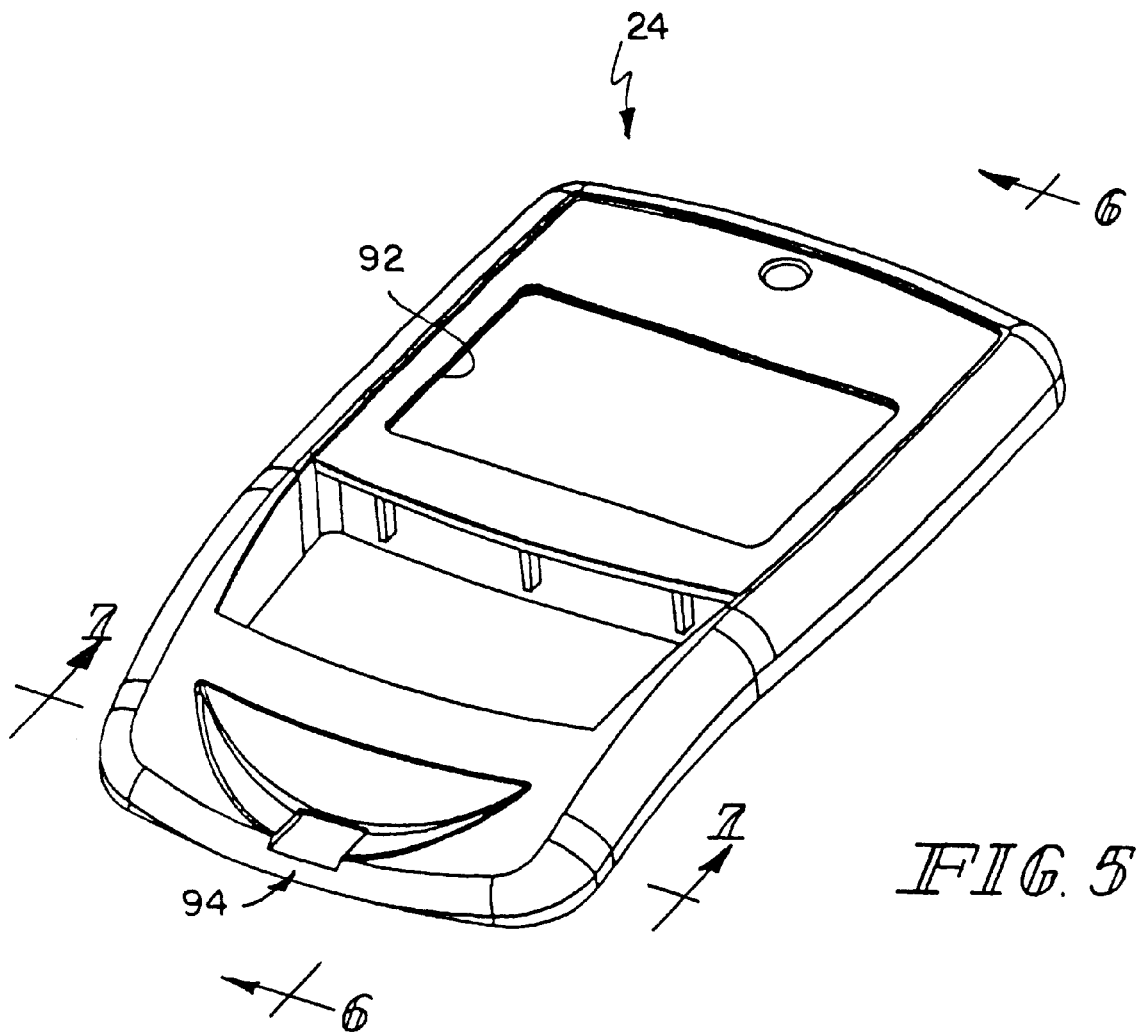
FIG. 5 illustrates an enlarged perspective view of a detail of the instrument illustrated in FIG. 1.
Figure 6:
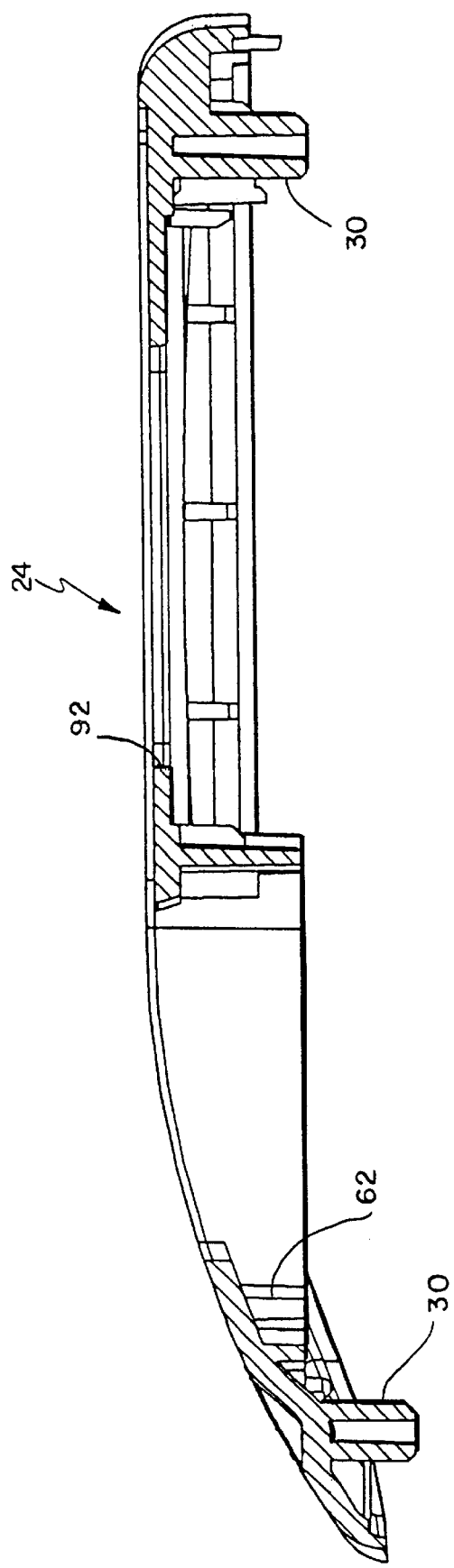
FIG. 6 illustrates a further enlarged sectional view, taken generally along section lines 6—6 of FIG. 5, of the detail illustrated in FIG. 5.
Figure 7:
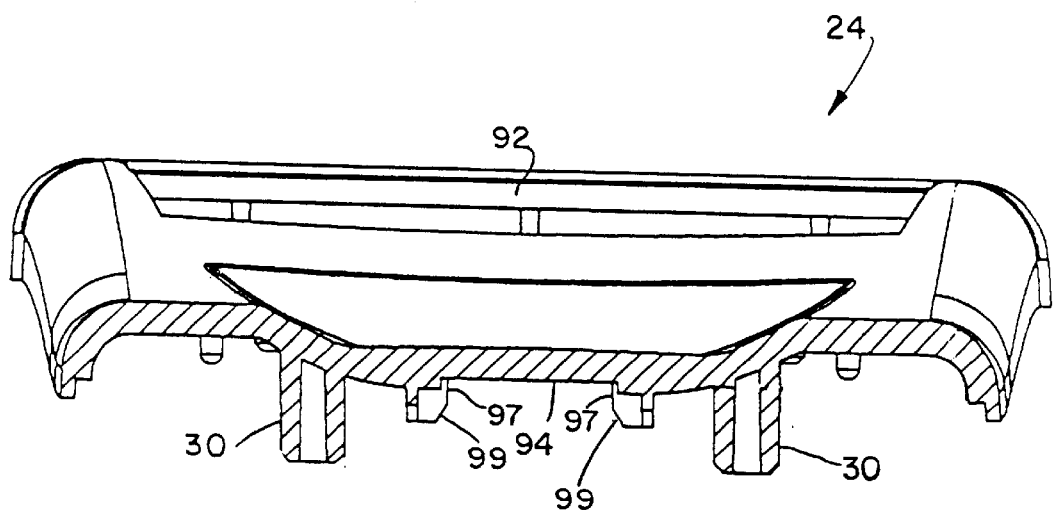
FIG. 7 illustrates a further enlarged sectional view, taken generally along section lines 7—7 of FIG. 5, of the detail illustrated in FIG. 5.
Figure 31A:
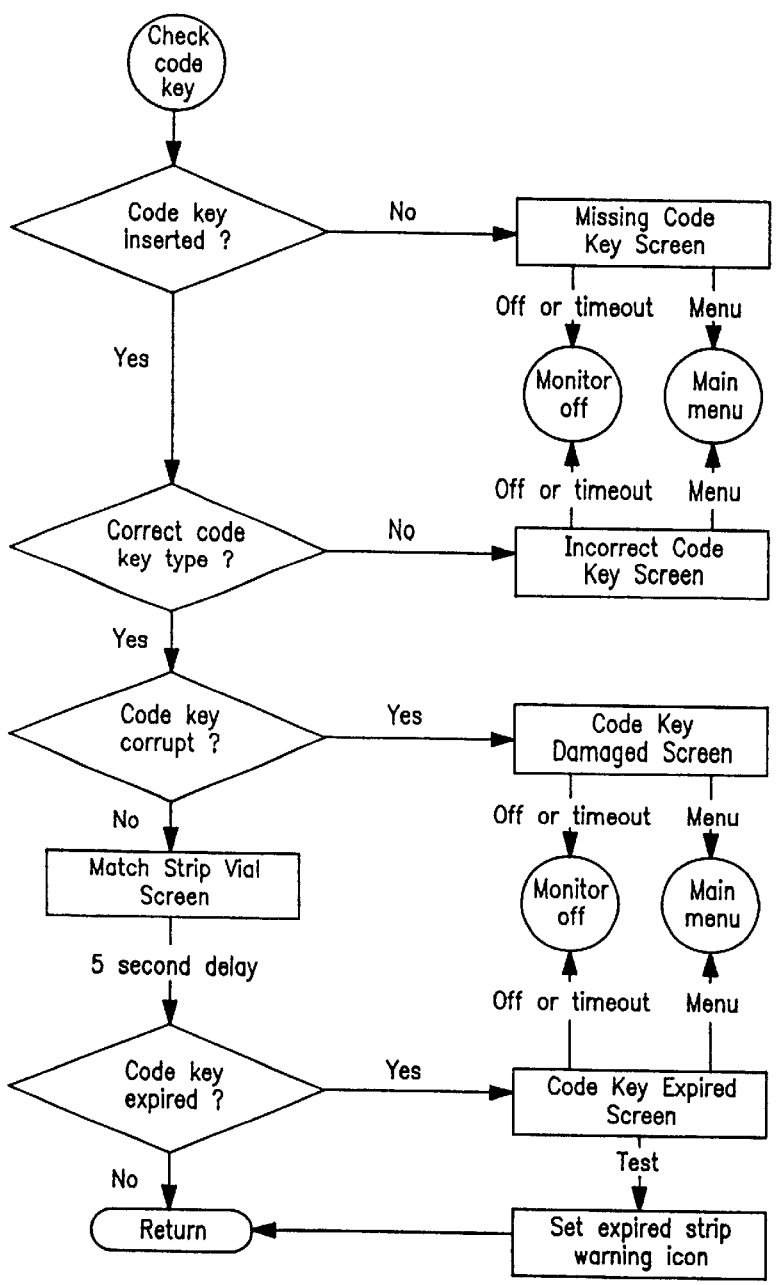
Figure 31B:
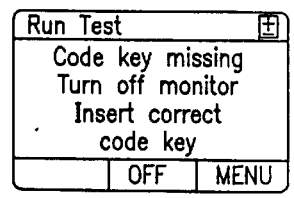
Figure 31C:
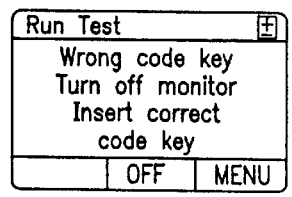
Figure 31D:
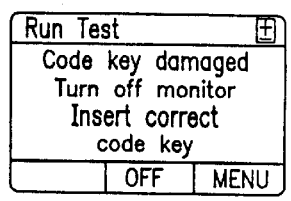
Figure 31E:
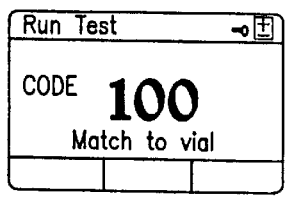
Figure 31F:
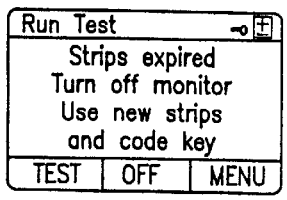

Turning to FIGS. 31a–f, port 140 is checked to determine if a code ROM key is inserted into it. If not, the missing code key screen illustrated in FIG. 31b is displayed. From this error message, the user can either turn the instrument 20 off or return to the menu. If a code key is in the port 140, the type of key is determined. If the type of key is incorrect, an incorrect code key message is displayed. See FIG. 31c. From this error message, the user can either turn the instrument 20 off or return to the menu. If the correct type of code key is in port 140, the integrity of the code key's ROM contents is checked. If the code key ROM contents are corrupt, a code key damaged message is displayed. See FIG. 31d. From this error message, the user can either turn the instrument 20 off or return to the menu. If the code key ROM contents are viable, the code number of the code key is displayed for the user to compare to the code printed on the vial of strips from which the user will take a strip 21 for a glucose test. See FIG. 31e. The instrument 20 next determines from the information contained in the code key ROM whether the strips 21 associated with that code key are expired. If so, a strips expired message is displayed. FIG. 3 If From this error message, the user can turn the instrument 20 off, return to the menu, or conduct a test using the expired strip 21. If the user elects to conduct a test using the expired strip 21, an expired strip warning icon is set on the display 42, and the instrument 20 returns to the background routine. If the strips have not expired, the instrument 20 returns to the background routine.

Figure 32A:
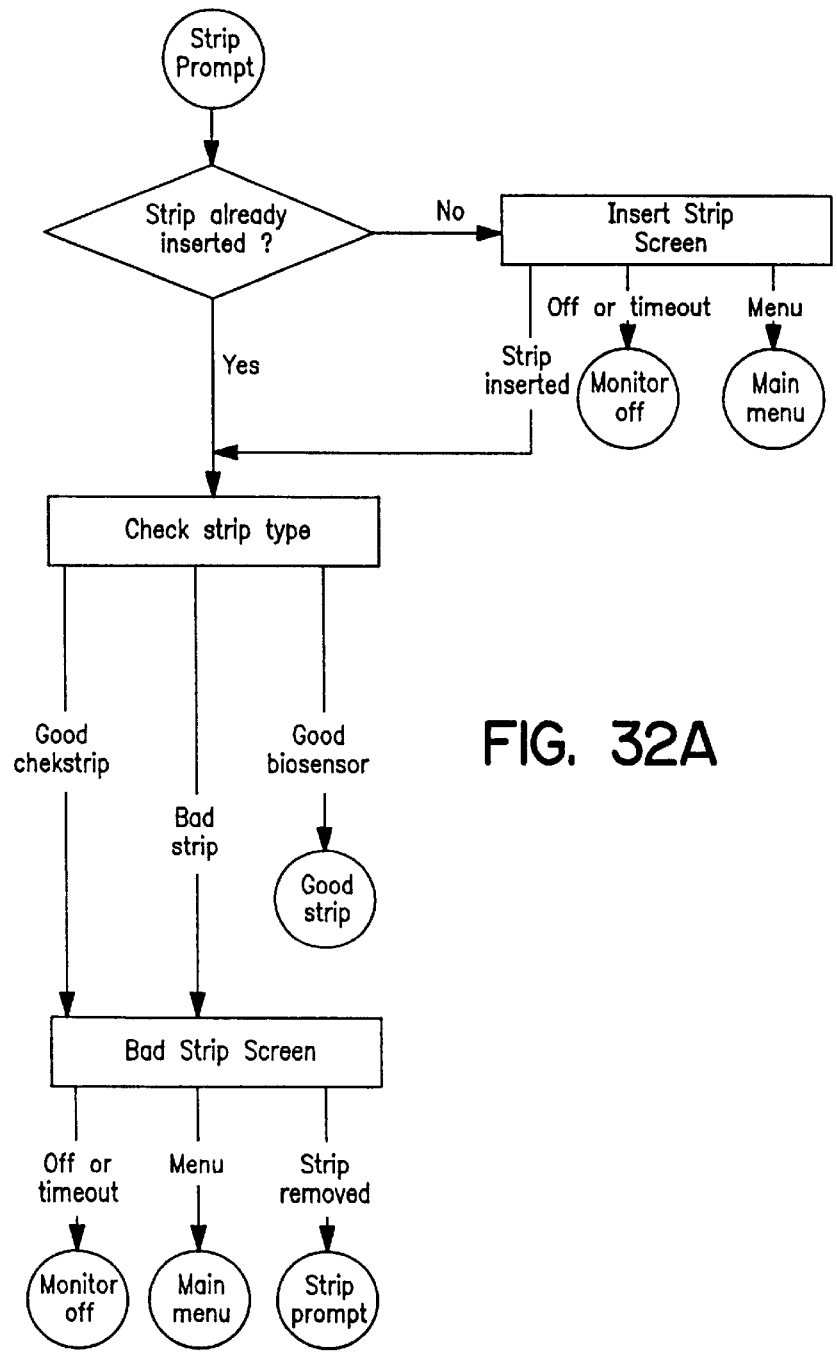

Turning now to the strip prompt routine illustrated in FIG. 32a, the instrument first determines if a strip 21 is already in the strip port 96. If not, the user is prompted by the display 42 to insert one. See FIG. 32b. The user may also advance from the display of FIG. 32b by turning instrument 20 off or by returning to the menu. If a strip 21 is already in port 96, or the user inserts one in response to the display of FIG. 32b, the instrument 20 next determines the type of strip inserted, based upon certain electrical characteristics of the strip. The firmware contemplates three possibilities: a good diagnostic, or check, strip; a good test strip; or, a bad strip. If the strip is determined by instrument 20 to be bad, a bad strip message is displayed. See FIG. 32c. From this error message, the user can turn the instrument 20 off, return to the menu, or remove the strip, at which time the instrument 20 again prompts for the insertion of a strip. See FIG. 32b.

Figure 32B:
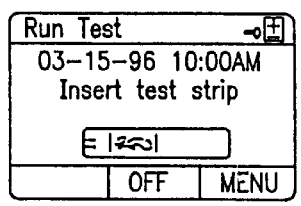
Figure 32C:
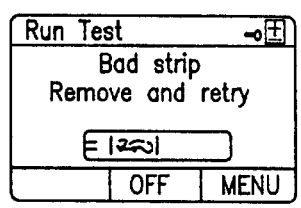
Figure 33A:
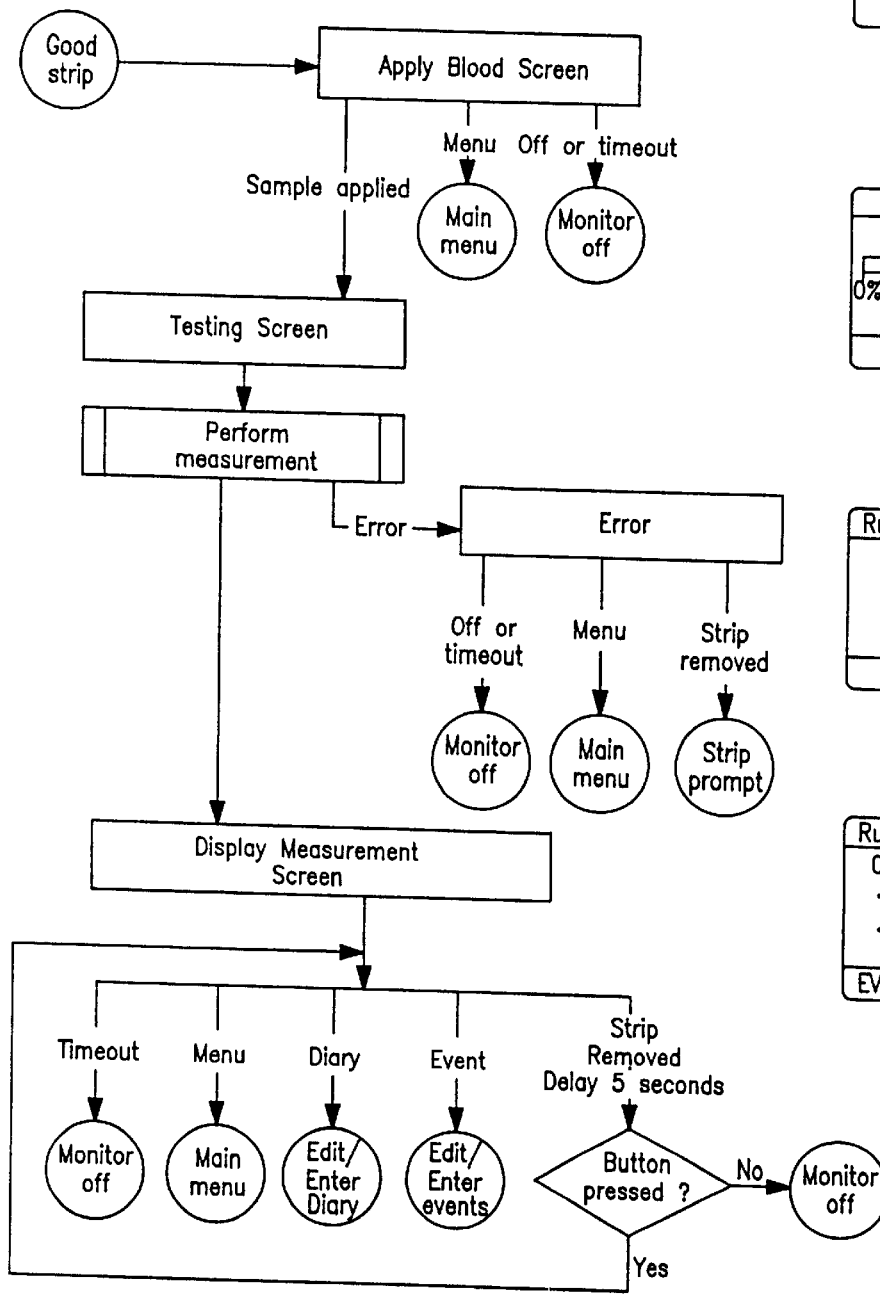
Figure 33B:
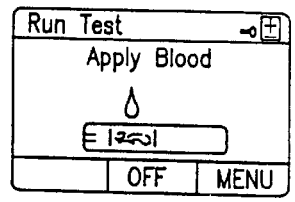
Figure 33C:
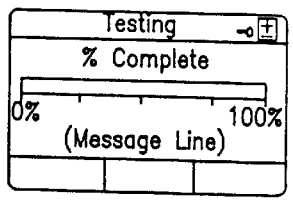
Figure 33D:
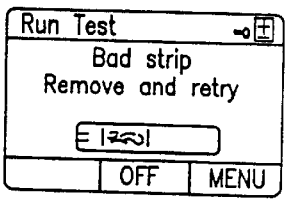
Figure 33E:
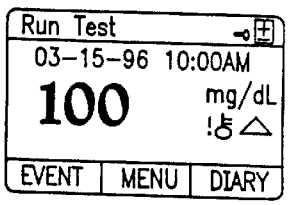

If the instrument 20 determines that the inserted strip 21 is a good one, the instrument 20 prompts the user to apply blood to the target area of the strip 21. FIGS. 33a–b. The user can escape by turning the instrument 20 off or by returning to the main menu, or the user can apply blood to the strip 21. If the user applies blood to a strip 21, the instrument 20 displays the testing screen. See FIG. 33c. This screen includes a gauge which indicates approximately the percentage completion of the test and a message, or tip, from among a library of programmed tips. These messages crawl across a message line of the display in the illustrated instrument 20.The instrument 20 performs the glucose concentration determination. If an error is detected in the performance of this determination, an error message is displayed. See FIG. 33d. From the detection of such an error, the user can turn the instrument 20 off, return to the main menu or remove the strip. If the strip is removed, the strip prompt, FIGS. 32a–b, is displayed. If no error is detected, the instrument proceeds to display the measurement on the display 42. See FIG. 33e. The user can respond to the display of the measurement by permitting the instrument 20 to time itself out and power down, by returning to the main menu, by removing the strip, by selecting to enter events associated with the just completed measurement, or by selecting the diary for entry of the just completed measurement.

Figure 34A:
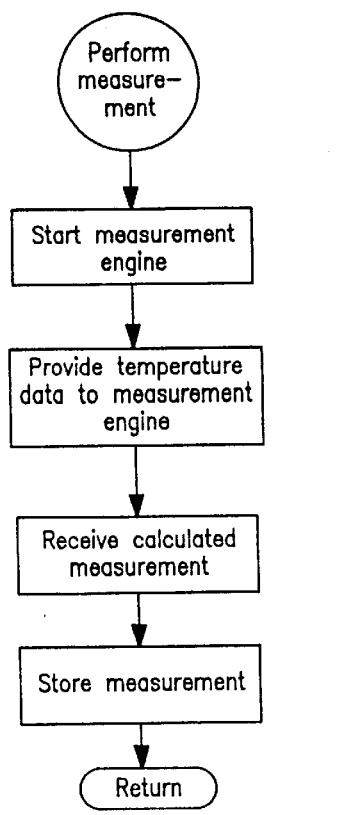
Figure 34B:
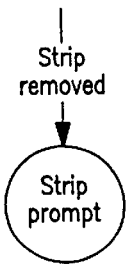
Figure 34C:
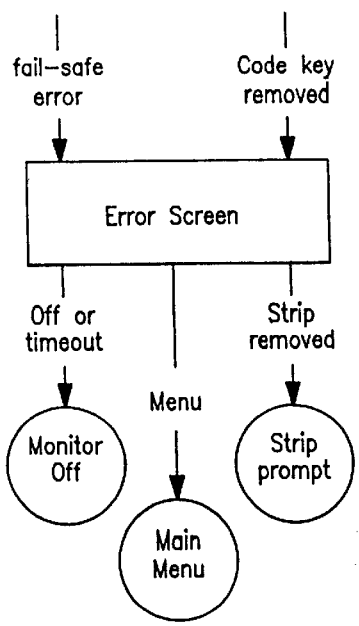
Figure 34D:
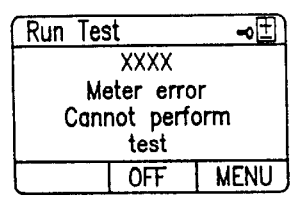
Figure 34E:
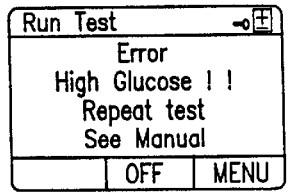

The performance of the measurement will be described with reference to FIGS. 34a–e. Referring particularly to FIG. 34a, the instrument 20's measurement engine is started, temperature data is provided to the measurement engine, the glucose measurement is calculated and stored, and control is returned to the background routine. During the performance of the measurement, if the strip 21 is removed from port 96, or if the code ROM key is removed from port 140, an error screen is displayed. See FIGS. 34b–d. The type of error is indicated in the display of FIG. 34d. This is the meaning of the X's in FIG. 34d. The user can respond to the display of FIG. 34d by turning the instrument 20 off or by returning to the main menu. FIGS. 34b–c. If the strip 21 has been removed during performance of the measurement, the display 42 prompts the user to insert a strip 21. If the measurement results in an excessive glucose concentration indication, a different screen is displayed. That screen is illustrated in FIG. 34e, the glucose overflow error screen.

Figure 35A:
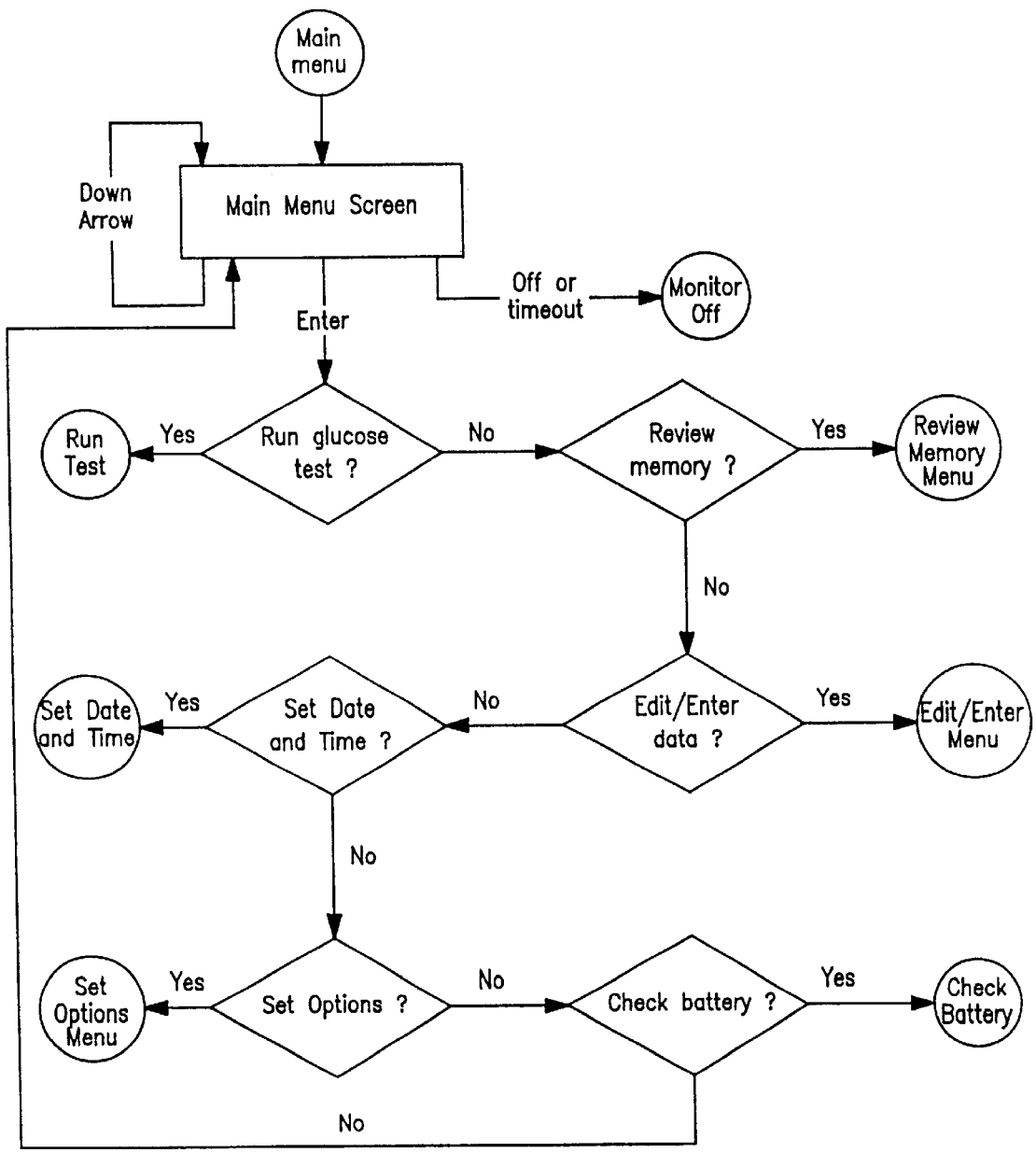
Figure 35B:
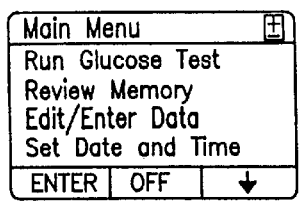
Figure 35C:
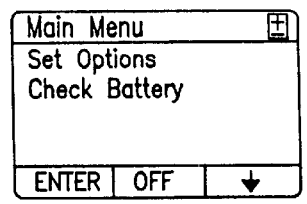
Figure 36A:
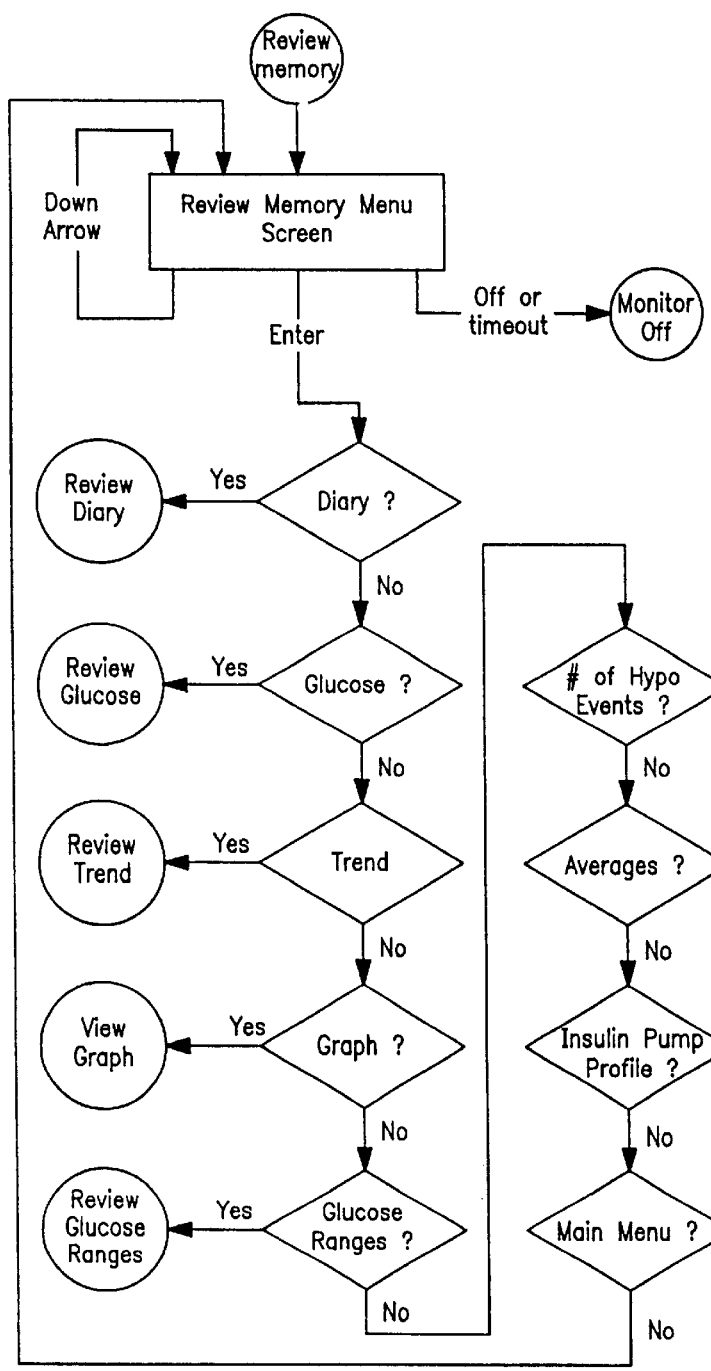
Figure 36B:
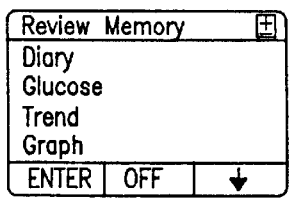
Figure 36C:
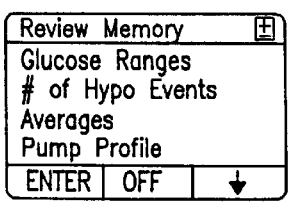
Figure 36D:
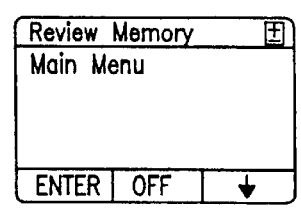

Turning now to the options available in the main menu, and with reference to FIGS. 35a–c, selection of the main menu by the user causes a main menu screen to be displayed. The user may scroll through the options available from the main menu by pressing key 54c. The screen continues to roll over until all available options from which the user may select have been displayed. See FIGS. 35b–c. The user may select from among these available options as indicated in the flowchart illustrated in FIG. 35a. The options include: running a glucose test (FIGS. 32a–c, 33a–e and 34a–e); reviewing the contents of the instrument 20's memory (FIGS. 36a–d); editing the memory menu and making entries to it (FIGS. 46a–d); setting the date and time (FIGS. 60a–c); setting the options (menu) (FIGS. 61a–c); and, checking the battery (FIGS. 69a–b).

Running a glucose test has previously been described. Reviewing memory can best be illustrated by referring to 36a–d. If the user elects to review memory, a screen is displayed from which the user can select from among the various memory files. See FIGS. 36b–c. The user scrolls down through the various memory files until the one the user wishes to review is highlighted. One of the file options is a return to the main menu. The remaining file options include the options to review: diary; prior glucose test results; test results trends; a graph of selected glucose test results; glucose ranges; the number of hypoglycemic events recorded in the memory; glucose averages; and, insulin pump profiles for insulin pump users.

Figure 37A:
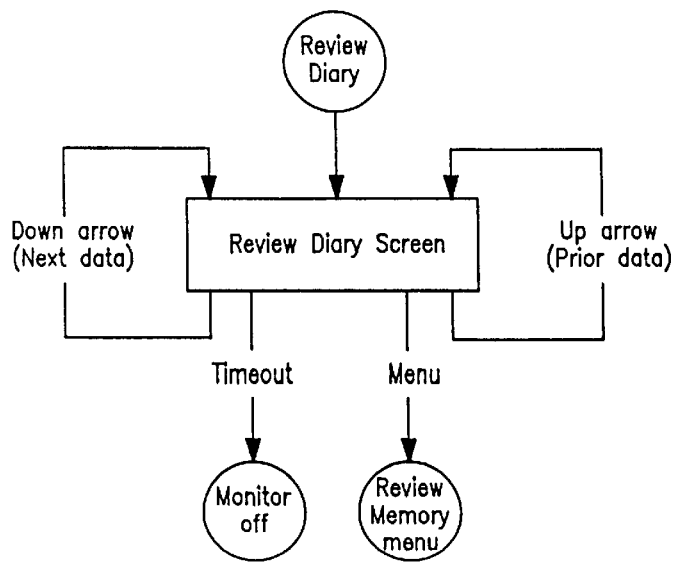
Figure 37B:
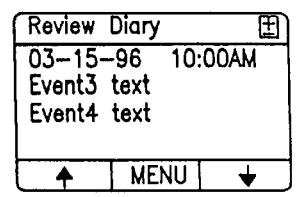
Figure 37C:
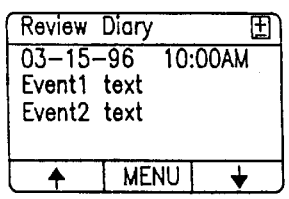
Figure 37D:
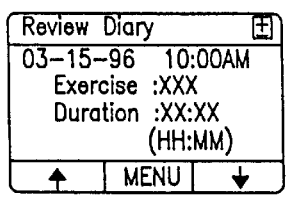
Figure 37E:
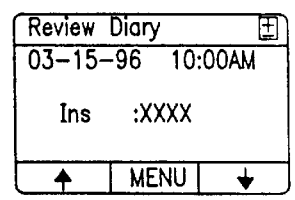
Figure 37F:
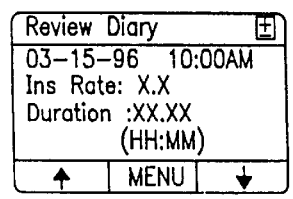
Figure 37G:
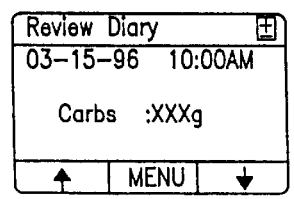
Figure 37H:
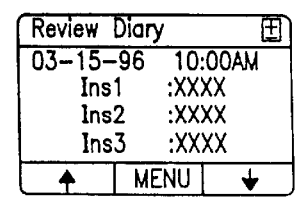
Figure 37I:
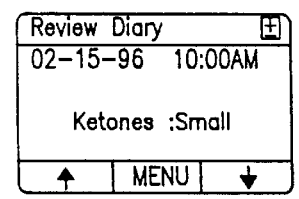
Figure 37J:
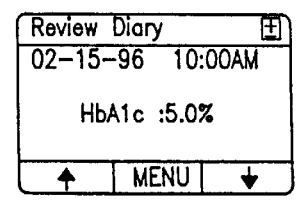
Figure 37K:
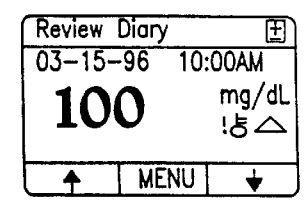

If the user selects the review diary option, the screen illustrated in FIG. 37b is displayed. The user is permitted to review multiple events in each diary entry, and the most recently entered events are displayed first. The user may scroll up to earlier entered events. FIG. 37c. Events include, for example: type and time duration of various forms of exercise (FIG. 37d); carbohydrate intake (FIG. 37e); amounts of each of a number of different types of insulin taken (FIG. 37f); and, amounts of certain other biologically significant components (in the illustrated examples, ketones—FIG. 37g, and glycosylated hemoglobin—FIG. 37h) detected in the samples applied to strips 21 (of course, the strips 21 must be capable of providing reliable indications to the instrument 20 of any such components). The display 42 denotes any out of limits results with exclamation marks (!).

Figure 38A:
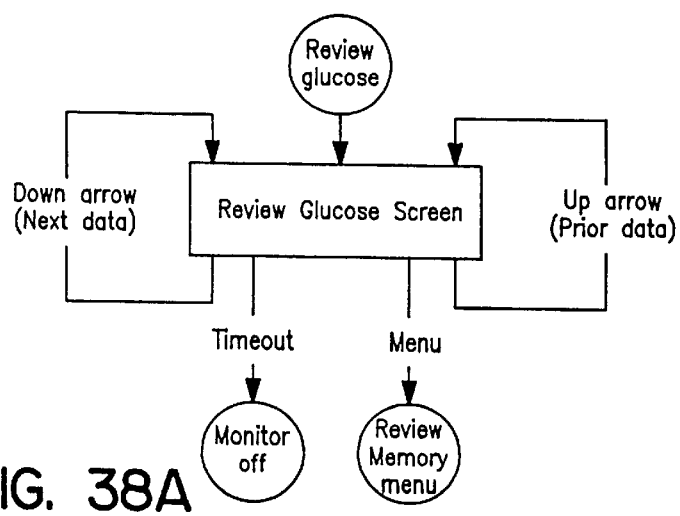
Figure 38B:
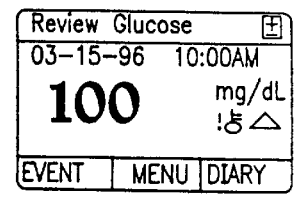

If the user selects the review glucose option, the screen illustrated in FIG. 38b is displayed. The user may scroll up to data from earlier readings and down to more recent readings. No readings other than glucose concentration test results are displayed under this option. Any applicable warnings, such as temperature out of range at the time of measurement, glucose concentration out of range, and so on, are displayed with the glucose readings.

Figure 39A:
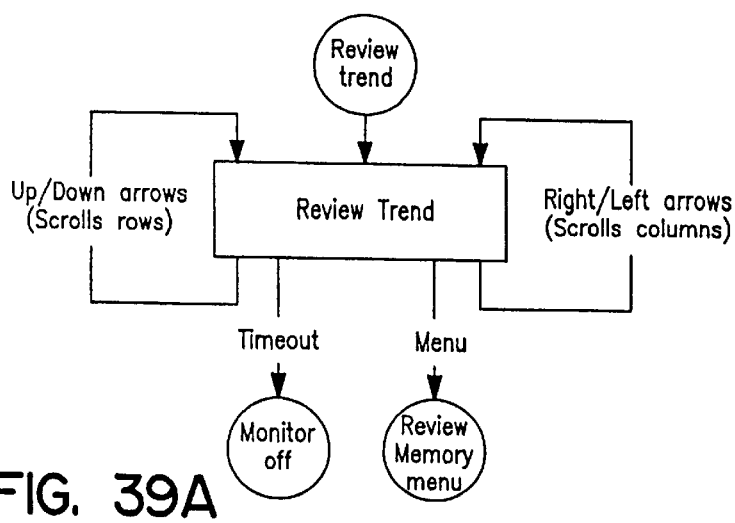
Figure 39B:
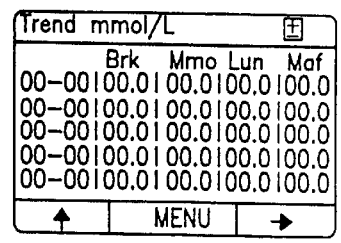

If the user selects the review trend option, the screen illustrated in FIG. 39b is displayed. This screen has rows representing days on which readings are stored in memory, with each day being divided into a number of columns representing a number of time segments of the 24 hour day. In the illustrated instrument 20, the user can divide the day into eight segments according to the user's own treatment regimen, habits, and so on, but the entire 24 hours of each day must be accounted for. In the illustrated instrument 20, the eight columns are somewhat arbitrarily labelled: BReaKfast; MidMOrning; LUNch; MidAFternoon; DINner; EVEning; BEDtime; and, NiGhTtime. Illustratively, the corresponding time intervals might be, for example: 6:00 am–8:59 am; 9:00 am–3 11:59 am; 12:00 noon–1:59 pm: 2:00 pm–4:59 pm; 5:00 pm–7:59 pm; 8:00 pm–9:59 pm; 10:00 pm–2:59 am; and, 3:00 am–5:59 am, respectively. As previously noted, the time interval width, starting time and ending time of each column are user selectable, as will be explained. In the illustrated instrument 20, out of range readings are displayed in reverse video, with light numbers on a dark background.

Figure 40A:
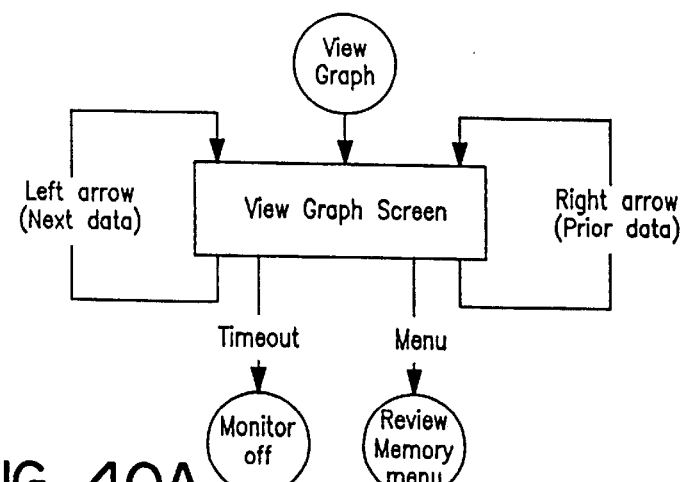
Figure 40B:
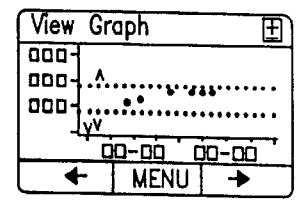

If the user selects the graph option, a graph of results will be displayed. See FIG. 40b. In the illustrated instrument 20, the x axis represents forty-eight hours with divisions every six hours. The scale of the y axis is 50–350 mg/dL with a division each 100 mg/dL in this range. The user's normal range can be entered, as will be discussed, and, if entered will be indicated by dotted lines. Values within the user's range are illustrated by + symbols. Values outside the instrument 20's reading range range low are illustrated by V symbols. Values outside the instrument 20's reading range high are illustrated by Λ symbols. The user may scroll forward and back using keys 54c and 54a, respectively, and values forward and back in time from the displayed 48 hours will appear on the graph.

If the user selects the glucose ranges option, the user is asked to select a date range for records to be viewed. In the illustrated instrument 20, the user may select the last thirty days, the last fourteen days, the last seven days or the last forty-eight hours. The screen illustrated in FIG. 41b will be displayed with the date range displayed at the top of the display. The display will display the percentage of hypoglycemic test results, and the number of total test results in the date range. If the user presses key 54c, additional records including the percentage of low readings, the percentage of readings in the normal range, the percentage of high readings, and, again, the total number of test results in the date range, will be displayed. See FIG. 41c. The date range is selected as illustrated in FIGS. 42a–b. The user selects the date screen, illustrated in FIG. 42b, and scrolls down using key 54c until the desired date range is highlighted. The user then selects that date range using key 54a. The instrument then returns to the routine illustrated in FIG. 41a.

Figure 43A:
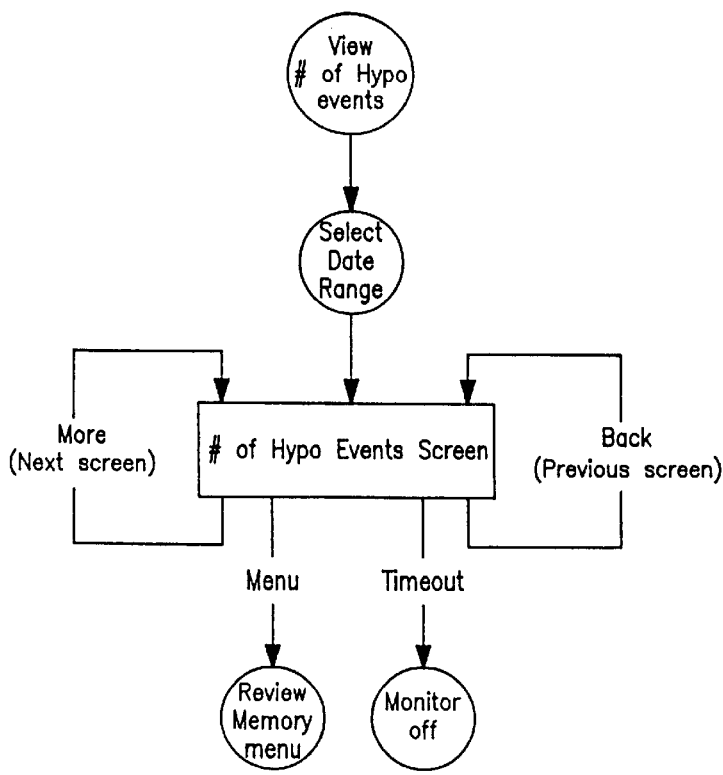
Figure 43B:
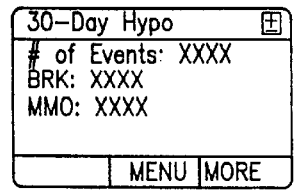
Figure 43C:
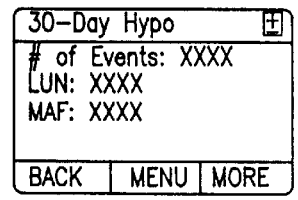
Figure 43D:
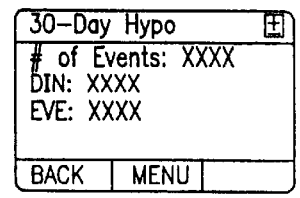
Figure 43E:
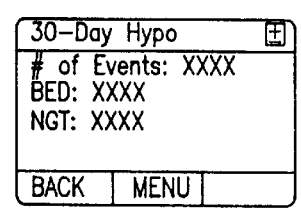

If the user selects the number of hypoglycemic events option, the user is asked to select the date range over which the number of hypoglycemic events will be reported. See FIGS. 42a–b. Once the user has selected a date range, the screen illustrated in FIG. 43b is displayed. In the illustrated instrument, the number of hypoglycemic events is reported by time of day. See the above discussion of FIGS. 39a–b. The user can scroll down and up among the number of hypoglycemic events reported by time of day by pressing keys 54c and 54a, respectively.

Figure 44A:
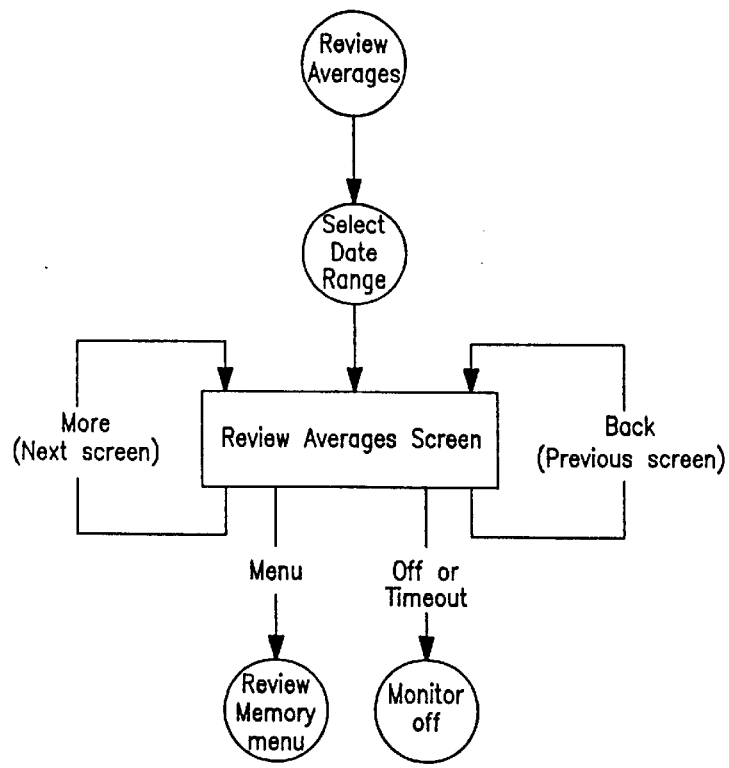
Figure 44B:
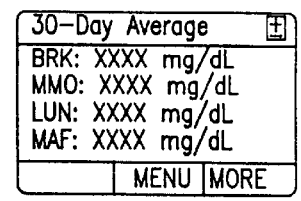
Figure 44C:
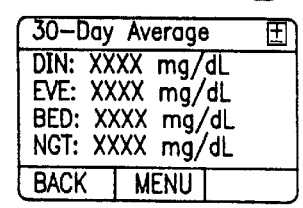

If the user selects the review averages option, the user is again asked to select the date range over which the averages will be calculated. See FIGS. 42a–b. Once the user has selected a date range, the screen illustrated in FIG. 44b is displayed. In the illustrated instrument, the averages are reported by time of day. See the above discussion of FIGS. 39a–b. The user can scroll up and down among the averages reported by time of day by pressing keys 54a and 54c, respectively.

If the user selects the review insulin pump profile option, the screen illustrated in FIG. 45b is displayed. Other insulin pump information, such as temporary basal rates, bolus and square wave bolus, is illustrated with other information when the review diary option is selected.

Figure 46A:
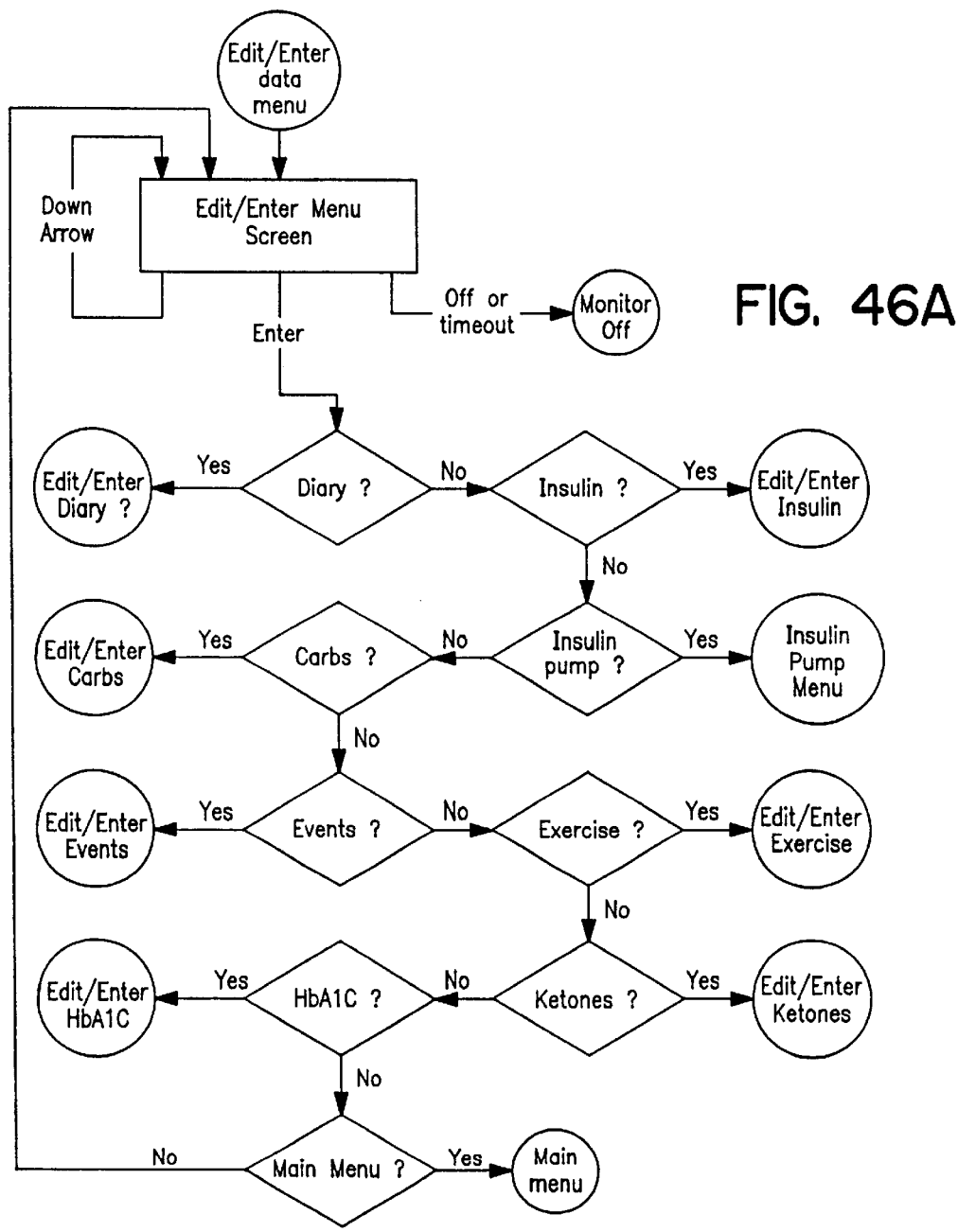
Figure 46B:
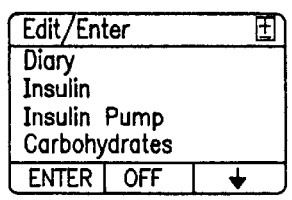
Figure 46C:
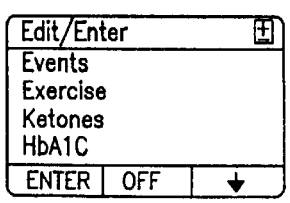
Figure 46D:
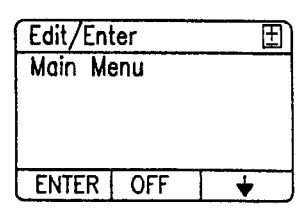

Returning briefly to FIG. 35a, the user may edit and enter in the main data menu as illustrated in FIGS. 46a–d. If the user selects this option, the screen illustrated in FIG. 46b is displayed. The user may scroll down among the options on the main data menu by pressing key 54c. See FIGS. 46c–d. The menu rolls over when the last screen is reached. The user selects a highlighted option by pressing key 54a. The options in the illustrated instrument 20 include: diary; insulin types; insulin pump operating parameters; carbohydrate intake; events; exercise; ketones; glycosylated hemoglobin; and, return to the main menu.

To edit and enter diary, the flowchart illustrated in FIG. 47a is instructive. First, the date and time are selected. Once the user has selected the date and time in which the user is interested, the diary settings for that date and time are displayed beginning with the display illustrated in FIG. 47b. The user may advance through the various screens for that date and time by pressing key 54c. The user may recall previous screens by pressing key 54b. See FIGS. 47c–f The user may change a diary entry by pressing key 54a, and then selecting the entry to be changed by pressing key 54*b* to advance the highlighting of the entries. See FIG. 47*g*. Once the entry to be changed is highlighted, the user can increase the entry value by pressing key 54*c* or decrease the entry value by pressing key 54*a* until the appropriate value is displayed. See FIGS. 47*h–k*. The save key appears on the last screen, FIG. 47*f* The user cannot save changed data until all screens, FIGS. 47*b–f*, have been displayed.

The user is prompted to select the date and time by the display of the screen illustrated in FIG. 48*b*. The user may scroll up to earlier entries using key 54*c*. In the illustrated instrument, the screen illustrated in FIG. 48*b* is only displayed when the user enters the routine illustrated in FIG. 46*a*.

Figures 49A, 49B, 49C:
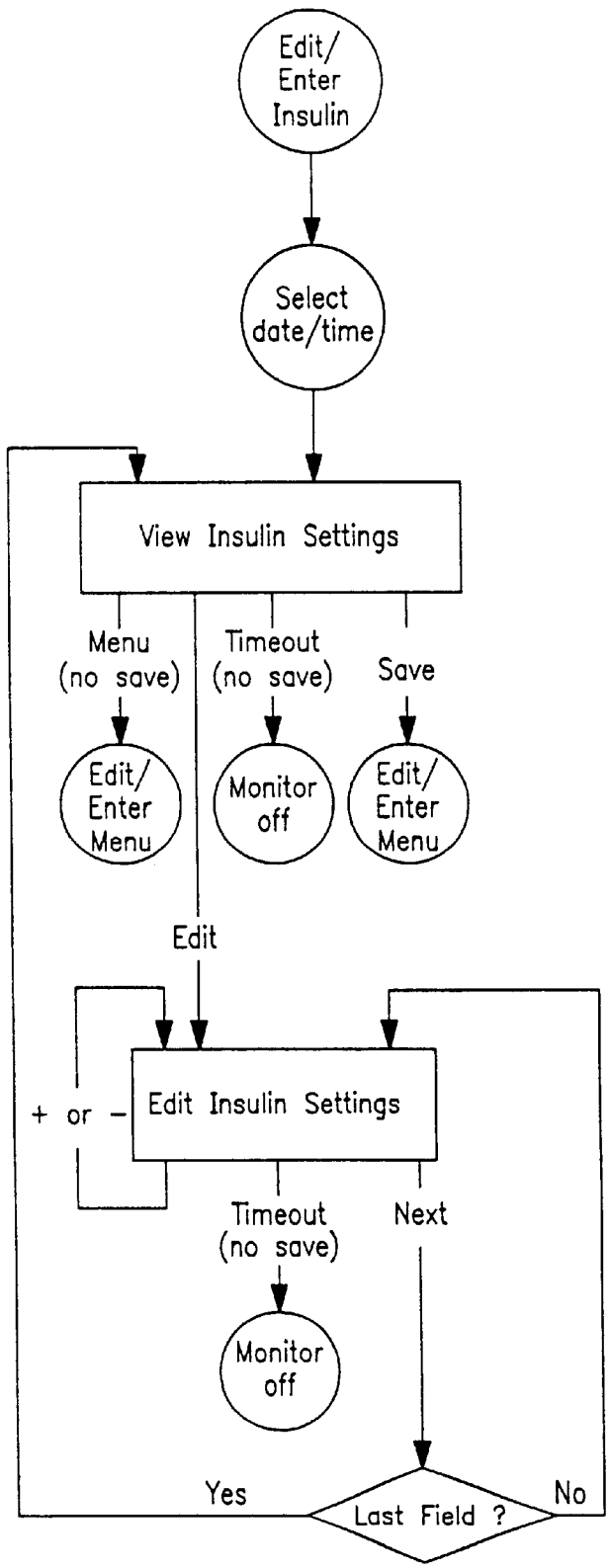

To edit or enter insulin settings, the user first selects the date and time (see FIGS. 48*a–b*), and then views the current insulin settings on the display illustrated in FIG. 49*b*. Pressing key 54*c* saves the displayed settings. No other action saves them. Pressing key 54*a* permits the user to edit or enter new settings. The user selects the setting to be edited or entered by depressing key 54*b* until that setting is highlighted. The user presses key 54*a* to reduce that setting and presses key 54*c* to increase that setting.

Figure 50A:
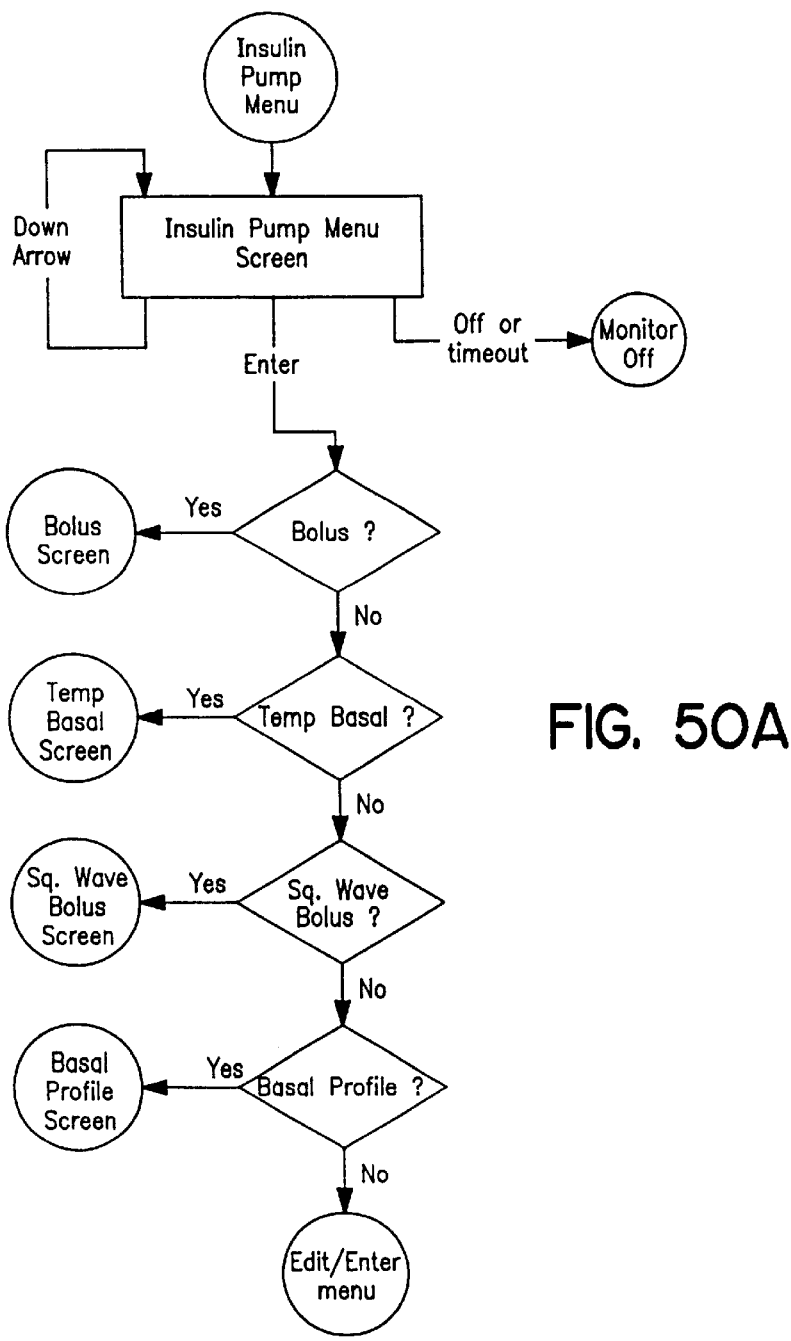
Figure 50B:
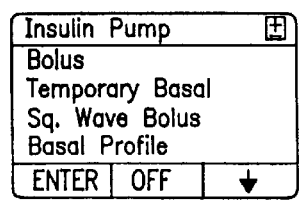
Figure 50C:
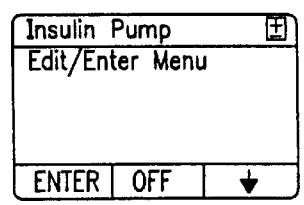
Figure 51A:
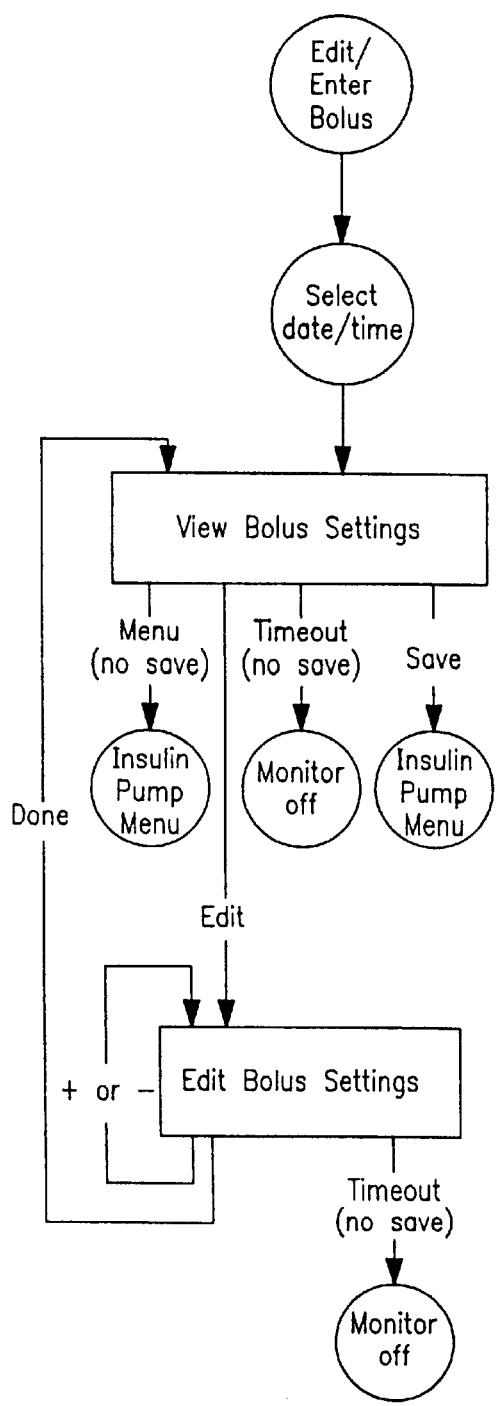
Figure 51B:
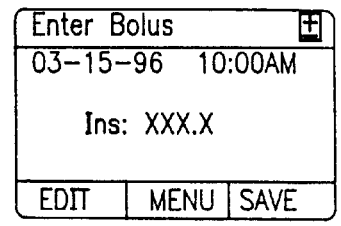
Figure 51C:
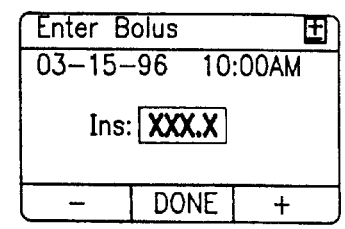
Figures 52A, 52B, 52C:
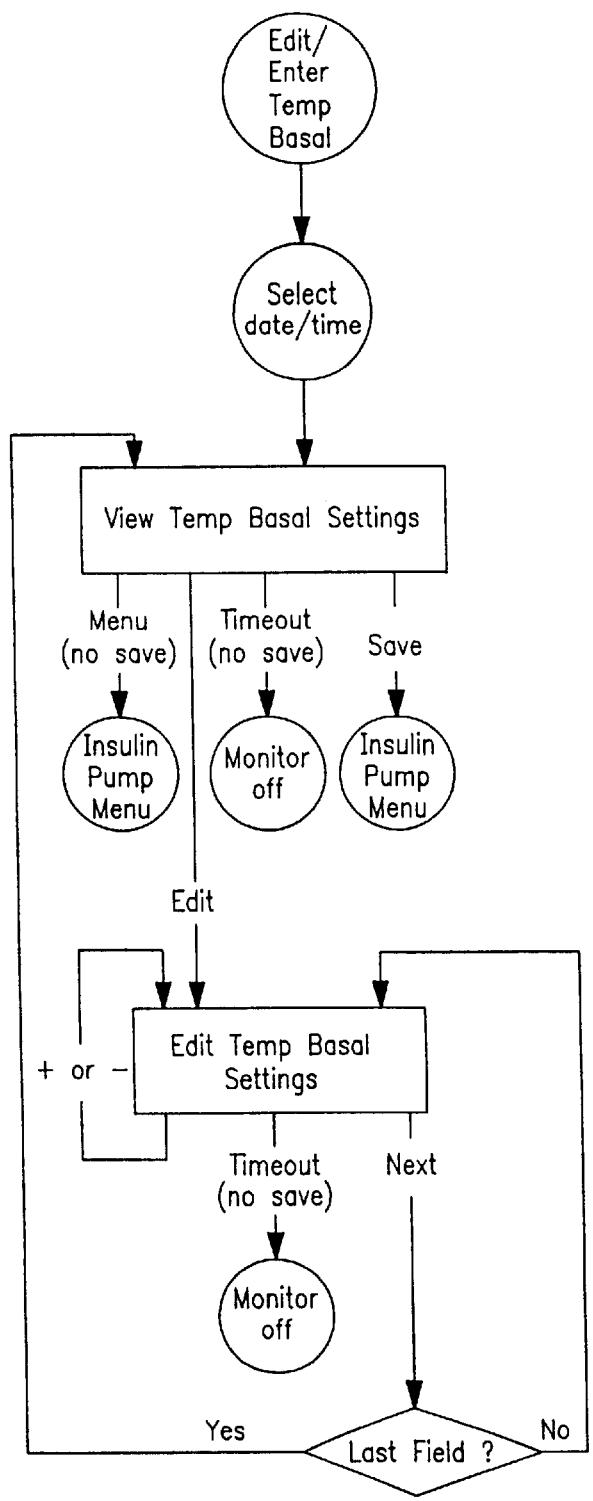
Figures 53A, 53B, 53C:
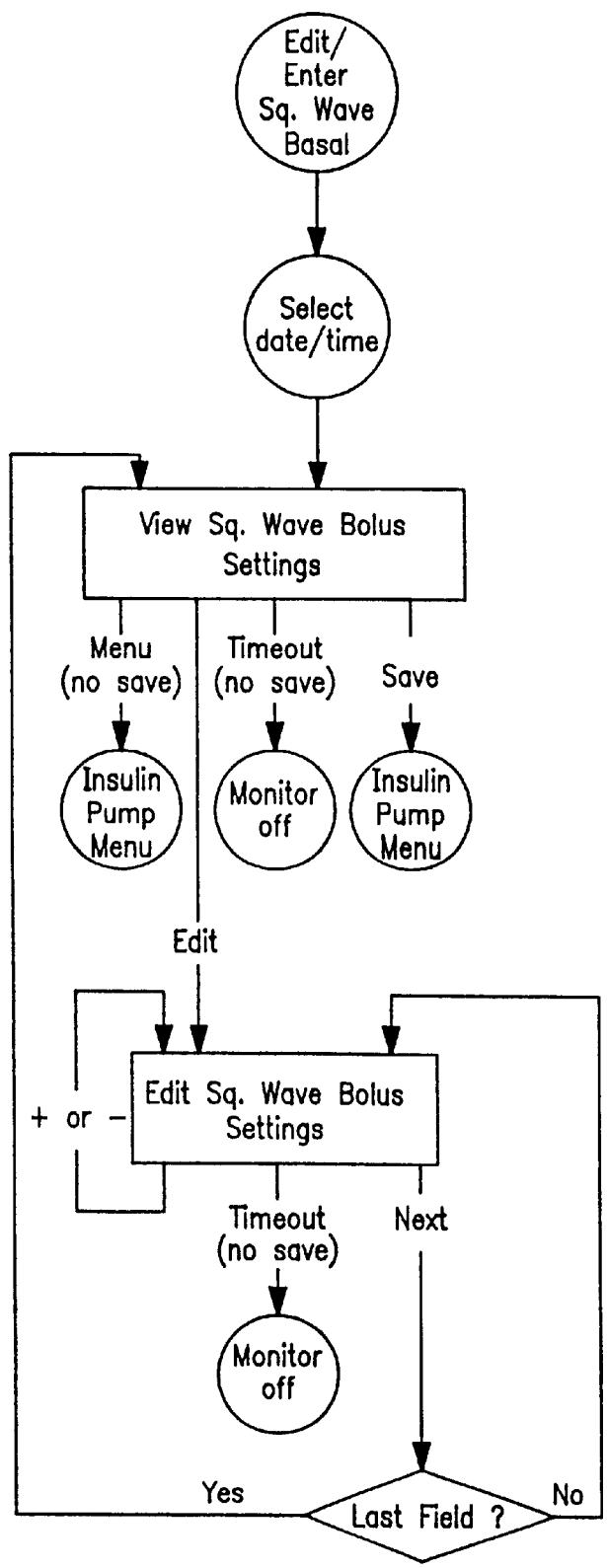

If the user elects the insulin pump option in FIG. 46*a*, the insulin pump menu screen illustrated in FIG. 50*b* is displayed on display 42. The user may select from the insulin pump menu options by scrolling down through the options using key 54*c* until the desired option is highlighted, and then pressing key 54*a* to select that option. The user may then: edit or enter data into the bolus settings as illustrated in FIGS. 51 *a–c*; edit or enter data into the temporary basal settings as illustrated in FIGS. 52*a–c*; edit or enter data into the square wave bolus settings as illustrated in FIGS. 53*a–c*; or, edit or enter basal profiles as illustrated in FIGS. 54*a–i*.

If the user elects to edit or enter the bolus settings, the user is first prompted to select the date and time. See FIGS. 48*a–b*. The bolus setting for the selected date and time is then displayed. See FIG. 51*b*. Pressing key 54*c* saves the displayed setting. No other action saves it. If the user wishes to change the displayed setting, the user presses key 54*a*. The setting is highlighted. See FIG. 51*c*. The user increases the setting by pressing key 54*c*, and reduces it by pressing key 54*a*. When the correct setting is reached, the user presses key 54*b* and then key 54*c* and the new setting is entered.

If the user elects to edit or enter temporary basal settings, the user is first prompted to select the date and time. See FIGS. 48*a–b*. The temporary basal setting for the selected date and time is then displayed. See FIG. 52*b*. Pressing key 54*c* saves the displayed setting. No other action does. If the user wishes to change the displayed setting, the user presses key 54*a*. A field of the setting is highlighted. See FIG. 52*c*. If the highlighted field is the field the user wishes to change, the user increases the setting by pressing key 54*c*, and reduces it by pressing key 54*a*. When the correct setting is reached, the user presses key 54*b* and then key 54*c* and the new setting is entered. If the highlighted field is not the field the user wishes to change, the user may advance to the field he or she wishes to change by pressing key 54*b* until the setting the user wishes to change is highlighted.

If the user elects to edit or enter square wave bolus settings, the user is first prompted to select the date and time. See FIGS. 48*a–b*. The square wave bolus setting for the selected date and time is then displayed. See FIG. 53*b*. Pressing key 54*c* saves the displayed setting. No other action does. If the user wishes to change the displayed setting, the user presses key 54*a*. A field of the setting is highlighted. See FIG. 53*c*. If the highlighted field is the field the user wishes to change, the user increases the setting by pressing key 54*c*,and reduces it by pressing key 54*a*. When the correct setting is reached, the user presses key 54*b* until the screen illustrated in FIG. 53*b* is displayed, and then key 54*c*,and the new setting is entered. If the highlighted field is not the field the user wishes to change, the user may advance to the field he or she wishes to change by pressing key 54*b* until the field the user wishes to change is highlighted.

If the user elects to edit or enter basal profiles, the user is first prompted to select the date and time. See FIGS. 48*a–b*. The basal profiles for the selected date are then displayed, beginning with the screen illustrated in FIG. 54*b*. The user may scroll forward and back through the profiles for the selected date by pressing keys 54*c* and 54*b*, respectively. The user may save the current settings for the selected date by pressing key 54*c* when the last screen is displayed. See FIG. 54*e*. No other action saves the current settings. To change the current settings, the user presses key 54*a*. A field of the settings is highlighted. See FIG. 54*f*. If the highlighted field is the one the user wishes to change, the user presses key 54*c* to increase the setting, and key 54*a* to decrease it. When the correct setting is reached, the user presses key 54*b* until the screen illustrated in FIG. 54*b* is displayed, and then key 54*c* through the screens illustrated in FIGS. 54*c–e*, and the new setting is entered. If the highlighted field is not the field the user wishes to change, the user may advance to the field he or she wishes to change by pressing key 54*b* until the field the user wishes to change is highlighted.

Figures 55A, 55B, 55C:
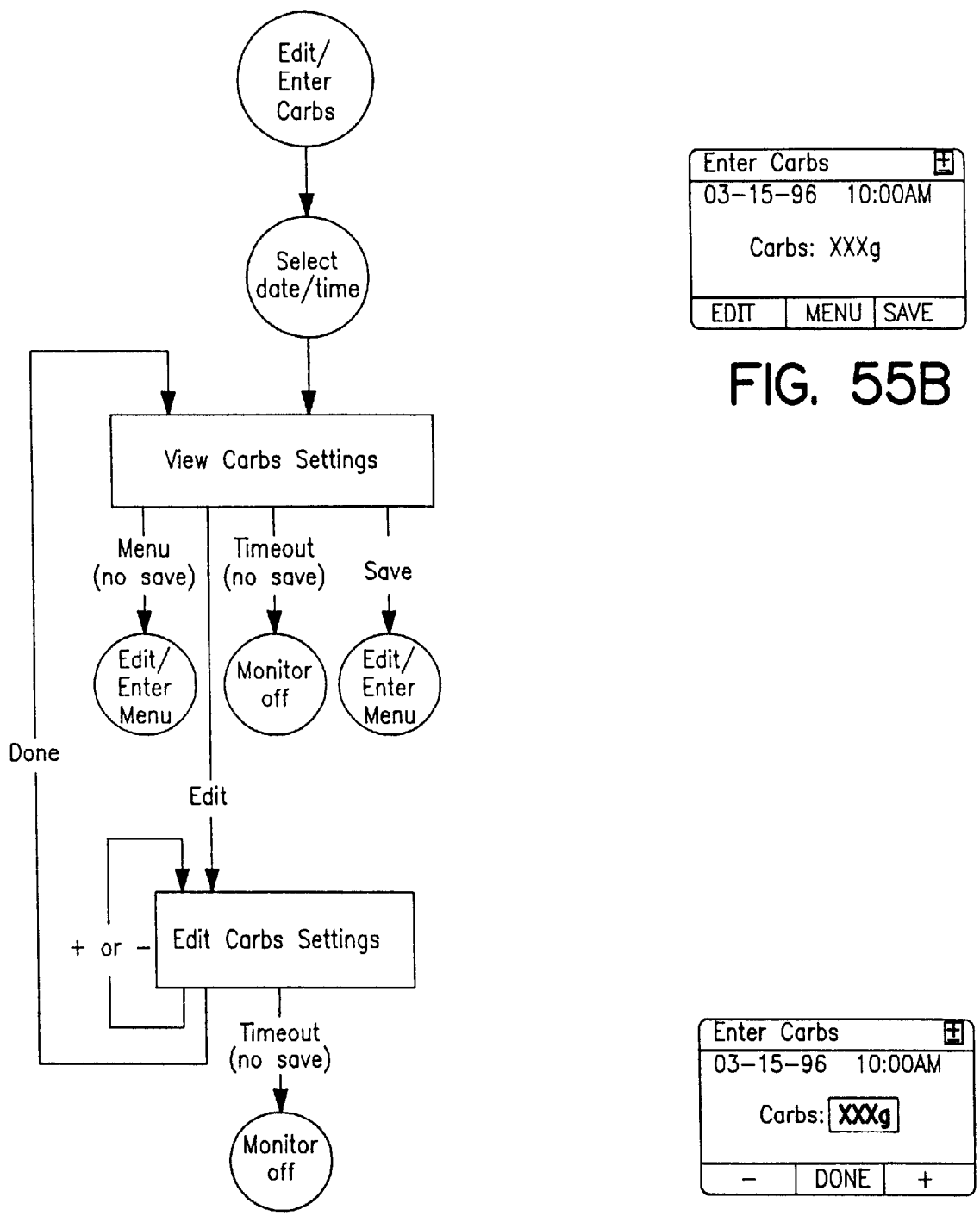

Returning to FIG. 46*a*, if the user elects the edit/enter carbohydrates option, the user is first prompted to select the date and time. See FIGS. 48*a–b*. The carbohydrates setting for the selected date and time is then displayed. See FIG. 55*b*. Pressing key 54*c* saves the displayed setting. No other action does. If the user wishes to change the displayed setting, the user presses key 54*a*. The screen illustrated in FIG. 55*c* is displayed. The user increases the setting by pressing key 54*c* and decreases it by pressing key 54*a*. When the correct setting is displayed, the user presses first key 54*b* to display the screen illustrated in FIG. 55*b*, and then key 54*c* to save the changed entry.

Figures 56A, 56B, 56C, 56D, 56E:
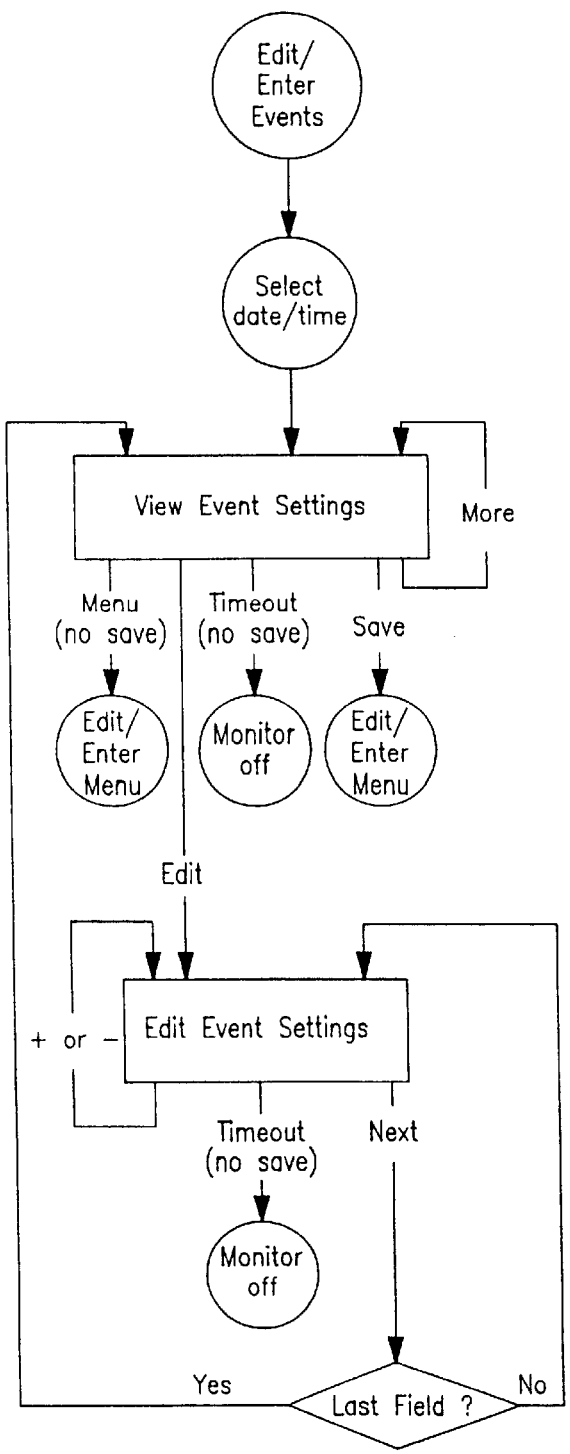

Returning to FIG. 46*a*, if the user elects the edit/enter events option, the user is first prompted to select the date and time. See FIGS. 48*a–b*. The screen illustrated in FIG. 56*b* is displayed. Pressing key 54*c* advances through the event screens. See FIG. 56*c*. Pressing key 54*c* when screen 56*c* is displayed saves the displayed settings. No other action does. If the user wishes to change a displayed setting, the user presses key 54*a*. The screen illustrated in FIG. 56*d* is displayed. If the highlighted field is the one the user wishes to change, the user presses keys 54*a* and *c* to scroll through the various available event texts until the correct one is displayed, then presses key 54*b* until the display illustrated in FIG. 56*b* is displayed, then key 54*c* until the changed entry is saved.

Figures 57A, 57B, 57C:
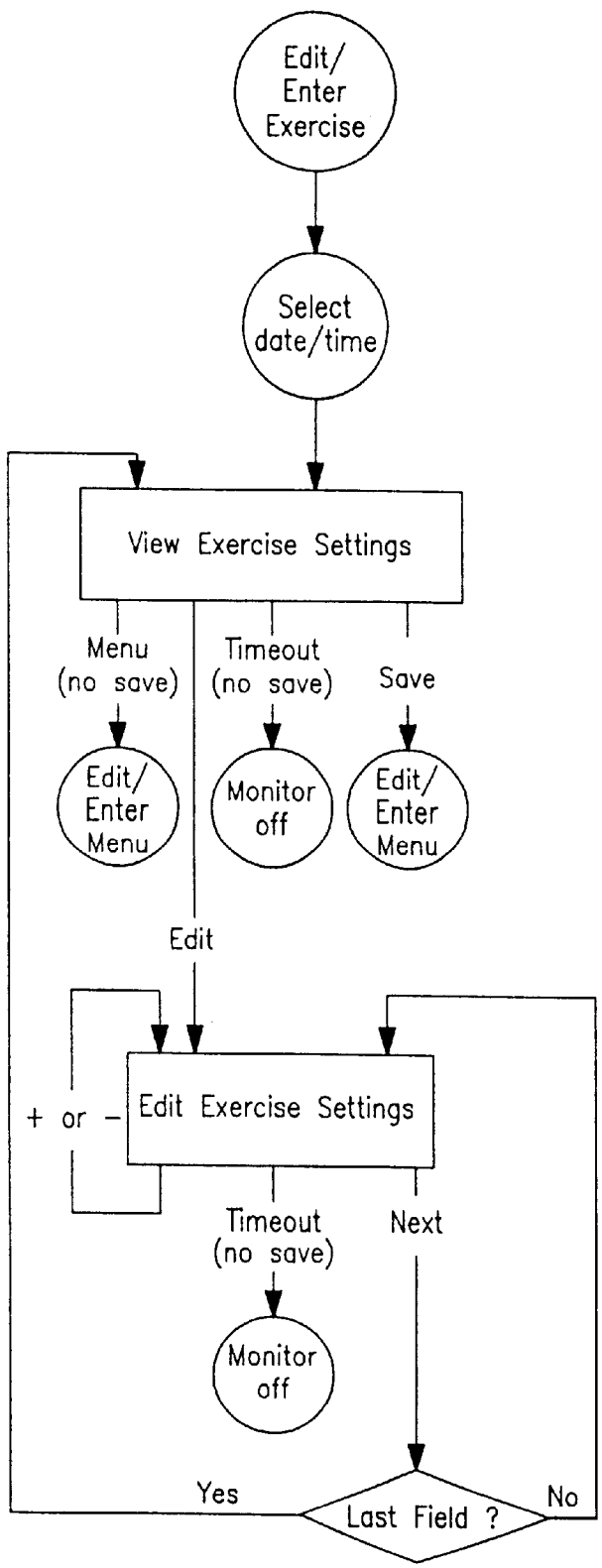

Returning to FIG. 46*a*, if the user elects the edit/enter exercise option, the user is first prompted to select the date and time. See FIGS. 48*a–b*. The screen illustrated in FIG. 57*b* is displayed. Pressing key 54*c* when screen 60*b* is displayed saves the displayed settings. No other action does. If the user wishes to change a displayed setting, the user presses key 54*a*, and the screen illustrated in FIG. 57*c* is displayed. If the highlighted field is the one the user wishes to change, the user presses keys 54*a* and *c* to scroll through the various available exercise texts until the correct one is displayed, then presses key 54*b*, returning to the display illustrated in FIG. 57*b*. The user then presses key 54*c* to save the changed entry.

Figures 58A, 58B, 58C:
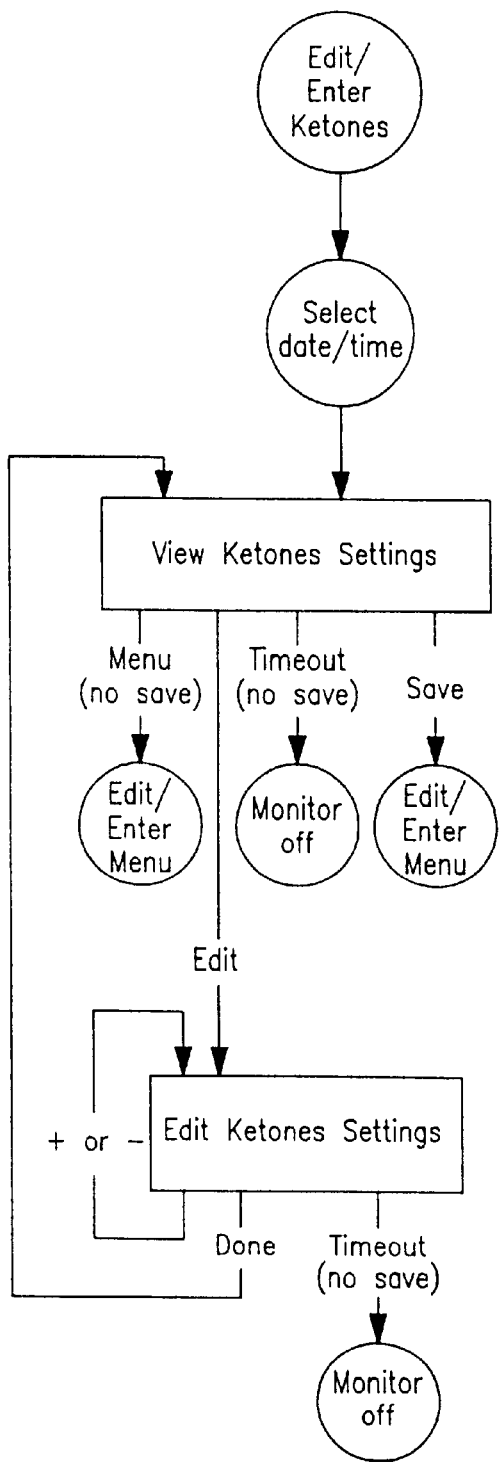

Returning to FIG. 46a, if the user elects the edit/enter ketones option, the user is first prompted to select the date and time. See FIGS. 48a–b. The screen illustrated in FIG. 58b is then displayed. Pressing key 54c when the screen illustrated in FIG. 58b is displayed saves the displayed settings. No other action does. If the user wishes to change the displayed settings, the user presses key 54a, and the screen illustrated in FIG. 58c is displayed. The user presses keys 54a and c to scroll through the various ketones texts until the correct one is displayed, and then presses key 54b, returning to the display illustrated in FIG. 58b. The user then presses key 54c to save the changed entry.

Figure 59A:
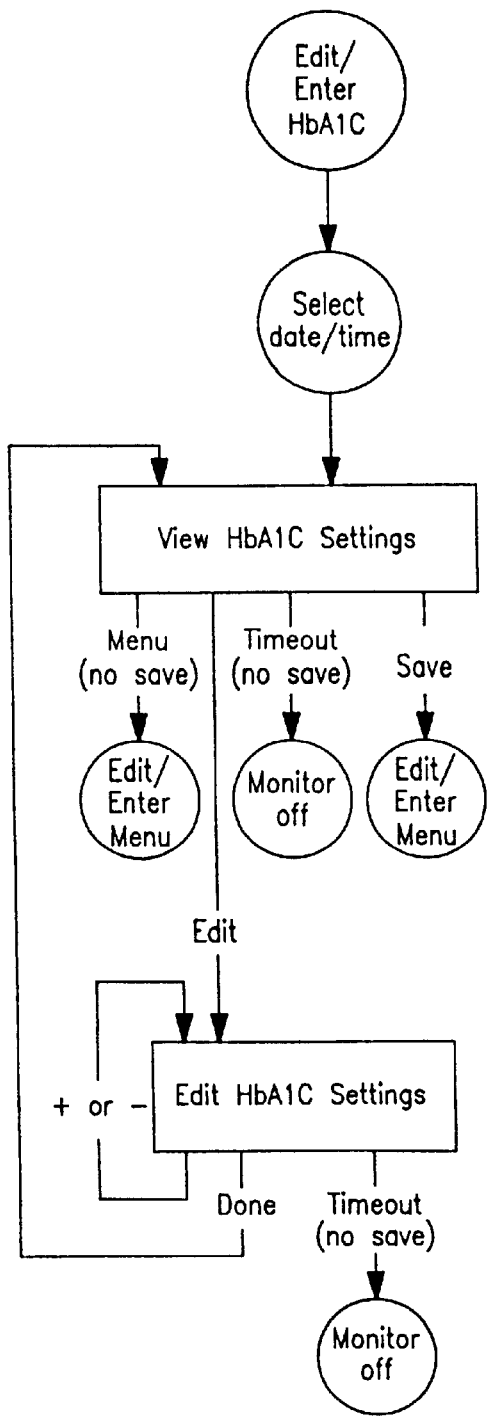
Figure 59B:
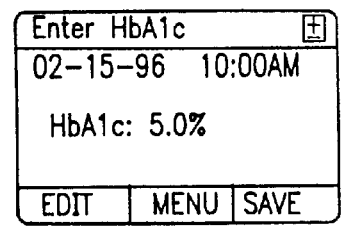
Figure 59C:
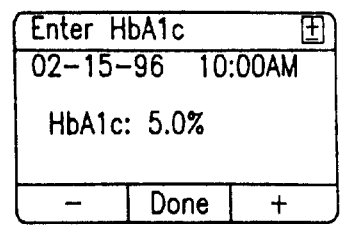

Returning to FIG. 46a, if the user elects the edit/enter glycosylated hemoglobin, the user is first prompted to select the date and time. See FIGS. 48a–b. The screen illustrated in FIG. 59b is then displayed. Pressing key 54c when the screen illustrated in FIG. 59b is displayed saves the displayed settings. No other action does. If the user wishes to change the displayed settings, the user presses key 54a, and the screen illustrated in FIG. 59c is displayed. The user presses keys 54a and c until the correct entry is displayed, and then presses key 54b, returning to the display illustrated in FIG. 59b. The user then presses key 54c to save the changed entry.

Figures 60A, 60B, 60C:
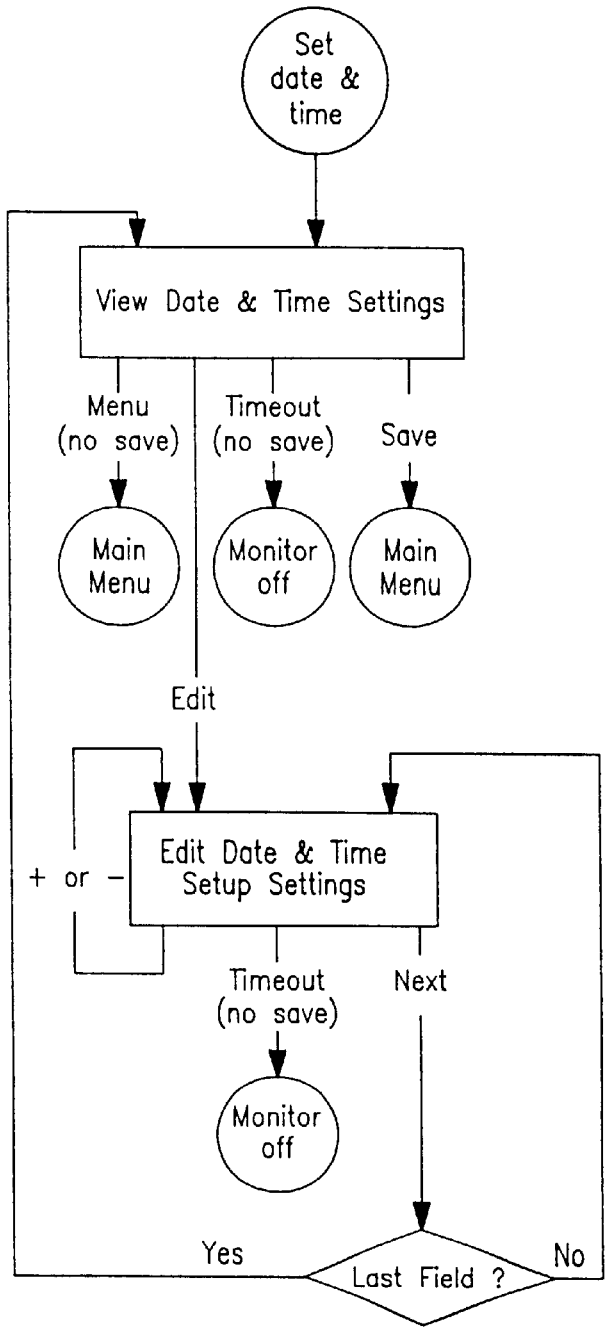
Figure 61A:
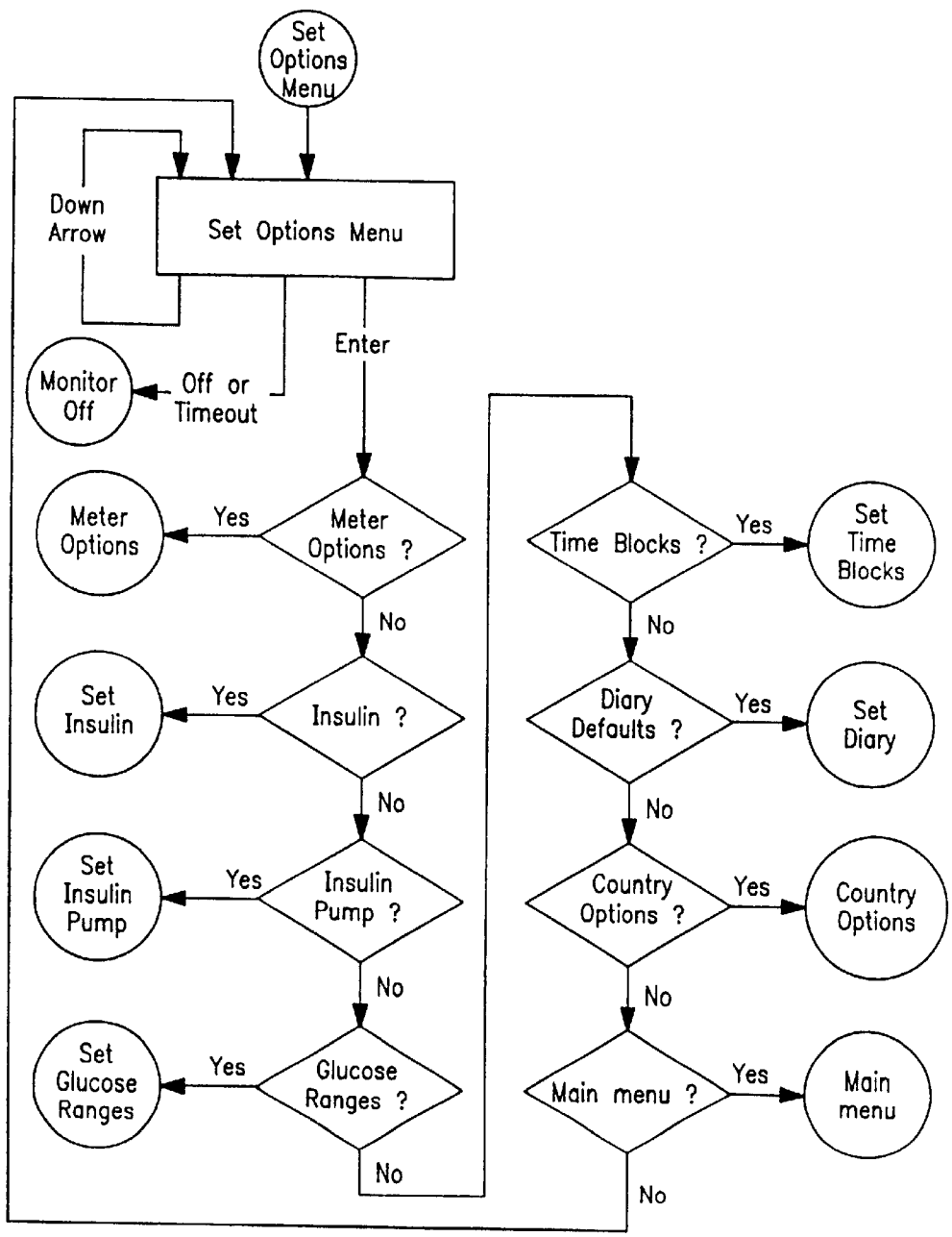

The user may need to set the correct date and time, for example, when the batteries 75 have been out of the instrument 20 for more than an hour or so, discharging the supercapacitor. Other date and time parameters, such as, for example, whether the user prefers a twelve hour clock or a twenty-four hour clock, or whether the user prefers the date displayed as day, month and year or as month, day and year, are also user selectable. If the user selects the set date and time option from FIG. 35b, the date and time screen illustrated in FIG. 60b is displayed. Pressing key 54c when the screen illustrated in FIG. 60b is displayed saves the displayed settings. No other action does. If the user wishes to change the displayed settings, the user presses key 54a, and the screen illustrated in FIG. 60c is displayed. If the highlighted field is the one the user wishes to change, the user presses keys 54a and c until the correct field is displayed. The user then presses key 54b to return to the display illustrated in FIG. 60b, and then presses key 54c to save the corrected date and time. If the highlighted field is not the one the user wishes to change, the user presses key 54b to advance through the fields until the one the user wishes to change is highlighted.

Figure 61B:
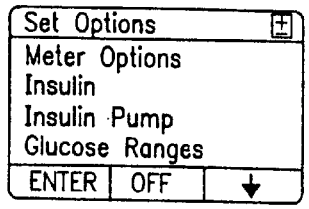
Figure 61C:
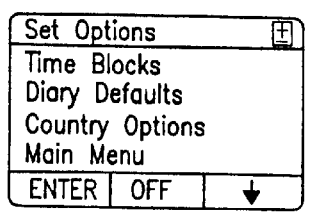
Figures 62A, 62B, 62C:
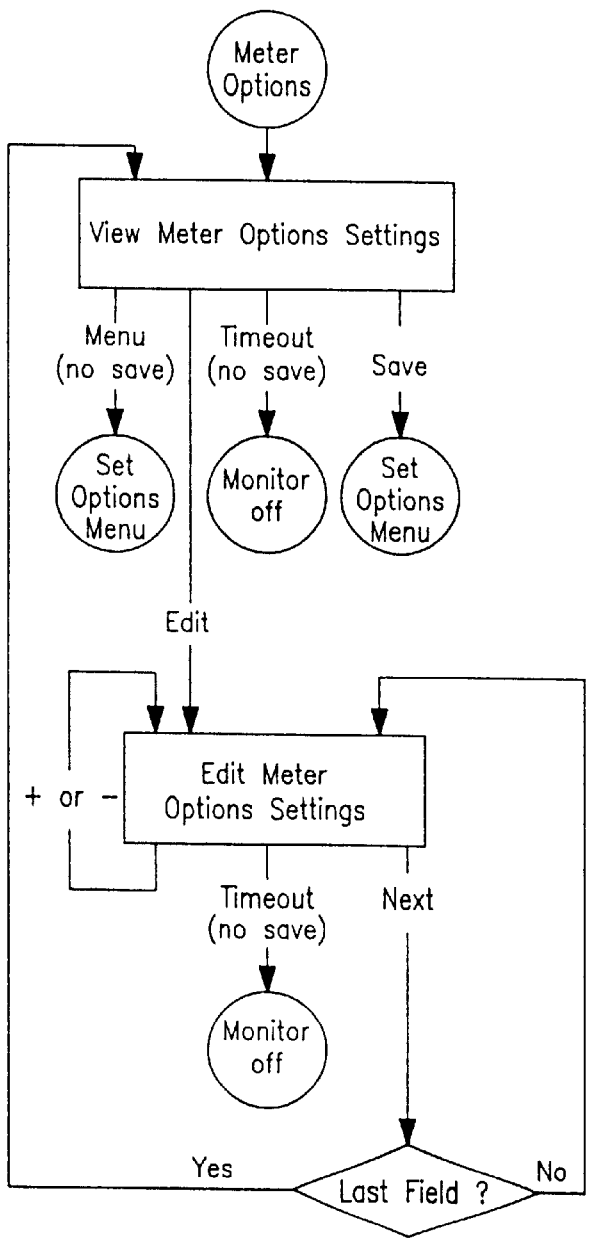

If the user selects the set options menu from FIG. 35c, the screen illustrated in FIG. 61b is displayed. The user may select from among several options in the illustrated instrument 20, including: meter options; insulin; insulin pump; glucose ranges; setting the time blocks; setting the diary; and, country (language) options. The user can scroll downward through the various options using key 54c. Pressing key 54a when a particular option is highlighted results in entry into a routine to set that option. For example, and with reference to FIGS. 62a–c, the user can elect to have the buzzer 37 power switch 170 enabled or disabled, the backlight power switch 154 enabled or disabled, and the scrolling messages or tips enabled or disabled. If the user elects to view the meter options, the screen illustrated in FIG. 62b is displayed. Pressing key 54c when the screen illustrated in FIG. 62b is displayed saves the current meter setup options. No other action does. If the user wishes to change the meter setup options, he or she presses key 54a. This results in the display of the screen illustrated in FIG. 62c. The user may change the setup of the highlighted option by pressing either key 54a or key 54c. Pressing key 54b through all of the remaining options returns the user to the screen illustrated in FIG. 62b. Pressing key 54c saves the changed setup options. If the highlighted option in FIG. 62c is not the one the user wishes to change, the user may press key 54b to advance through the available options until the one the user wishes to change is highlighted.

Figure 63A:
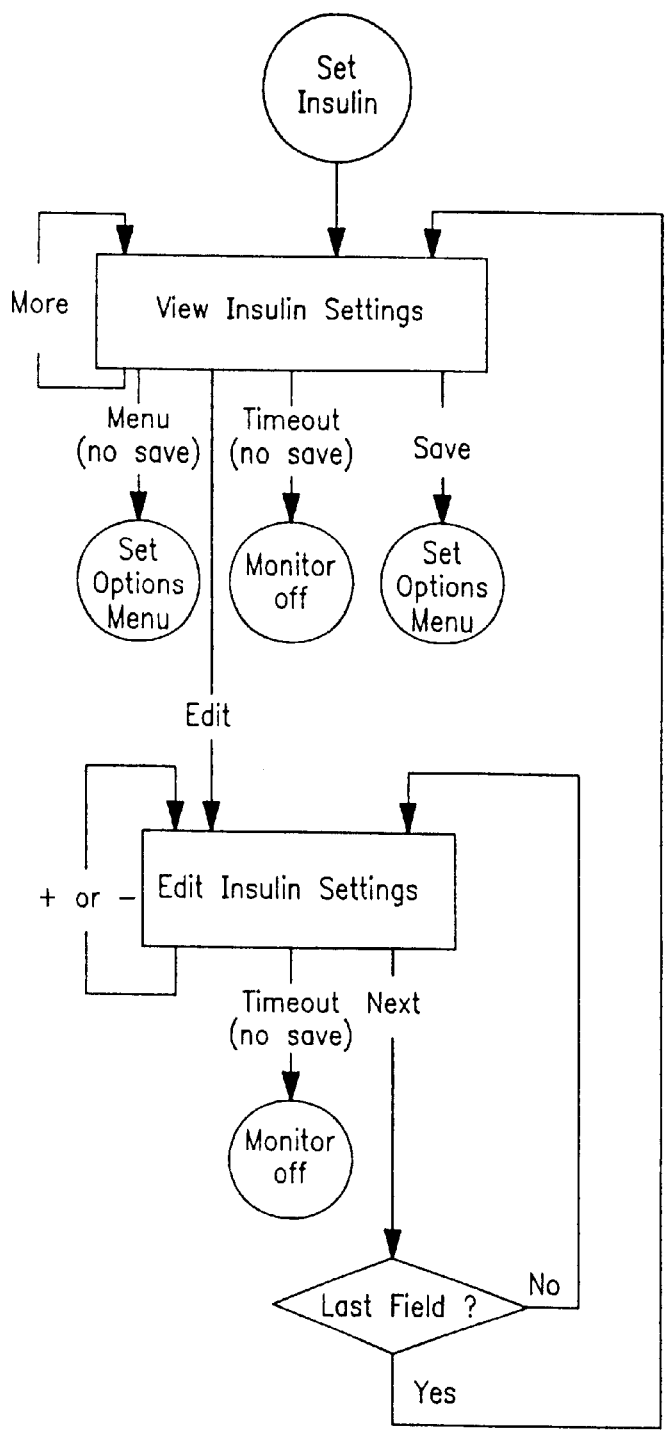
Figure 63B:
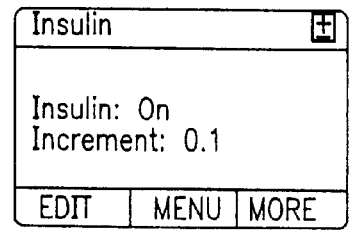
Figure 63C:
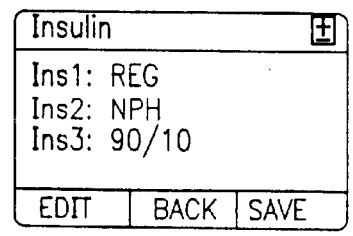
Figure 63D:
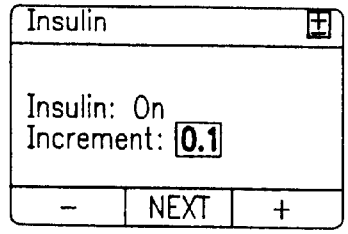
Figure 63E:
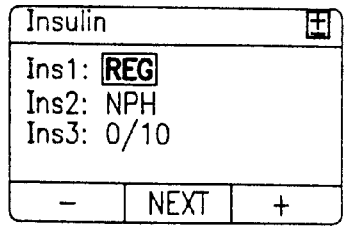

If the user elects the set insulin option from FIG. 61a, the screen illustrated in FIG. 63b is displayed. Pressing key 54c displays for the user the screen illustrated in FIG. 63c. If the user wishes to save these settings, he or she may do so by pressing key 54c. No other action will save these settings. If the user wishes to change any of these settings he or she may press key 54a. The screen illustrated in FIG. 63d will be displayed. If the highlighted setting is the one the user wishes to change, the user may press keys 54a and c until the setting is changed to the appropriate new setting. The user can then press key 54b until the screen illustrated in FIG. 63b is displayed, and then press key 54c until the new settings are saved. If the highlighted setting is not the one the user wishes to change, the user may press key 54b until the highlighted setting is the one the user wishes to change.

If the user elects the insulin pump option from FIG. 61a, the screen illustrated in FIG. 64b is displayed. If the user wishes to save this setting, he or she may do so by pressing key 54c. No other action will save this setting. If the user wishes to change this setting, he or she may press key 54a. The setting will be changed. Pressing key 54c will save the changed setting.

Figures 65A, 65B, 65C:
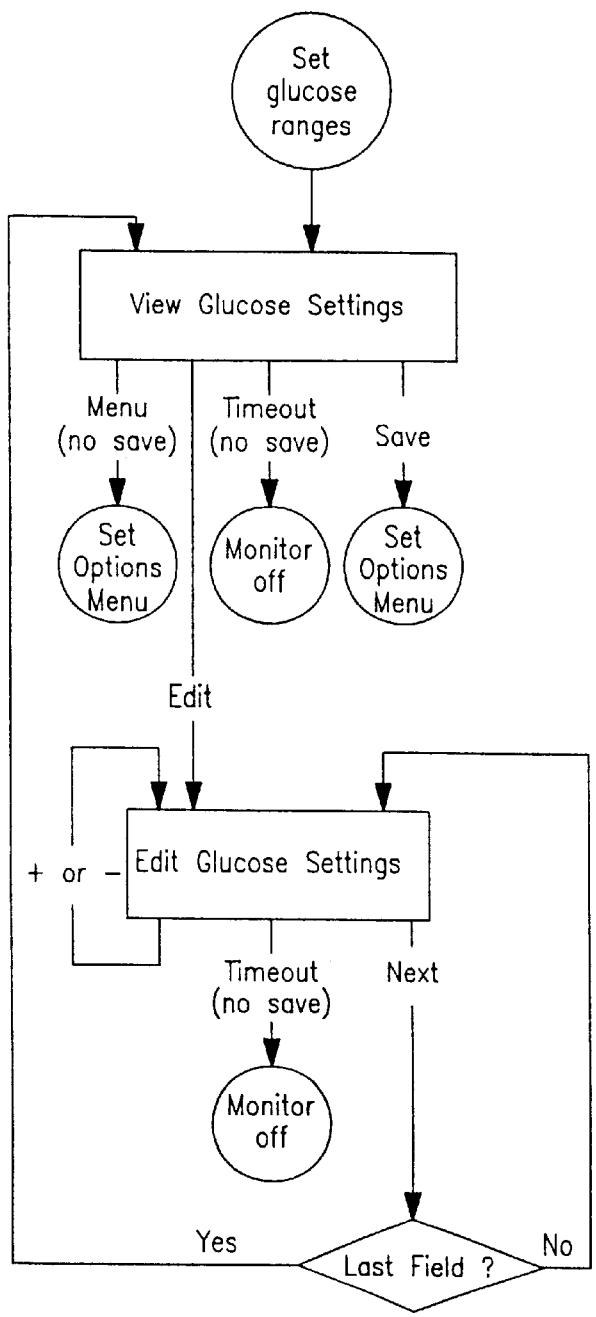

If the user elects the set glucose ranges option from FIG. 61a, the screen illustrated in FIG. 65b will be displayed. If the user wishes to save these settings, he or she may do so by pressing key 54c. No other action will save these settings. If the user wishes to change these settings, he or she may press key 54a. The screen illustrated in FIG. 65c will be displayed. If the highlighted setting is the one the user wishes to change, the user may change the setting by pressing one of keys 54a and 54c until the correct setting appears in the highlighted area. The user then presses key 54b until the display returns to the screen illustrated in FIG. 65b. The user then presses key 54c to save the correct setting. If the highlighted setting is not the one the user wishes to change, the user presses key 54b until the highlighted setting is the one to be changed, and proceeds as described above.

Figures 66A, 66B, 66C, 66D, 66E:
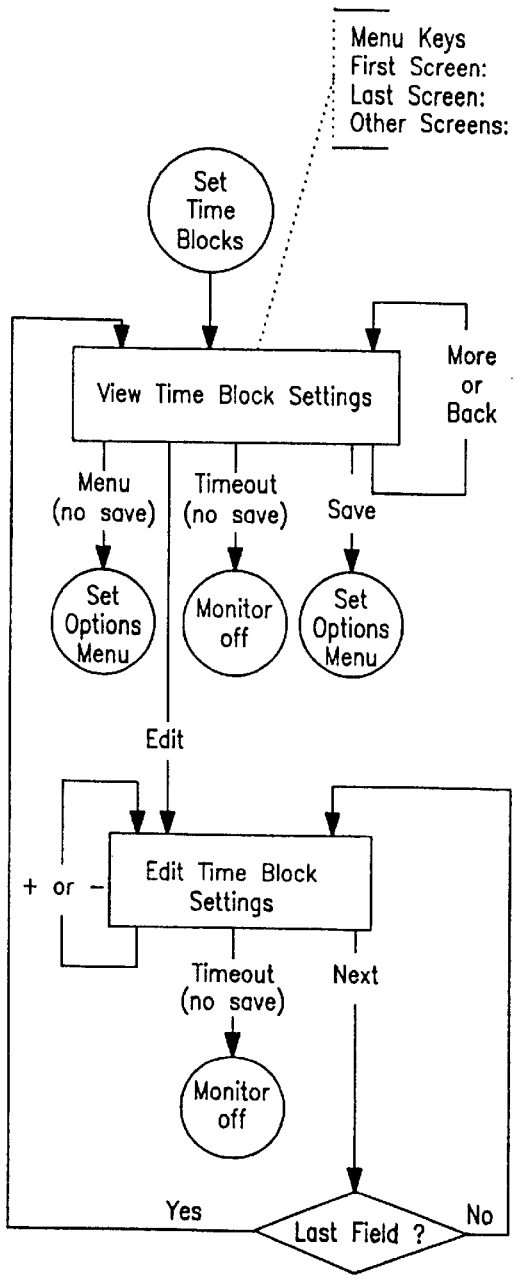

If the user elects the set time blocks option from FIG. 61a, the screen illustrated in FIG. 66b will be displayed. The user may refer back and forth between the screen illustrated in FIG. 66b and the screen illustrated in FIG. 66c by pressing key 54c when the screen of FIG. 66b is displayed and key 54b when the screen of FIG. 66c is displayed. The user may save the settings of FIGS. 66b–c by pressing key 54c when the screen of FIG. 66c is displayed. No other action will save these settings. If the user wishes to change the times in any blocks, the user may press key 54a. The screen illustrated in FIG. 66d will be displayed. If the user wishes to change the highlighted entry, the user may do so by pressing keys 54a and 54c until the desired entry appears in the highlighted area. The user may then advance through the remaining entries, one at a time, making any other desired changes to the remaining entries as they are highlighted, in the same manner as the changes were made to the first highlighted entry. In the illustrated instrument 20, only the beginning times of the various time blocks are user selectable. The ending times are calculated by the instrument 20 to be one minute before the starting times of the next subsequent time blocks and are entered automatically by the instrument 20. After the last entry is highlighted, and changed if desired, pressing key 54b will return the display to screen 66b. To save the changes, the user need only press key 54c to display screen 66c, and then press key 54c again to save the changes.

If the user elects the set diary defaults option from FIG. 61a, the screen illustrated in FIG. 67b will be displayed. Pressing key 54c will scroll the display down until the time block whose diary default settings are to be changed is highlighted. If the user wishes to change any of the diary default settings for a highlighted time block, the user presses key 54a. The screen illustrated in FIG. 67c is displayed. The user may move back and forth among the various screens illustrated in FIGS. 67c–g by pressing keys 54c to advance to the next subsequent screen (FIGS. 67c–f only) and 54b to go back to the immediately preceding screen (FIGS. 67d–g only). The user may save the current diary default settings by pressing key 54c when the screen illustrated in FIG. 67g is displayed. No other action will save the current settings. If the user wishes to change the current settings, the user need only press key 54a and the screen illustrated in FIG. 67h will be displayed. The user may change the highlighted entry by pressing keys 54a and c until the highlighted entry is correct. If the highlighted entry is not to be changed, the user may advance through the entries by pressing key 54b until the entry to be changed is highlighted. The user may then change that entry as described above. Pressing key 54b after the last entry illustrated in FIG. 67l is highlighted returns the user to the screen illustrated in FIG. 67c. The corrected diary default settings are then saved by advancing to the screen illustrated in FIG. 67g and pressing key 54c.

Figures 68A, 68B, 68C:
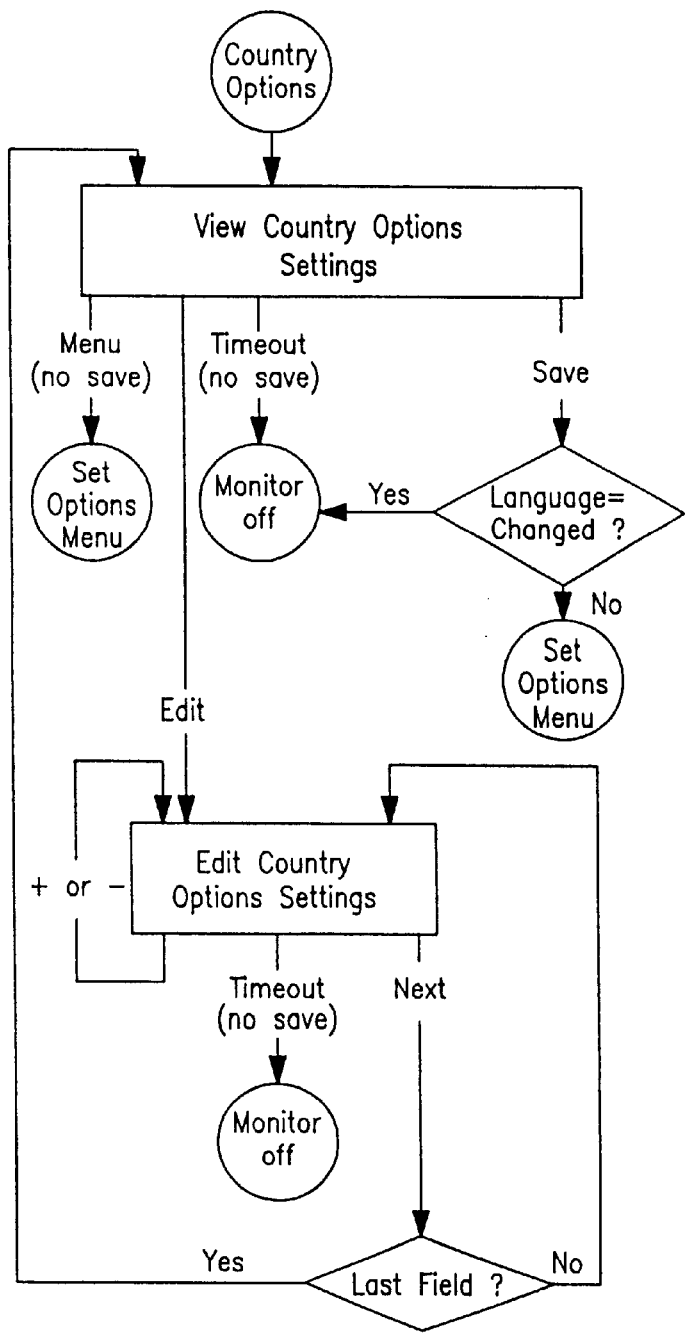

If the user elects the set country option from FIG. 61a, the screen illustrated in FIG. 68b is displayed. If the user does not wish to change the settings, the user may press key 54c and save the settings. If the settings are saved, the routine checks to be sure that a different language has been selected for the user interface. If not, control is returned to the set options menu. If a different language has been selected, the instrument 20 is powered down. If the user wishes to change any setting, the user presses key 54a. The screen illustrated in FIG. 68c is displayed. The user can advance through the available options for the highlighted setting by pressing keys 54a and 54c until the desired option appears. The user may then press key 54b to highlight the next setting, and then press keys 54a and 54c if any change is desired in the next highlighted option. The user may continue to do this until pressing key 54b returns the user to the screen illustrated in FIG. 68b. The user then presses key 54c to save the revised settings.

If the user selects the check battery option from FIGS. 35a–c, the screen illustrated in FIG. 69b is displayed. The shading of the battery in the screen corresponds to the batteries 75s' voltage. The user may return from this display to the main menu, turn the instrument 20 off, or permit to time itself off.

Referring to FIGS. 70a–b, the illustrated instrument also keeps track of certain additional events and parameters. Pressing of keys 54a–c simultaneously causes the screen illustrated in FIG. 70b to be displayed. This screen displays the instrument 20's serial number (S:sssssss), the version of the firmware with which the instrument 20 is operating (V:v.vv), the number of times the instrument 20 has been powered up (C1:11111), the number of glucose concentration determinations the instrument 20 has run (C2:22222) and the number of times the instrument 20 has been reset (C3:33333).

What is claimed is:

1. An electrical apparatus for use with an electrical cell for providing power, the cell having two terminals, the apparatus including a first connector for contacting one of the terminals and a second connector for contacting the other of the terminals when the cell is installed in the apparatus, the second connector including: a base portion fixed in apparatus, a first generally planar leg portion resiliently connected to and extending away from the base portion, a second generally planar leg portion resiliently connected to and extending away from the base portion, and a third generally planar leg portion resiliently connected to and extending away from the second generally planar leg portion and toward the first generally planar leg portion, installation of the cell in the apparatus causing the other terminal to resiliently engage the second generally planar leg portion.

2. The electrical apparatus of claim 1 comprising an instrument for determining the concentration of a medically significant component of a biological sample.

3. The electrical apparatus of claim 1 further comprising a dry cell, the installation of the dry cell in the apparatus causing the one terminal to engage the first connector.

4. The electrical apparatus of claim 1 including a circuit board to which the base portion of the second connector is fixed.

5. The electrical apparatus of claim 1 wherein the first generally planar leg portion of the second extends away from the base portion at an angle between about five degrees and about ten degrees with respect to a line perpendicular to the base portion ad generally in a first direction, the second generally planar leg portion extends away from the first generally planar leg portion at an angle between about fifteen degrees and about twenty five degrees with respect the perpendicular line and generally in a second direction opposite to first direction, and the third generally planar leg portion extends toward the base portion at an angle of between about forty degrees and about fifty degrees with respect to the perpendicular line and generally in the first direction.

6. The electrical apparatus of claim 5 wherein the second connector comprises BeCu 190 alloy.

7. The electrical apparatus of claim 6 wherein the second connector comprises a 60/40 tin/lead plating.

8. The electrical apparatus of claim 5 wherein the radii of curvature of the portions of the second connector between the base portion and the first generally planar leg portion, the first generally planar leg portion and the second generally planar leg portion, and the second generally planar leg portion and the third generally planar leg portion are substantially constant.

9. The electrical apparatus of claim 8 wherein the third generally planar leg portion has an extension that extends away from the base portion, and wherein the radius of curvature of the portion of the second connector between the extension and the third generally planar leg portion is also substantially constant.

10. An electrical apparatus for use with an electrical cell for providing power, the cell having two terminals, the apparatus including a first connector for contacting one of the terminals and a second connector for contacting the other of the terminal when the cell is installed in the apparatus, the second connector including: a base portion fixed in the apparatus, a first generally planar leg portion resiliently connected to and extending away from the base portion, a second generally planar leg portion resiliently connected to and extending away from the first generally planar leg portion, and a third generally planar leg portion resiliently connected to and extending away from the second generally planar leg portion and toward the first generally planar leg portion, installation of the cell in the apparatus causing the other terminal to resiliently engage the second generally planar leg portion, a well for receiving the cell, the well including an opening through which the first connector is exposed to the well, a boss adjacent the opening, the boss precluding the other terminal from engaging the first connector when the cell is inserted into the well in incorrect orientation.

11. The electrical apparatus of claim 10 comprising an instrument for determining the concentration of a medically significant component of a biological sample.

12. The electrical apparatus of claim 10 further comprising a dry cell, the installation of the dry cell in the apparatus causing the one terminal to engage the first connector.

13. The electrical apparatus of claim 10 including a circuit board to which the base portion of the second connector is fixed.

14. The electrical apparatus of claim 10 wherein the first generally planar leg portion of the second connector extends away from the base portion at an angle between about five degrees and about ten degrees with respect to a line perpendicular to the base portion and generally in a first direction, the second generally planar leg portion extends away from the first generally planar leg portion at an angle between about fifteen degrees and about twenty five degrees with respect to the perpendicular line and generally in a second direction opposite to the first direction, and the third generally planar leg portion extends toward the base portion at an angle of between about forty degrees and about fifty degrees with respect to the perpendicular line and generally in the first direction.

15. The electrical apparatus of claim 14 wherein the second connector comprises BeCu 190 alloy.

16. The electrical apparatus of claim 15 wherein the second connector comprises a 60/40 tin/lead plating.

17. The electrical apparatus of claim 14 wherein the radii of curvature of the portions of the second connector between the base portion and the first generally planar leg portion, the first generally planar leg portion and the second generally planar leg portion, and the second generally planar leg portion and the third generally planar leg portion are substantially constant.

18. The electrical apparatus of claim 17 wherein the third generally planar leg portion has an extension that extends away from the base portion, and wherein the radius of curvature of the portion of the second connector between the extension and the third generally planar leg portion is also substantially constant.

19. An apparatus for determining the concentration of a medically significant component of a biological sample, the apparatus including first and second keys for use in operating the apparatus, the keys extending from a common support mounted in the apparatus, each of the keys having a reduced cross sectional hinge portion adjacent to the common support whereby substantially independent activation of the first and second keys is provide, a third key disposed between the first and second keys for use in operating the apparatus, the third key also having a reduced cross sectional hinge portion adjacent to a second support mounted in the apparatus, the common support having a relief portion for receiving the second support such that the three keys generally define a surface when the apparatus is assembled.

20. The apparatus of claim 19 including a housing having first and second portions, the apparatus including a circuit mounted to one of the housing portions and having a set of three terminals, the apparatus further including means for securing the keys when the first and second housing portions are assembled together such that the keys, when activated, operate respective ones of the terminals.

21. The apparatus of claim 20 including a compressible member disposed between the keys and the terminals of the circuit.

22. The apparatus of claim 21 wherein the compressible member comprises a resilient pad dimensioned to isolate the terminals physically to reduce the possibility of contaminants interfering with the operation of the instrument.

23. The apparatus of claim 20 wherein the means for securing the keys comprises pins extending from the other housing portion for reception in a corresponding plurality of openings disposed in the key supports to capture the supports between the other housing portion and the circuit.

24. An apparatus for determining the concentration of a medically significant component of a biological sample, the apparatus comprising a strip and an instrument, the instrument comprising a slot through which the strip is intended to be inserted, the strip having at least one electrical contact thereon in communication with the sample, the instrument including an electrical connector for engagement with the electrical contact of the strip when the strip is inserted into the instrument for determining the concentration, the instrument including first and second housing portions, the slot being provided in one of the portions and the connector being mounted in the other of the housing portions, the other housing portion including a member fixed thereto to engage the connector resiliently when the housing portions are assembled together to promote alignment of the connector with the slot, and a circuit board mounted in the other housing portion, the electrical connector disposed on the circuit board.

25. The apparatus of claim 24 wherein the slot has a rib portion for guiding the strip when the strip is inserted into the instrument to promote engagement of the electrical contact of the strip with the electrical connector of the instrument.

26. The apparatus of claim 25 wherein the resilient engagement of the member with the connector promotes alignment of the connector with the slot generally in a first direction, the rib portions guiding the strip in a second direction generally perpendicular to the first direction.

27. An apparatus for determining the concentration of a medically significant component of a biological sample, the apparatus comprising a strip and an instrument, the instrument comprising a slot through which the strip is intended to be inserted, the strip having at least one electrical contact thereon in communication with the sample, the instrument including an electrical connector for engagement with the electrical contact of the strip when the strip is inserted into the instrument for determining the concentration, the instrument including first and second housing portions, the slot being provided in one of the housing portions and the connector being mounted in the other of the housing portions, the other housing portion including a member fixed thereto to engage the connector resiliently when the housing portions are assembled together to promote alignment of the connector with the slot, and a second member fixed to the other housing portion for resiliently engaging the connector when the housing portions are assembled together to promote alignment of the connector with the slot in cooperation with the first-mentioned member.

28. A method of operating an instrument, the instrument including a housing for at least some of the instrument components, the instrument components housed within the housing having at least first and second operating states, the instrument components evolving heat at a first time rate when the instrument is in the first operating state and at a second time rate when the instrument is in the second operating state, the instrument components including a controller, the controller keeping a record of how long the instrument is operated in each of said first and second states and calculating from the record the heating of the interior of the housing resulting from the operation of the instrument in each of said first and second states.

29. The method of claim 28 wherein the instrument components housed within the instrument include a device for producing an output indicative of temperature, the method further comprising the step of adjusting the indicated temperature based upon the calculated heating of the interior of the housing.

30. The method of claim 29 wherein the step of adjusting the indicated temperature based upon the calculated heating of the interior of the housing comprises the step of subtracting the calculated heating of the interior of the housing from the indicated temperature.

31. The method of claim 30 wherein the instrument comprises an instrument for determining the concentration of a medically significant component of a sample, the method further comprising providing a strip, providing on the instrument a port for receiving the strip, inserting the strip into the port, dosing the strip with the sample, determining an ambient temperature within the housing, adjusting the determined ambient temperature to an adjusted ambient temperature based upon the heating of the interior of the housing resulting from the operation of the instrument in each of said first and second states, and determining the concentration of the medically significant component of the sample based upon the adjusted ambient temperature.

32. The method of claim 29 wherein the instrument comprises an instrument for determining the concentration of a medically significant component of a sample, the method further comprising providing a strip, providing on the instrument a port for receiving the strip, inserting the strip into the port, dosing the strip with the sample, determining an ambient temperature within the housing, adjusting the determined ambient temperature to an adjusted ambient temperature based upon the heating of the interior of the housing resulting from the operation of the instrument in each of said first and second states, and determining the concentration of the medically significant component of the sample based upon the adjusted ambient temperature.

33. The method of claim 28 wherein the instrument comprises an instrument for determining the concentration of a medically significant component of a sample, the method further comprising providing a strip, providing on the instrument a port for receiving the strip, inserting the strip into the port, dosing the strip with the sample, determining an ambient temperature within the housing, adjusting the determined ambient temperature to an adjusted ambient temperature based upon the heating of the interior of the housing resulting from the operation of the instrument in each of said first and second states, and determining the concentration of the medically significant component of the sample based upon the adjusted ambient temperature.

34. The method of claim 33, 32, or 31, wherein the strip contains a chemistry for reacting with the medically significant component of the sample and producing across two terminals of the strip a signal a indicative of the reaction, receiving the strip in the port and dosing of the strip enabling the determination of the concentration.

35. The method of claim 34 wherein the medically significant component is glucose and the chemistry reacts with glucose to produce at least one of a voltage and a current indicative of the glucose concentration of the sample across the terminals of the strip.

36. An instrument including a housing for at least some components of the instrument, the instrument components housed within housing having at least first and second operating states, the instrument components housed within the housing evolving heat at a first time rate when the instrument is in the first operating state and a second time rate when the instrument is in the second operating state, the instrument components including a controller for keeping a record of how long the instrument is operated in each of said first and second states and calculating from the record the heating of the interior of the housing resulting from the operation of the instrument in each of said first and second states, the instrument comprising an instrument for determining the concentration of a medically significant component of a sample, the apparatus further comprising a strip for dosing with the sample, the instrument including a port for receiving the strip, the controller adjusting the determined ambient temperature to an adjusted ambient temperature based upon the heating of the interior of the housing resulting from the operation of the instrument in each of said first and second states, and determining the concentration of the medically significant component of the sample based upon the adjusted ambient temperature.

37. The apparatus of claim 36 wherein the instrument components housed within the housing include a device for producing an output indicative of temperature, the controller coupled to the device for producing an output indicative of temperature for adjusting the indicated temperature based upon the calculated heating of the interior of the housing.

38. The apparatus of claim 37 wherein the controller is coupled to the device for producing an output indicative of temperature for subtracting the calculated heating of the interior of the housing from the indicated temperature.

39. An instrument including a housing for at least some of the instrument components of the instrument, the instrument components housed within the housing having at least first and second operating states, the instrument components housed within the housing evolving heat at a first time rate when the instrument is in the first operating state and at a second time rate when the instrument is in the second operating state, the instrument components including a controller for keeping a record of how long the instrument is operated in each of said first and second states and calculating from the record the heating of the interior of the housing resulting from the operation of the instrument in each of said first and second states, the instrument components housed within the housing including a device for producing an output indicative of temperature, the controller coupled to the device for producing an output indicative of temperature for adjusting the indicated temperature based upon the calculated heating of the interior of the housing, the instrument comprising an instrument for determining the concentration of a medically significant component of a sample, the apparatus further comprising a strip for dosing with the sample, the instrument including a port for receiving the strip, the controller adjusting the determined ambient temperature to an adjusted ambient temperature based upon the heating of the interior of the housing resulting from the operation of the instrument in each of said first and second states, and determining the concentration of the medically significant component of the sample based upon the adjusted ambient temperature.

40. The apparatus of claim 36 or 39 wherein the strip contains a chemistry for reacting with the medically significant component of the sample and at least two strip terminals, the port including at least two complementary instrument terminals, the strip terminals making contact with respective instrument terminals when the strip is inserted into the port, the chemistry reacting with the medically significant component of the sample to produce across at least two of the strip terminals a signal indicative of the reaction, receiving the strip in the port and dosing of the strip enabling the determination of the first concentration.

41. The apparatus of claim 40 wherein the medically significant component is glucose and the chemistry reacts with glucose to produce at least one of a voltage and a current indicative of the glucose concentration of the sample across the strip terminals.

42. The apparatus of claim 39 wherein the controller is coupled to the device for producing an output indicative of temperature for subtracting the calculated heating of the interior of the housing from the indicated temperature.

43. An instrument for determining the concentration of a medically significant component of a sample, the instrument including a controller and a power supply for providing power to the controller, the power supply including one or more cells for providing direct current at a first voltage, an inductance and a first solid state switch in series across the one or more cells, the controller providing a first switching signal for the first switch, a first rectifier and a first capacitance in a second circuit for rectifying and storing the voltage variations appearing across one of the first switch and inductance, the second circuit storing voltage variations of a first polarity appearing across one of the first switch and inductance and the third circuit storing voltage variations of a second and opposite polarity appearing across one of the first switch and inductance.

44. The apparatus of claim 43 further comprising a transistor-transistor logic-to-RS-232 (TTL-to-RS-232) interface, the TTL-to-RS-232 interface being coupled across the second circuit and the third circuit.

45. The apparatus of claim 43 further comprising a third rectifier and a third capacitance, the second and third rectifiers and the second and third capacitances in a fourth circuit configured as a voltage multiplier.

46. The apparatus of claim 43 further comprising a second switch in circuit with the first capacitance, the controller further providing a second switching signal for the second switch.

47. The apparatus of claim 46 wherein the second switch comprises a second solid state device for regulating the voltage across the first capacitance when the second switch is in a first state, the second solid state device halting regulation of the voltage across the first capacitance when the second switch is in a second state.

48. The apparatus of claim 43, 44, 45, 46 or 47 wherein the first switching signal is pulsewidth modulated.

49. An instrument for determining the concentration of a medically significant component of a sample, the instrument including a first key for selecting a function from a group of at least two functions, a second key, a controller for assigning to the second key the function selected from a group of at least two functions by the first key, and a display for displaying for the user an assignment by the controller of the function to the second key, a strip for dosing with the sample, the instrument including a port for receiving the strip to enable the instrument to determine the concentration of the medically significant component of the sample, the strip containing a chemistry for reacting with the medically significant component of the sample and a pair of strip terminals, the port including a complementary pair of instrument terminals, the strip terminals making contact with respective instrument terminals when the strip is inserted into the port, the chemistry reacting with the medically significant component of the sample to produce across the pair of strip terminals a signal indicative of the reaction, receiving the strip in the port and dosing of the strip enabling the determination of the first concentration.

50. The apparatus of claim 49 wherein the instrument comprises a hand held instrument for determining the glucose concentration of the sample.

51. A hand held instrument for determining the glucose concentration of a sample, the instrument including a first key for selecting a function from a group of at least two functions, a second key, a controller for assigning to the second key the function selected from a group of at least two functions by the first key, and a display for displaying for the user an assignment by the controller of the function to the second key, a strip for dosing with sample, the instrument including a port for receiving the strip to enable the instrument to determine the glucose concentration of the sample.

52. A hand held instrument for determining the glucose concentration of a sample, the instrument including a first key for selecting a function from a group of at least two functions, a second key, a controller for assigning to the second key the function selected from a group of at least two functions by the first key, and a display for displaying for the user an assignment by the controller of the function to the second key, a strip containing a chemistry for reacting with glucose in the sample, the instrument including a port for receiving the strip and a device for assessing the reaction of the chemistry with glucose in the sample and for producing a signal indicative of assessment, receiving the strip in the port and dosing of the strip enabling the determination of the glucose concentration of the sample.

53. An electrical apparatus for use with an electrical cell for providing power, the cell having two terminals, the apparatus including a first connector for contacting one of the terminals and a second connector for contacting the other of the terminals when the cell is installed in the apparatus, the second connector including: a base portion fixed in the apparatus, a first generally planar leg portion resiliently connected to and extending away from the base portion at an angle between about five degrees and about ten degrees with respect to a line perpendicular to the base portion and generally in a first direction, a second generally planar leg portion resiliently connected to and extending away from the first generally planar leg portion at an angle between about fifteen degrees and about twenty five degrees with respect to the perpendicular line and generally in a second direction apposite to the first direction, the second generally planar leg portion also extending away from the base portion, and a third generally planar leg portion resiliently connected to and extending away from the second generally planar leg portion and toward the first generally planar leg portion, the third generally planar leg portion extending toward the base portion at an angle of between about forty degrees and about fifty degrees with respect to the perpendicular line and generally in the first direction, installation of the cell in the apparatus causing the other terminal to resiliently engage the second generally planar leg portion.

54. The electrical apparatus of claim 53 wherein the second connector comprises BeCu 190 alloy.

55. The electrical apparatus of claim 54 wherein the second connector comprises a 60/40 tin/lead plating.

56. The electrical apparatus of claim 53 wherein the radii of curvature of the portions of the second connector between the base portion and the first generally planar leg portion, the first generally planar leg portion and the second generally planar leg portion, and the second generally planar leg portion and the third generally planar leg portion are substantially constant.

57. The electrical apparatus of claim 56 wherein the third generally planar leg portion has an extension that extends away from the base portion, and wherein the radius of curvature of the portion of the second connector between the extension and the third generally planar leg portion is also substantially constant.

* * * * *